United States Patent
Funk et al.

(10) Patent No.: US 10,814,099 B2
(45) Date of Patent: Oct. 27, 2020

(54) MEDICAL SYSTEM

(71) Applicant: Kardium Inc., Burnaby (CA)

(72) Inventors: John Andrew Funk, Delta (CA); Saar Moisa, Vancouver (CA); Ashkan Sardari, North Vancouver (CA)

(73) Assignee: KARDIUM INC., Burnaby (CA)

( * ) Notice: Subject to any disclaimer, the term of this patent is extended or adjusted under 35 U.S.C. 154(b) by 179 days.

(21) Appl. No.: 15/988,367

(22) Filed: May 24, 2018

(65) Prior Publication Data
US 2018/0264230 A1    Sep. 20, 2018

Related U.S. Application Data

(63) Continuation of application No. PCT/CA2016/000297, filed on Dec. 1, 2016.

(60) Provisional application No. 62/268,771, filed on Dec. 17, 2015.

(51) Int. Cl.
| | |
|---|---|
| A61M 25/01 | (2006.01) |
| A61B 17/00 | (2006.01) |
| A61M 25/09 | (2006.01) |
| A61M 25/00 | (2006.01) |

(52) U.S. Cl.
CPC ......... *A61M 25/0141* (2013.01); *A61B 17/00* (2013.01); *A61B 17/00234* (2013.01);
(Continued)

(58) Field of Classification Search
CPC .......... A61M 25/0147; A61M 25/0152; A61M 25/0053; A61M 25/0054; A61M 25/0141; A61M 2025/15
See application file for complete search history.

(56) References Cited

U.S. PATENT DOCUMENTS 5,951,539 A * 9/1999 Nita .................. A61M 25/0053
                                                                   604/524
8,702,647 B2 * 4/2014 Benscoter ............ A61B 1/0125
                                                                   600/146
(Continued)

FOREIGN PATENT DOCUMENTS

| WO | 2007136981 A2 | 11/2007 |
|---|---|---|
| WO | 2009137712 A1 | 11/2009 |

OTHER PUBLICATIONS

International Search Report issued in International Appln. No. PCT/CA2016/000297 dated Feb. 6, 2017.
(Continued)

*Primary Examiner* — Nathan R Price
*Assistant Examiner* — Tania Ismail
(74) *Attorney, Agent, or Firm* — Rossi, Kimms & McDowell LLP

(57) ABSTRACT

Medical systems are disclosed which may include an elongate shaft member and a plurality of steering lines operable to cause bending of the elongate shaft member via movement of at least one of the steering lines. A respective second end portion of a first proximal steering line may terminate at a first proximal termination portion of the elongate shaft member, and a respective second end portion of the first distal steering line may terminate at a first distal termination portion of the elongate shaft member. The elongate shaft member may be formed of materials of different hardness to provide preferential bending in desired directions.

56 Claims, 14 Drawing Sheets

(52) U.S. Cl.
CPC ........ *A61M 25/01* (2013.01); *A61M 25/0136* (2013.01); *A61M 25/0138* (2013.01); *A61M 25/0147* (2013.01); *A61M 25/09* (2013.01); *A61B 2017/00323* (2013.01); *A61M 25/0012* (2013.01); *A61M 25/0045* (2013.01); *A61M 2025/015* (2013.01); *A61M 2025/0161* (2013.01)

(56) References Cited

U.S. PATENT DOCUMENTS

| | | | | |
|---|---|---|---|---|
| 8,906,011 | B2 * | 12/2014 | Gelbart | A61B 5/065 606/41 |
| 2003/0171736 | A1 | 9/2003 | Bon | |
| 2007/0299424 | A1 | 12/2007 | Cumming et al. | |
| 2009/0287187 | A1 | 11/2009 | Legaspi et al. | |
| 2010/0168666 | A1 | 7/2010 | Tegg | |

OTHER PUBLICATIONS

Written Opinion issued in International Appln. No. PCT/CA2016/000297 dated Feb. 6, 2017.

Mounsey. "A novel multielectrode combined mapping and ablation basket catheter: A future player in the atrial fibrillation ablation space?" Journal of Cardiovascular Electrophysiology. 2017:1-2.

Kottkamp et al. "Global multielectrode contact mapping plus ablation with a single catheter: Preclinical and preliminary experience in humans with atrial fibrillation." Journal of Cardiovascular Electrophysiology. 2017:1-10.

* cited by examiner

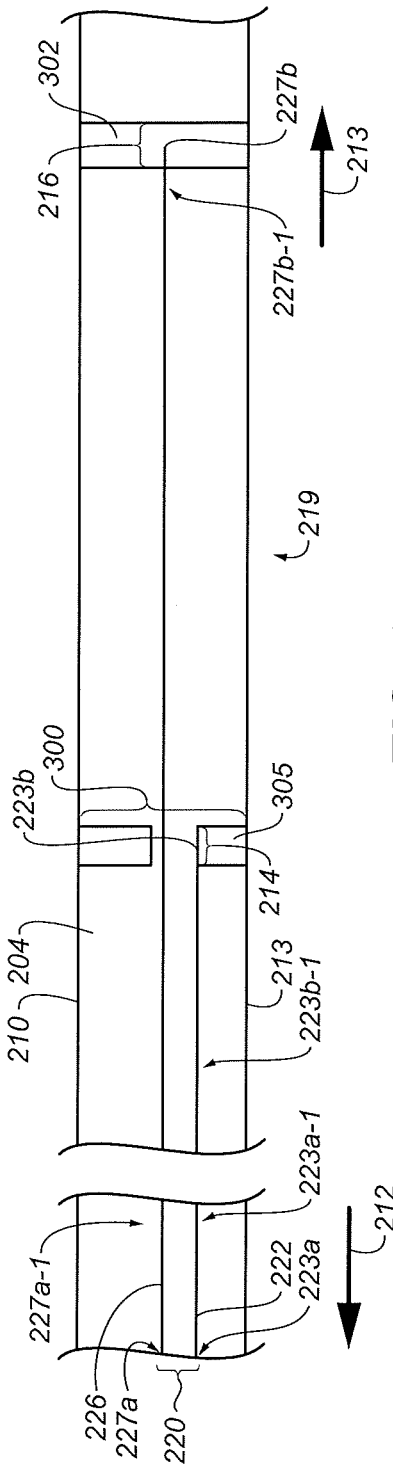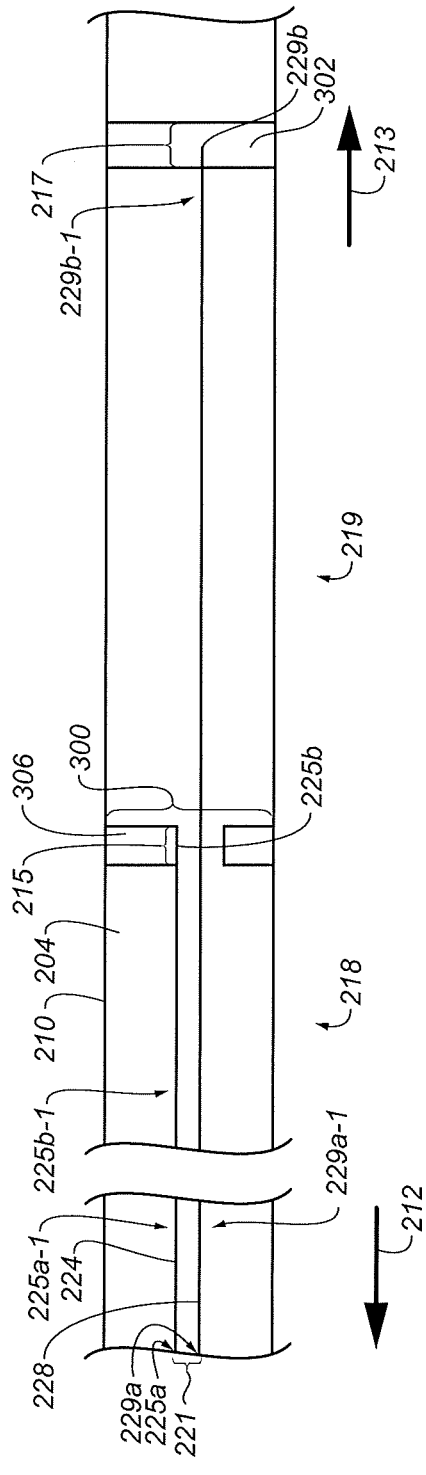

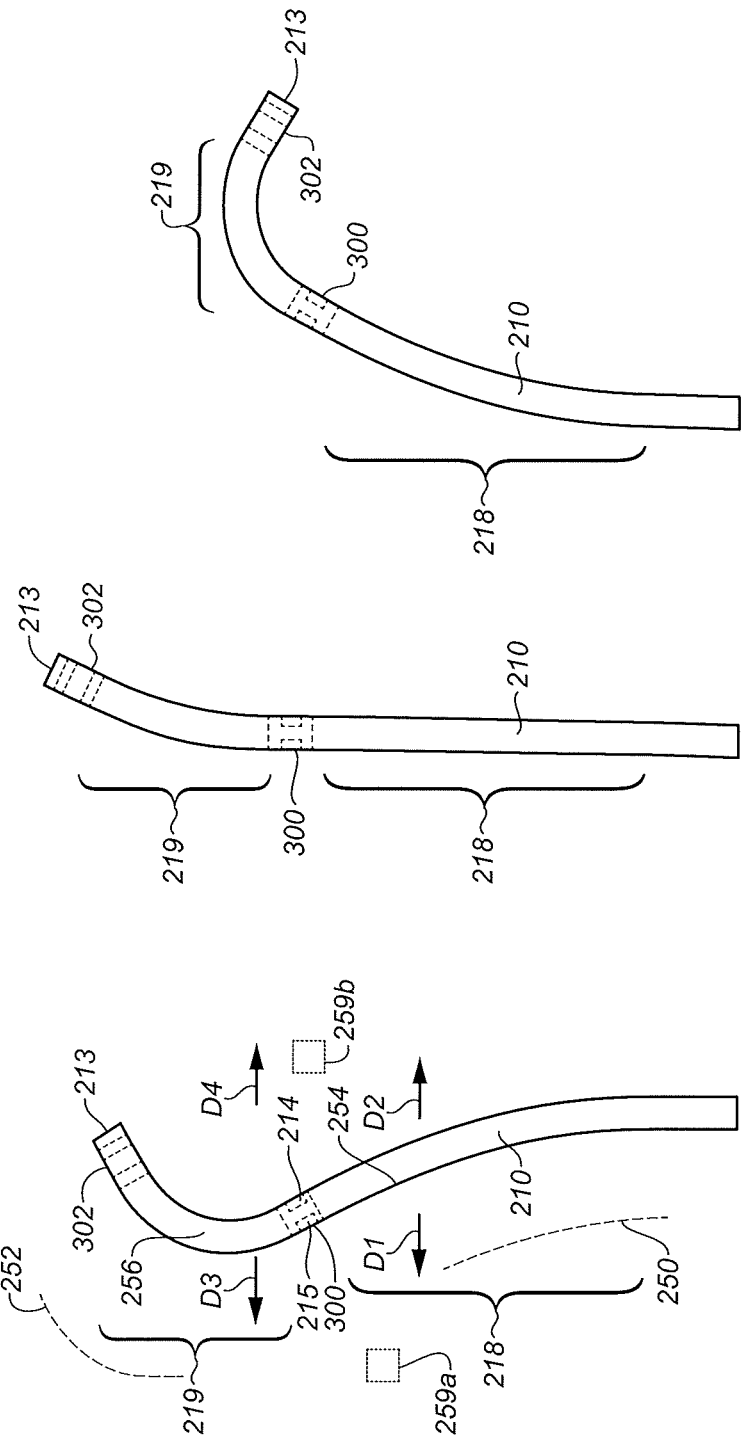

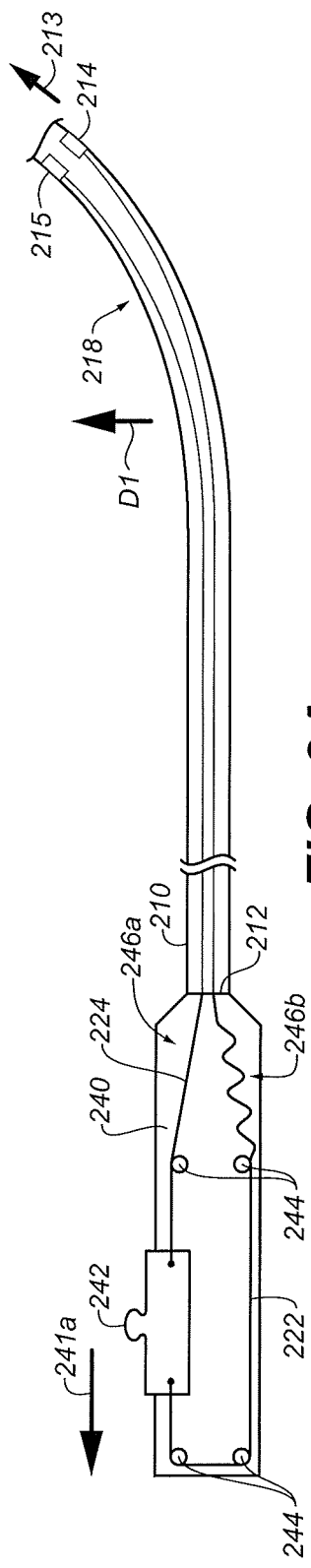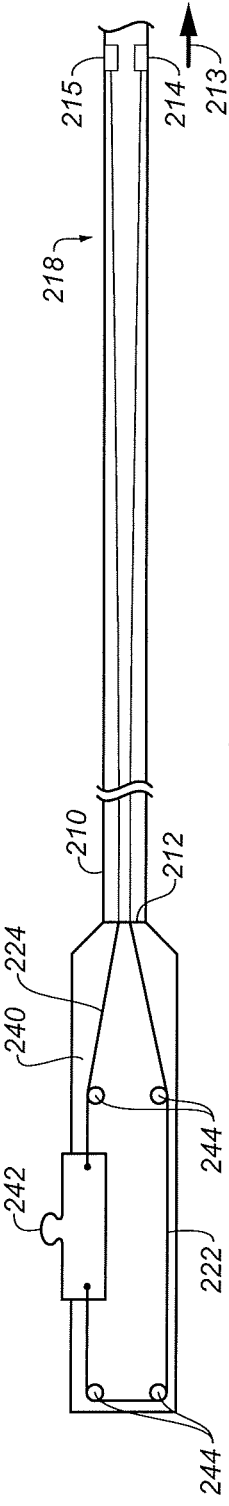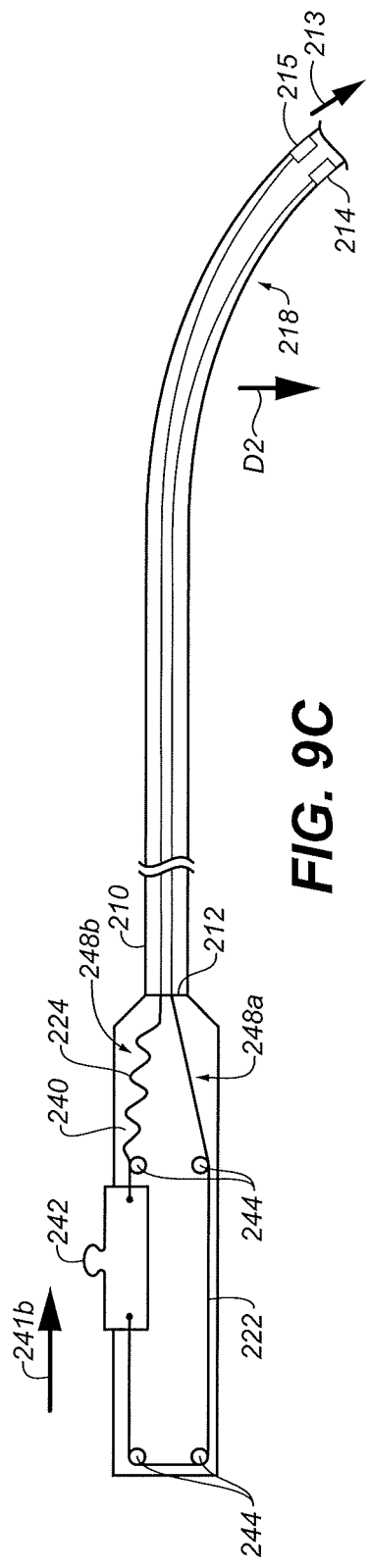
FIG. 9A
FIG. 9B
FIG. 9C

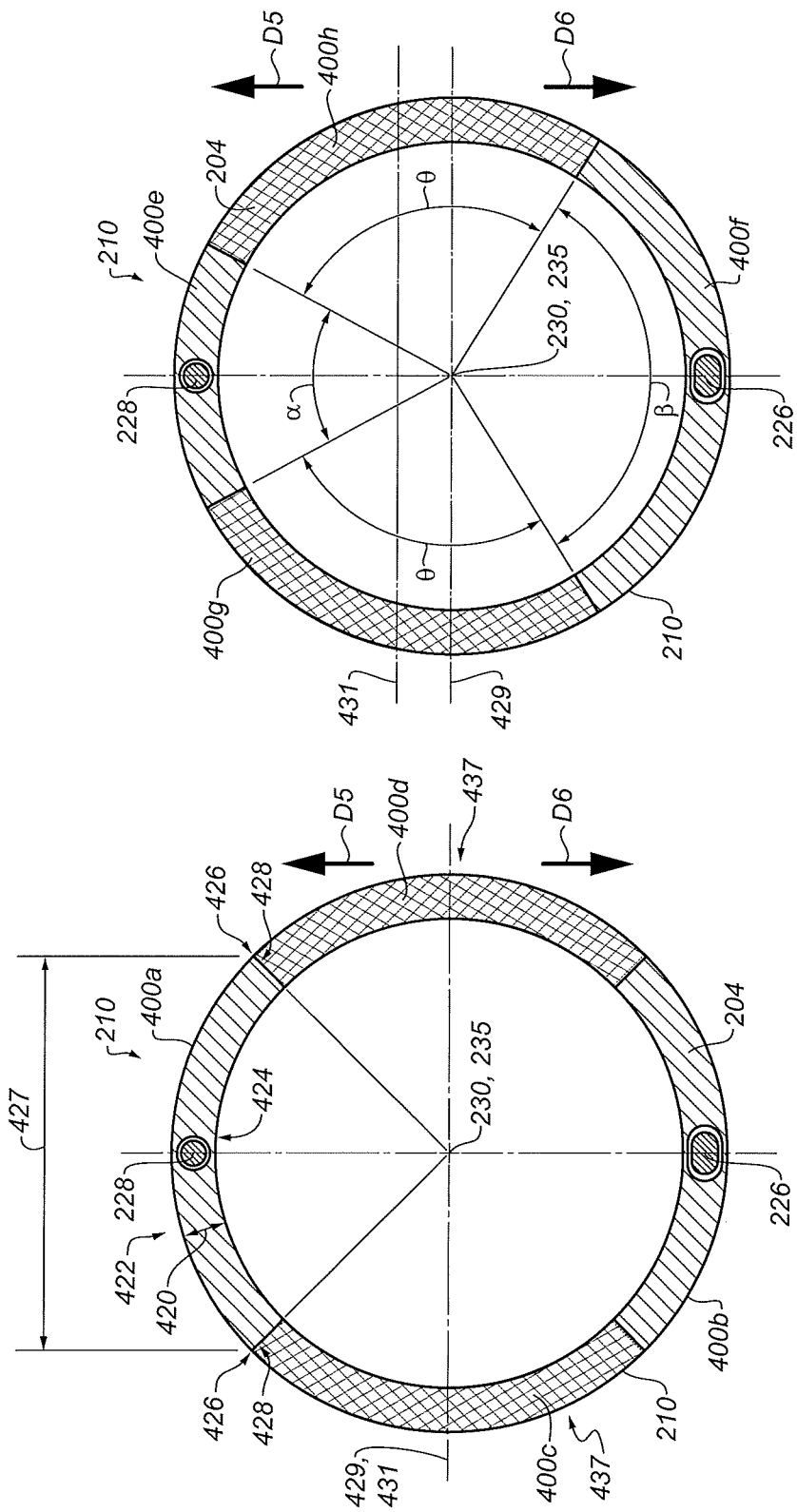

MEDICAL SYSTEM

CROSS-REFERENCE TO RELATED APPLICATION

This application is a continuation of International Application No. PCT/CA2016/000297, filed Dec. 1, 2016, which claims the benefit of U.S. Provisional Application No. 62/268,771, filed Dec. 17, 2015, the entire disclosure of both of these applications is hereby incorporated herein by reference.

TECHNICAL FIELD

Aspects of this disclosure generally are related to medical systems. In particular, aspects of this disclosure relate to medical systems that include a steerable shaft member that may be deployed through a bodily opening leading to a bodily cavity.

BACKGROUND

Cardiac surgery was initially undertaken using highly invasive open procedures. A sternotomy, which is a type of incision in the center of the chest that separates the sternum was typically employed to allow access to the heart. In the past several decades, however, more and more cardiac operations are performed using intravascular or percutaneous techniques, where access to inner organs or other tissue is gained via a catheter.

Intravascular or percutaneous surgeries benefit patients by reducing surgery risk, complications and recovery time. However, the use of intravascular or percutaneous technologies also raises some particular challenges. Medical devices used in intravascular or percutaneous surgery need to be deployed via catheter systems which significantly increase the complexity of the device structure. As well, doctors do not have direct visual contact with the medical devices once the devices are positioned within the body.

The positioning of a medical device is crucial to such procedures. For accurate positioning, a catheter system needs to be bent or steered as it is deployed through a bodily opening (e.g., an artery), and into a bodily cavity (e.g., an atrium in a heart). By way of the steering, an end of a catheter can be deflected or bent in one or another direction. The steering function can be controlled via the use of one or more steering lines positioned within the catheter. The degree and order of pulling, tensioning or taking up or playing out the steering lines controls the degree of deflection of the catheter.

Conventional catheter devices, however, have certain shortcomings. The present inventors recognized that such conventional catheter devices are limited in the amount and manner that they can be deflected or bent. The present inventors recognized that such limitations can make it difficult or impossible to position a medical device as desired within a bodily cavity. Further, the present inventors recognized that when a large amount of deflection or bending is required, conventional catheter systems may kink, or require a large longitudinal diameter, which diminishes the usefulness of the catheter device. Accordingly, a need in the art exists for improved intra-bodily cavity medical devices.

SUMMARY

At least the above-discussed need is addressed and technical solutions are achieved by various embodiments of the present invention. In some embodiments, a medical system may be summarized as including an elongate shaft member, sized for percutaneous delivery at least partially through a bodily opening to a bodily cavity, and the elongate shaft member including a first lumen. The elongate shaft member may include a plurality of steering lines, each terminated at respective locations along the elongate shaft member. According to some embodiments, the plurality of steering lines may include first and second pairs of steering lines, each steering line of the plurality of steering lines including a respective first end portion including a first end of the steering line and a respective second end portion including a second end of the steering line, the first end portion and the second end portion spaced from one another across a length of the steering line. The first pair of steering lines may include a first proximal steering line and a first distal steering line, and the second pair of steering lines may include a second proximal steering line and a second distal steering line. According to some embodiments, the respective second end portion of the first proximal steering line terminates at a first proximal termination portion of the elongate shaft member, and the respective second end portion of the first distal steering line terminates at a first distal termination portion of the elongate shaft member. According to some embodiments, the respective second end portion of the second proximal steering line terminates at a second proximal termination portion of the elongate shaft member, and the respective second end portion of the second distal steering line terminates at a second distal termination portion of the elongate shaft member. In various embodiments, the steering lines of the plurality of steering lines are operable to cause bending of the elongate shaft member via movement of at least one of the steering lines.

In some embodiments, the plurality of steering lines may be disposed within an exterior wall of the elongate shaft member.

In some embodiments, the elongate shaft member may include a proximal steering ring disposed at a proximal bending portion of the elongate shaft member, and a distal steering ring, disposed at a distal bending portion of the elongate shaft member. The respective second end portions of the first proximal steering line and the second proximal steering line may be terminated at the proximal steering ring, and the respective second end portions of the first distal steering line and the second distal steering line may be terminated at the distal steering ring according to some embodiments. In some embodiments, the proximal steering ring may include a first semi-circular ring portion and a second semi-circular ring portion, each of the first semicircular ring portion and the second semicircular ring portion including respective first and second edge portions. According to some embodiments, the respective second end portion of the first proximal steering line may terminate at the first semi-circular ring portion and the respective second end portion of the second proximal steering line may terminate at the second semi-circular ring portion. The first semi-circular ring portion and the second semi-circular ring portion may be disposed apart from each other and the respective first edge portions of the first and the second semi-circular ring portions may define a first gap and the respective second edge portions of the first and the second semi-circular ring portions may define a second gap according to some embodiments. In some embodiments, the first distal steering line may pass through the first gap, and the second distal steering line may pass through the second gap.

In some embodiments, the plurality of steering lines may be angularly spaced about a longitudinal axis of the elongate shaft member, as viewed along the longitudinal axis of the elongate shaft member. At least (a) an angular spacing between the first proximal steering line and the second distal steering line is approximately 180 degrees, or (b) an angular spacing between the second proximal steering line and the first distal steering line is approximately 180 degrees according to some embodiments. In some embodiments, the elongate shaft member includes a proximal end and a distal end, and each of the first distal termination portion of the elongate shaft member and the second distal termination portion of the elongate shaft member may be located relatively closer to the distal end of the elongate shaft member than each of the first proximal termination portion of the elongate shaft member and the second proximal termination portion of the elongate shaft member. In some embodiments, the elongate shaft member permits opposing movement of the first proximal steering line and the second proximal steering line to bend a proximal bending portion of the elongate shaft member in a first direction of two opposing directions within a first plane, and permits opposing movement of the first proximal steering line and the second proximal steering line to bend the proximal bending portion of the elongate shaft member in a second direction of the two opposing directions within the first plane, the second direction of the two opposing directions within the first plane opposite to the first direction of the two opposing directions within the first plane. In some embodiments, the elongate shaft member permits opposing movement of the first distal steering line and the second distal steering line to bend a distal bending portion of the elongate shaft member in a first direction of two opposing directions within a second plane, and permits opposing movement of the first distal steering line and the second distal steering line to bend the distal bending portion of the elongate shaft member in a second direction of the two opposing directions within the second plane, the second direction of the two opposing directions within the second plane opposite to the first direction of the two opposing directions within the second plane.

In some embodiments, the plurality of steering lines may be arranged in an arrangement in which the plurality of steering lines are angularly arranged about a longitudinal axis of the elongate shaft member, as viewed along the longitudinal axis. An angular spacing between the steering lines of a first adjacent pair of the steering lines in the arrangement may be different than an angular spacing between the steering lines of a second adjacent pair of the steering lines in the arrangement according to some embodiments. In some embodiments, the first adjacent pair of the steering lines may be provided by the first proximal steering line and the first distal steering line, and the second adjacent pair of the steering lines may be provided by (a) the first proximal steering line and one of the second proximal steering line and the second distal steering line, or (b) the first distal steering line and one of the second proximal steering line and the second distal steering line. In some embodiments, the angular spacing between the steering lines of the first adjacent pair of the steering lines may be smaller than the angular spacing between the steering lines of the second adjacent pair of the steering lines.

In some embodiments, the plurality of steering lines may be angularly arranged about a longitudinal axis of the elongate shaft member, as viewed along the longitudinal axis, and at least (a) an angular spacing between the first proximal steering line and the first distal steering line may be less than 80 degrees, or (b) an angular spacing between the second proximal steering line and the second distal steering line may be less than 80 degrees.

In some embodiments, the elongate shaft member may permit a set of the plurality of steering lines to be moved to cause a first portion of a projected outline of the elongate shaft member to include a first curve and a second portion of the projected outline to include a second curve. The first curve is concave toward a first region of space, and the second curve is convex toward the first region of space according to some embodiments. In some embodiments, the first curve of the projected outline corresponds to a first curve segment of the elongate shaft member, and the second curve of the projected outline corresponds to a second curve segment of the elongate shaft member. The first curve segment and the second curve segment may be within a same plane according to some embodiments. According to some embodiments, the first curve segment may be located proximal at least (a) the first proximal termination portion of the elongate shaft member or (b) the second proximal termination portion of the elongate shaft member, and the second curve segment may be located distal at least (a) or (b).

In some embodiments, the elongate shaft member includes a proximal end and a distal end, and the elongate shaft member may permit a set of the plurality of steering lines to be moved to cause a proximal bending portion of the elongate shaft member to include a first curve segment and a distal bending portion of the elongate shaft member to include a second curve segment, the distal bending portion of the elongate shaft member positioned relatively closer to the distal end of the elongate shaft member than the proximal bending portion of the elongate shaft member. In some embodiments, the first curve segment may be concave toward a first region of space and the second curve segment may be convex toward the first region of space. In some embodiments, each of the first distal termination portion of the elongate shaft member and the second distal termination portion of the elongate shaft member may be located relatively closer to the distal end of the elongate shaft member than each of the first proximal termination portion of the elongate shaft member and the second proximal termination portion of the elongate shaft member. In some embodiments, the proximal bending portion may be positioned proximal at least (a) the first proximal termination portion of the elongate shaft member or (b) the second proximal termination portion of the elongate shaft member, and the distal bending portion of the elongate shaft member may be located distal at least (a) or (b). In some embodiments, the first curve segment and the second curve segment may be within a same plane. In some embodiments, the first curve segment and the second curve segment are located within a same plane, and the first curve segment may be located proximal at least (a) the first proximal termination portion of the shaft member or (b) the second proximal termination portion of the elongate shaft member, and the second curve segment may be located distal at least (a) or (b).

In some embodiments, the elongate shaft member includes a proximal end and a distal end, and the elongate shaft member may permit a set of the plurality of steering lines to be moved to cause a proximal bending portion of the elongate shaft member to include a first curve segment and a distal bending portion of the elongate shaft member to include a second curve segment, the distal bending portion of the elongate shaft member positioned relatively closer to the distal end of the elongate shaft member than the proximal bending portion of the elongate shaft member. In some embodiments, the first curve segment may be concave toward a first region of space and the second curve segment may be convex toward the first region of space. In some embodiments, the first curve segment may be located proximal at least (a) the first proximal termination portion of the elongate shaft member or (b) the second proximal termination portion of the elongate shaft member, and the second curve segment may be located distal at least (a) or (b).

In some embodiments, the elongate shaft member includes a proximal end and a distal end, and the elongate shaft member may permit a set of the plurality of steering lines to be moved to cause a proximal bending portion of the elongate shaft member to include a first curve segment and a distal bending portion of the elongate shaft member to include a second curve segment, the distal bending portion of the elongate shaft member positioned relatively closer to the distal end of the elongate shaft member than the proximal bending portion of the elongate shaft member. In some embodiments, the first curve segment may be concave toward a first region of space and the second curve segment may be convex toward the first region of space. In some embodiments, the elongate shaft member may include a first set of one or more materials and a second set of one or more materials, a hardness of each material in the first set of one or more materials being greater than a hardness of each material in the second set of one or more materials. According to various embodiments, the elongate shaft member may include a plurality of elongate strips, a length of each of the plurality of elongate strips being shorter than a length of the elongate shaft member between the proximal and distal ends of the elongate shaft member. In some embodiments, each elongate strip of the plurality of elongate strips includes at least one material from one of the first set of one or more materials and the second set of one or more materials but does not include a material from the other of the first set of one or more materials and the second set of one or more materials. The plurality of elongate strips include at least one material from the first set of one or more materials and at least one material from the second set of one or more materials according to various embodiments. In some embodiments, a first elongate strip of the plurality of elongate strips may include a material from the first set of one or more materials, the first elongate strip located at a convex side of the proximal bending portion of the elongate shaft member, and a second elongate strip of the plurality of elongate strips may include a material from the second set of one or more materials, the second elongate strip located at a concave side of the distal bending portion of the elongate shaft member. In some embodiments, at least (a) the first set of one or more materials may include one or more polymer materials or (b) the second set of one or more materials may include one or more polymer materials. In some embodiments, the proximal bending portion may be located proximal at least (a) the first proximal termination portion or (b) the second proximal termination portion, and the distal bending portion may be located distal at least (a) or (b). In some embodiments, a third elongate strip of the plurality of elongate strips may include a material from the second set of one or more materials, the third elongate strip located at a concave side of the proximal bending portion of the elongate shaft member. In some embodiments, a fourth elongate strip of the plurality of elongate strips may include a material from the second set of one or more materials, the fourth elongate strip located at a convex side of the distal bending portion of the elongate shaft member. In some embodiments, at least (a) the first elongate strip of the plurality of elongate strips may include a polymer material, (b) the second elongate strip of the plurality of elongate strips may include a polymer material, (c) the third elongate strip of the plurality of elongate strips may include a polymer material or (d) the fourth elongate strip of the plurality of elongate strips may include a polymer material.

Each elongate strip of the plurality of elongate strips may include a thickness, a front surface facing radially outwardly from a longitudinal axis of the elongate shaft member, a back surface opposite across the thickness from the front surface, and a respective pair of side edges that define a portion of a periphery of at least one of the front surface and the back surface, the side edges of each pair of side edges opposed to one another across at least a portion of the length of the elongate strip, the elongate strip including a width between each pair of side edges. The width of each of the plurality of elongate strips may be smaller than a circumference of the elongate shaft member according to some embodiments.

In some embodiments, a respective cross-section of at least the first elongate strip or the second elongate strip may include a sector-shaped profile when viewed along a longitudinal axis of the elongate shaft member, each sector-shaped profile subtending an angle less than 360 degrees.

In some embodiments, the elongate shaft member includes a proximal end and a distal end, and the elongate shaft member may include a proximal bending portion and a distal bending portion, the distal bending portion of the elongate shaft member positioned relatively closer to the distal end of the elongate shaft member than the proximal bending portion of the elongate shaft member. In some embodiments, the proximal bending portion may be bendable in two opposing directions within a first plane, in response to movement of at least a first set of the plurality of steering lines, and the distal bending portion may be bendable in two opposing directions within a second plane, in response to movement of at least a second set of the plurality of steering lines.

In some embodiments, a first group of materials may be distributed in the proximal bending portion to resist bending, in response to movement of the first set of the plurality of steering lines, of the proximal bending portion in one of a first direction of the two opposing directions within the first plane with a greater resistance than in bending, in response to movement of the first set of the plurality of steering lines, of the proximal bending portion in a second direction of the two opposing directions within the first plane, the second direction of the two opposing directions within the first plane opposite to the first direction of the two opposing directions within the first plane. In some embodiments, a second group of materials may be distributed in the distal bending portion to resist bending, in response to movement of the second set of the plurality of steering lines, of the distal bending portion in a first direction of the two opposing directions within the second plane with a greater resistance than in bending, in response to movement of the second set of the plurality of steering lines, of the distal bending portion in a second direction of the two opposing directions within the second plane, the second direction of the two opposing directions within the second plane opposite to the first direction of the two opposing directions within the second plane. In various embodiments, each of the first group of materials and the second group of materials may include materials having different hardnesses. In some embodiments, at least the first group of materials may include one or more polymer materials or the second group of materials may include one or more polymer materials.

In some embodiments, the elongate shaft member permits opposing movement of the first proximal steering line and the second proximal steering line to bend the proximal bending portion of the elongate shaft member in the first direction of two opposing directions within the first plane, and permits opposing movement of the first proximal steering line and the second proximal steering line to bend the proximal bending portion of the elongate shaft member in the second direction of the two opposing directions within the first plane. In some embodiments, the elongate shaft member permits opposing movement of the first distal steering line and the second distal steering line to bend the distal bending portion of the elongate shaft member in the first direction of two opposing directions within the second plane, and permits opposing movement of the first distal steering line and the second distal steering line to bend the distal bending portion of the elongate shaft member in the second direction of the two opposing directions within the second plane. In some embodiments, the proximal bending portion may be located proximal at least (a) the first proximal termination portion or (b) the second proximal termination portion, and the distal bending portion may be located distal at least (a) or (b).

In some embodiments, the elongate shaft member includes a proximal end and a distal end, and the elongate shaft member may include a proximal bending portion and a distal bending portion, the distal bending portion of the elongate shaft member positioned relatively closer to the distal end of the elongate shaft member than the proximal bending portion of the elongate shaft member. In some embodiments, the elongate shaft member may include a first set of one or more materials and a second set of one or more materials, a hardness of each material in the first set of one or more materials being greater than a hardness of each material in the second set of one or more materials. In some embodiments, the elongate shaft member may include a plurality of elongate strips, a length of each of the plurality of elongate strips being shorter than a length of the elongate shaft member between the proximal and distal ends of the elongate shaft member. In various embodiments, each elongate strip of the plurality of elongate strips includes at least one material from one of the first set of one or more materials and the second set of one or more materials but does not include a material from the other of the first set of one or more materials and the second set of one or more materials. In some embodiments, each of the proximal bending portion and the distal bending portion may include a respective group of the elongate strips angularly arrayed about a longitudinal axis of the elongate shaft member, and for each respective group of the elongate strips, at least a first elongate strip of the respective group of the elongate strips includes a material from the first set of one or more materials, and at least a second elongate strip of the respective group of the elongate strips includes a material from the second set of one or more materials. In some embodiments, at least (a) the first set of one or more materials may include one or more polymer materials or (b) the second set of one or more materials may include one or more polymer materials.

In some embodiments, the respective group of the elongate strips of the proximal bending portion may include a different number of the elongate strips than a number of the elongate strips comprised by the respective group of the elongate strips of the distal bending portion. In some embodiments, the respective group of the elongate strips of the proximal bending portion includes a first number of particular ones of the elongate strips each including a material from the first set of one or more materials, and the respective group of the elongate strips of the distal bending portion includes a second number of particular ones of the elongate strips each including a material from the first set of one or more materials, the first number being different from the second number. In some embodiments, the respective group of the elongate strips of the proximal bending portion includes a first number of particular ones of the elongate strips each including a material from the second set of one or more materials, and the respective group of the elongate strips of the distal bending portion includes a second number of particular ones of the elongate strips each including a material from the second set of one or more materials, the first number being different from the second number. In some embodiments, for each respective group of at least one of the respective groups of the elongate strips, a number of particular ones of the elongate members of the respective group each including a material from the first set of one or more materials is the same as a number of particular ones of the elongate members of the respective group each including a material from the second set of one or more materials. In some embodiments, for each respective group of at least one of the respective groups of the elongate strips, a number of particular ones of the elongate members of the respective group each including a material from the first set of one or more materials is different than a number of particular ones of the elongate members of the respective group each including a material from the second set of one or more materials. In some embodiments, the elongate strips of each respective group of the elongate strips may be disposed at a position distanced apart from a geometric center of the elongate shaft member, when viewed along the longitudinal axis of the elongate shaft member. In some embodiments, the proximal bending portion may be located proximal at least (a) the first proximal termination portion or (b) the second proximal termination portion, and the distal bending portion may be located distal at least (a) or (b).

In some embodiments, the elongate shaft member includes a proximal end and a distal end, and the elongate shaft member may include a proximal bending portion and a distal bending portion, the distal bending portion located closer to the distal end of the elongate shaft member than the proximal bending portion. In some embodiments, the elongate shaft member may include a first material and a second material, a hardness of the first material being greater than a hardness of the second material. In some embodiments, each of the proximal bending portion and the distal bending portion includes the first material and the second material, and a spatial distribution between the first material and the second material in the proximal bending portion may be different than a spatial distribution between the first material and the second material in the distal bending portion. In various embodiments, at least the first material may be a polymer material or the second material may be a polymer material. In some embodiments, the proximal bending portion may be located proximal at least (a) the first proximal termination portion or (b) the second proximal termination portion, and the distal bending portion may be located distal at least (a) or (b).

In some embodiments, the elongate shaft member may include at least a first material and a second material, a hardness of the first material being greater than a hardness of the second material. According to various embodiments, the first material and the second material may be distributed in the elongate shaft member to provide an off-center neutral axis of the elongate shaft member with respect to a longitudinal axis of the elongate shaft member that passes through a geometric center of a cross-section of the elongate shaft member, the cross-section transverse to the longitudinal axis. In some embodiments, at least the first material may be a polymer material or the second material may be a polymer material.

In some embodiments, the elongate shaft member includes a proximal end and a distal end, and the elongate shaft member may include a proximal bending portion and a distal bending portion, the distal bending portion located closer to the distal end of the elongate shaft member than the proximal bending portion. In some embodiments, the elongate shaft member may include at least a first material, a second material, a third material and a fourth material. According to various embodiments, a hardness of the first material may be greater than a hardness of the second material, and a hardness of the third material may be greater than a hardness of the fourth material. In some embodiments, a first distribution of the first material and the second material may exist in the proximal bending portion to provide an off-center neutral axis of the proximal bending portion with respect to a longitudinal axis of the elongate shaft member that passes through a geometric center of a cross-section of the elongate shaft member, the cross-section transverse to the longitudinal axis. In some embodiments, a second distribution of the third material and the fourth material may exist in the distal bending portion to provide an off-center neutral axis of the distal bending portion with respect to the longitudinal axis of the elongate shaft member that passes through the geometric center of the cross-section of the elongate shaft member. According to various embodiments, a location of the off-center neutral axis of the distal bending portion as viewed along a part of the longitudinal axis of the elongate shaft member extending through the distal bending portion may be different than a location of the off-center neutral axis of the proximal bending portion as viewed along a part of the longitudinal axis of the elongate shaft member extending through the proximal bending portion.

In some embodiments, the off-center neutral axis of the proximal bending portion and the off-center neutral axis of the distal bending portion are on opposite sides of the longitudinal axis as viewed along a direction of the longitudinal axis. In some embodiments, the off-center neutral axis of the proximal bending portion and the off-center neutral axis of the distal bending portion may be parallel to one another. In some embodiments, the off-center neutral axis of the proximal bending portion and the off-center neutral axis of the distal bending portion may correspond to a bending of each of the proximal bending portion and the distal bending portion within a same plane. In some embodiments, at least (a) the first material may include a polymer material, (b) the second material may include a polymer material, (c) the third material may include a polymer material or (d) the fourth material may include a polymer material. In some embodiments, the proximal bending portion may be located proximal at least (a) the first proximal termination portion or (b) the second proximal termination portion, and the distal bending portion may be located distal at least (a) or (b). In some embodiments, each of the first material and the second material may be different than at least one of the third material and the fourth material.

In some embodiments, each respective steering line of the plurality of steering lines includes a respective cross-sectional area when viewed in a direction along a respective longitudinal axis of the respective steering line, the respective cross-sectional area transverse to the respective longitudinal axis. In some embodiments, the respective cross-sectional area of the first proximal steering line may be different than the respective cross-sectional area of the first distal steering line. In some embodiments, the respective cross-sectional area of the first distal steering line may be greater than at least the respective cross-sectional area of (a) the first proximal steering line or (b) the second proximal steering line, or (c) the second distal steering line.

In some embodiments, the elongate shaft member is an elongate sheath, the elongate sheath including a lumen sized to selectively allow passage of a medical instrument therethrough during percutaneous delivery of the medical instrument along a path through the lumen. In some embodiments, the medical system may further include an expandable structure coupled to an end of the elongate shaft member.

Various systems may include combinations and subsets of all the systems summarized above.

In some embodiments, a medical system may be summarized as including a handle, and an elongate shaft member coupled to the handle, the elongate shaft member sized for percutaneous delivery at least partially through a bodily opening to a bodily cavity, and including a proximal end, a distal end, at least one lumen extending between the proximal end and the distal end, and a longitudinal axis extending between the proximal end and the distal end. In some embodiments, the elongate shaft member may include a first set of one or more materials and a second set of one or more materials, a hardness of each material in the first set of one or more materials is greater than a hardness of each material in the second set of one or more materials according to some embodiments. In some embodiments, the elongate shaft member may include a first bendable portion located between the proximal end and the distal end, the first bendable portion including a plurality of elongate strips angularly arranged about a portion of the longitudinal axis extending through the first bendable portion, each of the plurality of elongate strips including a first end, a second end, and a length between the first end and the second end, the length of each of the plurality of elongate strips being shorter than a length of the elongate shaft member between the proximal and distal ends of the elongate shaft member. Each elongate strip of the plurality of elongate strips includes at least one material from one of the first set of one or more materials and the second set of one or more materials but does not include a material from the other of the first set of one or more materials and the second set of one or more materials according to various embodiments. The plurality of elongate strips include at least one material in the first set of one or more materials and at least one material in the second set of one or more materials according to various embodiments.

In some embodiments, the first bendable portion is bendable in at least two opposing directions. In some embodiments, the plurality of elongate strips may include three or more elongate strips. In some embodiments, a number of particular ones of the plurality of elongate strips that each includes a material in the first set of one or more materials may be different than a number of particular ones of the plurality of elongate strips that each includes a material in the second set of one or more materials. In some embodiments, a first particular one of the plurality of elongate strips including a material in the first set of one or more materials may be axially offset along the portion of the longitudinal axis from a second particular one of the plurality of elongate strips including a material in the second set of one or more materials. In some embodiments, a first particular one of the plurality of elongate strips including a material in the first set of one or more materials may be axially spaced along the portion of the longitudinal axis from a second particular one of the plurality of elongate strips including a material in the second set of one or more materials.

In some embodiments, a cross-section of each of the plurality of elongate strips may include a respective sector-shaped profile when viewed along the portion of the longitudinal axis of the elongate shaft member, each respective sector-shaped profile subtending an angular amount less than 360 degrees. In some embodiments, the sector-shaped profiles of at least two particular ones of the plurality of elongate strips that each respectively includes a material in the first set of the one or more materials may subtend different angular amounts. In some embodiments, the sector-shaped profiles of at least two particular ones of the plurality of elongate strips that each respectively includes a material in the second set of the one or more materials may subtend different angular amounts. In some embodiments, the respective sector-shaped profile of a particular one of the plurality of elongate strips including a material in the first set of one or more materials and the respective sector-shaped profile of a particular one of the plurality of elongate strips including a material in the second set of one or more materials subtend different angular amounts.

In some embodiments, the medical system may further include at least a first steering line terminated at a location between a first particular elongate strip including a material in the first set of one or more materials and a second particular elongate strip including a material in the second set of one or more materials, the first steering line being operable to cause bending of at least part of the first bendable portion via movement of the first steering line. In some embodiments, the medical system may include at least a first steering line terminated at a location axially along the elongate shaft member between a first group of the plurality of elongate strips and a second group of the plurality of elongate strips, each of the first group of the plurality of elongate strips and the second group of the plurality of elongate strips respectively including at least one material in the first set of one or more materials and at least one material in the second set of one or more materials, the first steering line being operable to cause bending of at least part of the first bendable portion via movement of the first steering line.

In some embodiments, a first group of the plurality of elongate strips are angularly arrayed about the longitudinal axis at a first location on the portion of the longitudinal axis, and a second group of the plurality of elongate strips are angularly arrayed about the longitudinal axis at a second location on the portion of the longitudinal axis spaced from the first location, each of the first group of the plurality of elongate strips and the second group of the plurality of elongate strips including at least one respective particular of one of the plurality of elongate strips including a material in the first set of one or more materials and at least one respective particular one of the plurality of elongate strips including a material in the second set of one or more materials. The first group of the plurality of elongate strips includes different elongate strips than the second group of the plurality of elongate strips according to various embodiments. In the some embodiments, the total number of elongate strips in the first group of the plurality of elongate strips is different than the total number of elongate strips in the second group of the plurality of elongate strips. In some embodiments, the total number of particular ones of the elongate strips in the first group of the plurality of elongate strips that each includes a material in the first set of one or more materials is different than the total number of particular ones of the elongate strips in the second group of the plurality of elongate strips that each includes a material in the first set of one or more materials. In some embodiments, the total number of particular ones of the elongate strips in the first group of the plurality of elongate strips that each includes a material in the second set of one or more materials is different than the total number of particular ones of the elongate strips in the second group of the plurality of elongate strips that each includes a material in the second set of one or more materials.

In some embodiments, the elongate shaft member may include a second bendable portion located between the proximal end and the distal end. In some embodiments, the elongate shaft member may be an elongate sheath, the elongate sheath including a lumen sized to selectively allow passage of a medical instrument therethrough during percutaneous delivery of the medical instrument along a path through the lumen. In some embodiments, at least (a) the first set of one or more materials may include one or more polymer materials or (b) the second set of one or more materials may include one or more polymer materials. In some embodiments, the medical system includes an expandable structure coupled to an end of the elongate shaft member.

Various systems may include combinations and subsets of all the systems summarized above.

In some embodiments, a medical system may be summarized as including a handle, and an elongate shaft member coupled to the handle, the elongate shaft member sized for percutaneous delivery at least partially through a bodily opening to a bodily cavity, and including a proximal end, a distal end, at least one lumen extending between the proximal end and the distal end, and a longitudinal axis extending between the proximal end and the distal end. In various embodiments, the elongate shaft member may include a first set of one or more materials and a second set of one or more materials, a hardness of each material in the first set of one or more materials being greater than a hardness of each material in the second set of one or more materials. In various embodiments, the elongate shaft member may include a first bendable portion located between the proximal end and the distal end, the first bendable portion including a plurality of elongate strips angularly arranged in an angular arrangement about a portion of the longitudinal axis extending through the first bendable portion, each of the plurality of elongate strips including a first end, a second end, and a length between the first end and the second end, the length of each of the plurality of elongate strips being shorter than a length of the elongate shaft member between the proximal and distal ends of the elongate shaft member. Each of a first elongate strip of the plurality of elongate strips and a second elongate strip of the plurality of elongate strips may include at least one material from the first set of one or more materials according to various embodiments. Each of a third elongate strip of the plurality of elongate strips and a fourth elongate strip of the plurality of elongate strips may include at least one material from the second set of one or more materials according to various embodiments. In some embodiments, the angular arrangement may at least include (a) at least a portion of the first elongate strip located 180 degrees about the portion of the longitudinal axis from at least a portion of the second elongate strip, or (b) at least a portion of the third elongate strip located 180 degrees about the portion of the longitudinal axis from at least a portion of the fourth elongate strip.

Various systems may include combinations and subsets of all the systems summarized above.

BRIEF DESCRIPTION OF THE DRAWINGS

It is to be understood that the attached drawings are for purposes of illustrating aspects of various embodiments and may include elements that are not to scale.

FIGS. 3A and 3B are partial cutaway representations of an elongated shaft member of a medical system, according to various example embodiments.

FIGS. 8A, 8B, and 8C are elevation views of an elongate shaft member in various bending configurations, according to example embodiments.

FIGS. 9A, 9B, and 9C illustrate an elongate shaft member in various bending shapes, according to example embodiments.

FIGS. 10A, 10B, 10C, 11, and 12 show views of example embodiments of an elongate shaft member formed of materials having different degrees of hardness or bending stiffness.

DETAILED DESCRIPTION

Figure 1:
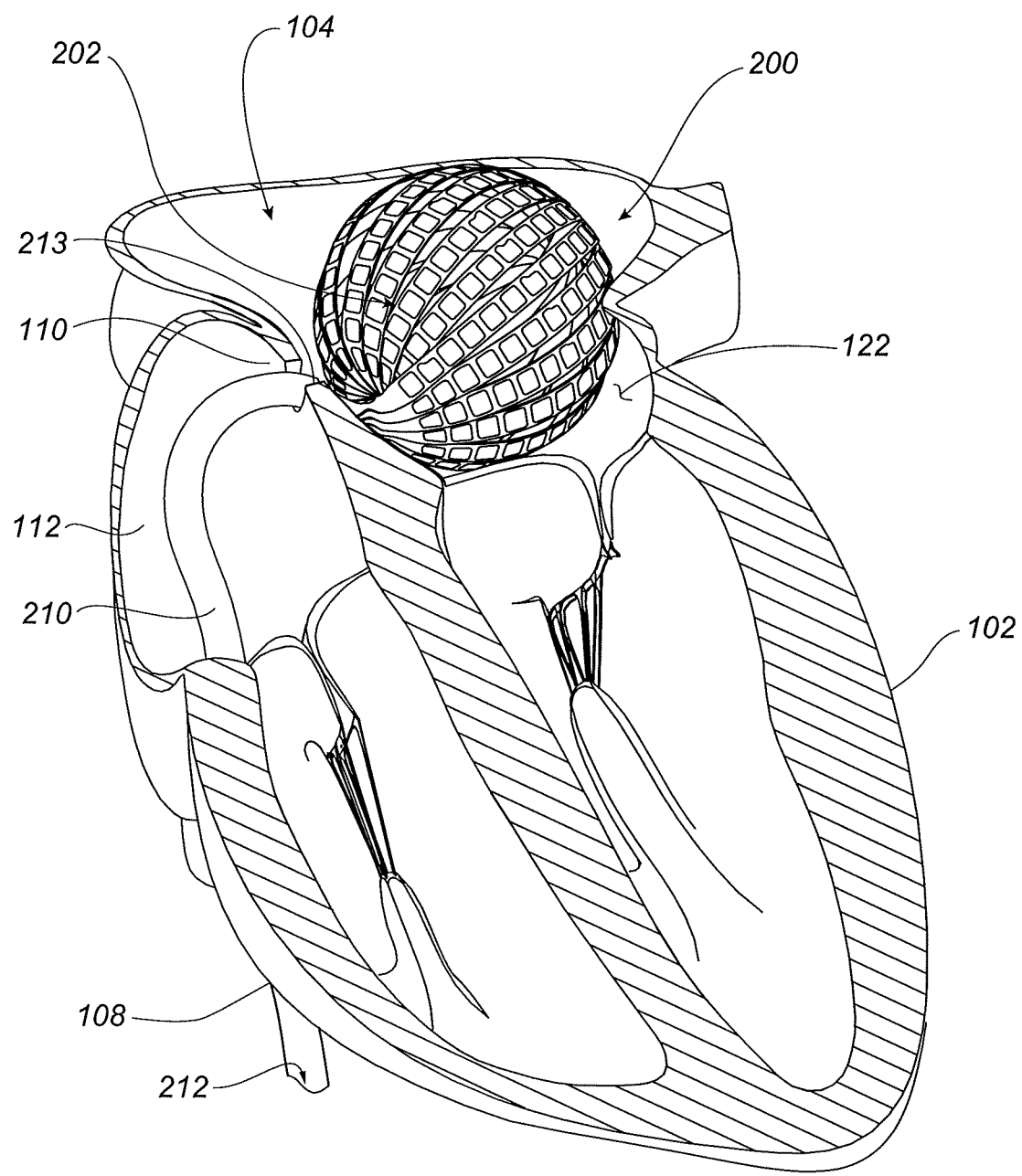
FIG. 1 is a cutaway diagram of a heart showing a medical system including an elongate shaft member coupled to an expandable structure percutaneously placed in a left atrium of the heart, according to various example embodiments.

Various embodiments disclosed herein provide improved medical device systems that include various termination locations of steering lines and various distributions of materials (e.g., polymer materials) differing in hardness to provide an elongate shaft member of a medical device system exhibiting improved bendability and positioning with respect to particular anatomical features that improves desired placement of an operative structure delivered by the elongate shaft member within a bodily cavity to treat the bodily cavity, while retaining a diameter of the elongate shaft member that is suitable at least for percutaneous delivery. It should be noted that the invention is not limited to these or any other examples provided herein, which are referred to for purposes of illustration only.

In the following description, certain specific details are set forth in order to provide a thorough understanding of various embodiments of the invention. However, one skilled in the art will understand that the invention may be practiced at a more general level without one or more of these details. In other instances, well-known structures (e.g., structures associated with medical systems and catheters) have not been shown or described in detail to avoid unnecessarily obscuring descriptions of various embodiments of the invention.

Any reference throughout this specification to "one embodiment" or "an embodiment" or "an example embodiment" or "an illustrated embodiment" or "a particular embodiment" and the like means that a particular feature, structure or characteristic described in connection with the embodiment is included in at least one embodiment. Thus, any appearance of the phrase "in one embodiment" or "in an embodiment" or "in an example embodiment" or "in this illustrated embodiment" or "in this particular embodiment" or the like in this specification is not necessarily referring to one embodiment or a same embodiment. Furthermore, the particular features, structures or characteristics of different embodiments may be combined in any suitable manner to form one or more other embodiments.

Unless otherwise explicitly noted or required by context, the word "or" is used in this disclosure in a non-exclusive sense. In addition, unless otherwise explicitly noted or required by context, the word "set" is intended to mean one or more, and the word "subset" is intended to mean a set having the same or fewer elements of those present in the subset's parent or superset.

Further, the phrase "at least" is or may be used herein at times merely to emphasize the possibility that other elements may exist besides those explicitly listed. However, unless otherwise explicitly noted (such as by the use of the term "only") or required by context, non-usage herein of the phrase "at least" nonetheless includes the possibility that other elements may exist besides those explicitly listed. For example, the phrase 'based at least on A' includes A as well as the possibility of one or more other additional elements besides A. In the same manner, the phrase 'based on A' includes A, as well as the possibility of one or more other additional elements besides A. However, the phrase 'based only on A' includes only A. Similarly, the phrase 'configured at least to A' includes a configuration to perform A, as well as the possibility of one or more other additional actions besides A. In the same manner, the phrase 'configured to A' includes a configuration to perform A, as well as the possibility of one or more other additional actions besides A. However, the phrase 'configured only to A' means a configuration to perform only A.

The word "device", the word "machine", and the phrase "device system" all are intended to include one or more physical devices or sub-devices (e.g., pieces of equipment) that interact to perform one or more functions, regardless of whether such devices or sub-devices are located within a same housing or different housings. However, it may be explicitly specified that a device or machine or device system reside entirely within a same housing to exclude embodiments where the respective device, machine, or device system reside across different housings. The word "device" may equivalently be referred to as a "device system".

Further, the phrase "in response to" may be used in this disclosure. For example, this phrase might be used in the following context, where an event A occurs in response to the occurrence of an event B. In this regard, such phrase includes, for example, that at least the occurrence of the event B causes or triggers the event A.

In some embodiments, the term "adjacent", the term "proximate", or the like refers at least to a sufficient closeness between the objects defined as adjacent, proximate, or the like, to allow the objects to interact in a designated way. For example, if object A performs an action on an adjacent or proximate object B, objects A and B would have at least a sufficient closeness to allow object A to perform the action on object B. In this regard, some actions may require contact between the associated objects, such that if object A performs such an action on an adjacent or proximate object B, objects A and B would be in contact, for example, in some instances or embodiments where object A needs to be in contact with object B to successfully perform the action. In some embodiments, the term "adjacent", the term "proximate", or the like additionally or alternatively refers to objects that do not have another substantially similar object between them. For example, object A and object B could be considered adjacent or proximate if they contact each other (and, thus, it could be considered that no other object is between them), or if they do not contact each other but no other object that is substantially similar to object A, object B, or both objects A and B, depending on the embodiment, is between them. In some embodiments, the term "adjacent", the term "proximate", or the like additionally or alternatively refers to at least a sufficient closeness between the objects defined as adjacent, proximate, or the like, the sufficient closeness being within a range that does not place any one or more of the objects into a different or dissimilar region, or does not change an intended function of any one or more of the objects or of an encompassing object that includes a set of the objects. Different embodiments of the present invention adopt different ones or combinations of the above definitions. Of course, however, the term "adjacent", the term "proximate", or the like is not limited to any of the above example definitions, according to some embodiments. In addition, the term "adjacent" and the term "proximate" do not have the same definition, according to some embodiments.

FIG. 1 is a medical system 200 including an expandable structure 202 percutaneously or intravascularly placed in a left atrium 104 of a heart 102, according to some embodiments. Expandable structure 202 can be percutaneously or intravascularly inserted into a portion of the heart 102, such as an intra-cardiac cavity, like left atrium 104. In this example, the expandable structure 202 is physically coupled to an end of an elongate shaft member 210 inserted via the inferior vena cava 108 and penetrating through a bodily opening in transatrial septum 110 from right atrium 112. In other embodiments, other paths may be taken. In some embodiments, the elongate shaft member 210 may be part of a catheter. The elongate shaft member 210 is flexible and appropriately sized to be delivered, at least in part, percutaneously or intravascularly. In some embodiments, at least part of the elongate shaft member is delivered though a natural bodily opening. Various portions of elongate shaft member 210 may be steerable.

In some embodiments, expandable structure 202 assumes an unexpanded configuration for delivery to left atrium 104. Expandable structure 202 can then be selectively expanded upon delivery to left atrium 104 to position certain portions of the expandable structure 202 proximate the interior surface formed by tissue 122 of left atrium 104 in order to, for example, sense characteristics of, ablate, or otherwise interact with or treat such tissue 122.

Figure 2:
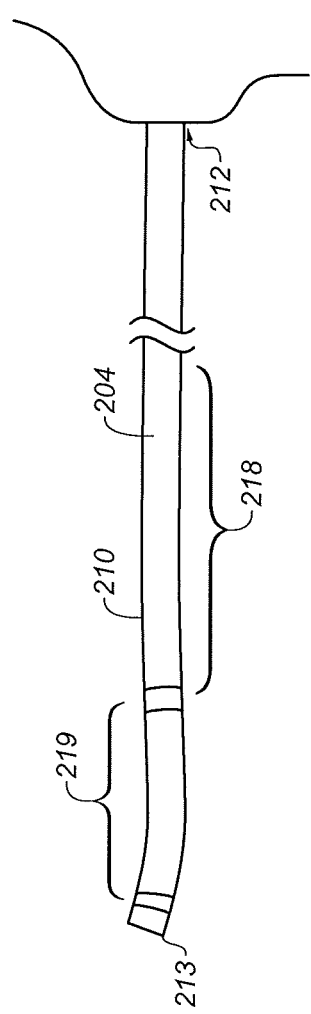
FIG. 2 is a partially schematic representation of an elongate shaft member of the medical system, according to various example embodiments.

FIG. 2 shows portions of elongate shaft member 210 of a medical system 200, according to example embodiments. In some embodiments, elongate shaft member 210 is elongate and flexible, and includes a circumferential exterior wall 204. Elongate shaft member 210 includes a proximal end 212 and a distal end 213. In some embodiments, expandable structure 202 (not shown in FIG. 2) may be physically coupled to the distal end 213. In various embodiments, the elongate shaft member 210 is arranged to be delivered (e.g., percutaneously, intravascularly or through a natural bodily opening) to a bodily cavity or organ with the distal end 213 positioned to be delivered ahead of the proximal end 212. In some embodiments, the elongate shaft member 210 is configured such that the proximal end 212 is located out of a body when the distal end 213 is delivered to a desired destination with the body (e.g., in an organ such as the atrium of a heart). In various embodiments, elongate shaft member 210 includes at least one lumen therein (e.g., extending between the proximal end 212 and the distal end 213). In some embodiments, elongate shaft member 210 is a hollow shaft member or a tubular shaft member.

With reference to FIGS. 3A and 3B, there are shown partial schematic cutaway views of elongate shaft member 210, from top and bottom views, respectively, according to some embodiments. A first pair of steering lines 220 and a second pair of steering lines 221 may be disposed within or inward from an exterior surface of elongate shaft member 210 according to some embodiments. The first pair of steering lines 220 and a second pair of steering lines 221 may be disposed within or inward from the exterior wall 204 of the elongate shaft member according to some embodiments. The first pair of steering lines 220 includes a first proximal steering line 222 and a first distal steering line 226. The second pair of steering lines 221 includes a second proximal steering line 224 and a second distal steering line 228. Each of the steering lines 222, 224, 226, and 228 may be formed of metal (e.g., stainless steel) according to some embodiments. Each of the steering lines 222, 224, 226, and 228 may be formed of a synthetic or polymer material according to some embodiments. In some embodiments, each of the steering lines 222, 224, 226, and 228 are disposed with a respective tubular member (not shown) that is provided the elongate shaft member 210. In some embodiments each tubular member includes a low friction material (e.g., polytetrafluoroethylene (PTFE)) to reduce resistance to movements of the steering line through the tubular member.

The first and second proximal steering lines 222, 224 are terminated at the elongate shaft member 210 respectively at a first proximal termination portion 214 and a second proximal termination portion 215 of the elongate shaft member 210. Similarly, the first and second distal steering lines 226, 228 are terminated at the elongate shaft member 210 respectively at a first distal termination portion 216 and a second distal termination portion 217 of the elongate shaft member 210.

In some embodiments, each of the first distal termination portion 216 of the elongate shaft member 210 and the second distal termination portion 217 of the elongate shaft member 210 is located relatively closer to a distal end 213 than each of the first proximal termination portion 214 of the elongate shaft member 210 and the second proximal termination portion 215 of the elongate shaft member 210.

In various embodiments, each steering line of the plurality of steering lines includes a respective first end portion that includes a first end of the steering line and a respective second end portion including a second end of the steering line, the first end portion and the second end portion spaced from one another across a length of the steering line. For example, the first proximal steering line 222 may include a first end portion 223*a*-1 that includes the first end 223*a* and a second end portion 223*b*-1 that includes second end 223*b*. The second proximal steering line 224 may include a first end portion 225*a*-1 that includes first end 225*a* and second end portion 225*b*-1 that includes a second end 225*b*. Similarly, the first distal steering line 226 may include a first end portion 227*a*-1 that includes a first end 227*a* and a second end portion 227*b*-1 that includes a second end 227*b*, and the second distal steering line 228 may include a first end portion 229a-1 that includes a first end 229a and a second end portion 229b-1 that includes a second end 229b. In various embodiments, the respective second end portion 223b-1 of the first proximal steering line 222 terminates at first proximal termination portion 214 of elongate shaft member 210, and the respective second end portion 227b-1 of the first distal steering line 226 terminates at first distal termination portion 216 of elongate shaft member 210. In various embodiments, the respective second end portion 225b-1 of the second proximal steering line 224 terminates at the second proximal termination portion 215 of the elongate shaft member 210, and the respective second end portion 229b-1 of the second distal steering line 228 terminates at the second distal termination portion 217 of the elongate shaft member 210. It is noted, in various embodiments, that the entirety of each of at least some of the respective second end portions 223b-1, 225b-1, 227b-1, and 229b-1 need not be directly fixedly coupled to the respective one of the termination portions 214, 215, 216, and 217 of the elongate shaft member 210 by the termination of the each of at least some of the respective second end portions 223b-1, 225b-1, 227b-1, and 229b-1. For example, at least one of the respective second ends 223b, 225b, 227b, and 229b may terminate just beyond the respective termination portion 214, 215, 216, 219. Nonetheless, in this example, the respective second end portion may still be considered to be terminated at the respective termination portion.

Each of the steering lines 222, 224, 226, and 228 may have various material compositions according to various embodiments. For example, in some embodiments, various ones of the steering lines 222, 224, 226, and 228 may be made from various suitable cable materials including various polymers (e.g., ultra-high-molecular-weight polyethylene (UHMWPE)) or metallic materials (e.g., stainless steel). The various steering lines 222, 224, 226, and 228 may be terminated, secured or otherwise fastened or attached to respective ones of the termination portions 214, 215, 216, and 217 by various techniques including the use of mechanical fasteners, knots, bonding employing various adhesives, welding and combinations thereof. To minimize the overall size requirements of the elongate shaft member 210, techniques that generally produce a lower-profile or smaller termination joint are generally preferred. In various embodiments, the overall cross-sectional size of the elongate shaft member 210 is generally desired to be as small as possible when employed as a catheter required to be delivered through restrictive bodily openings (e.g., various vascular passages). In some embodiments, a proximal steering ring 300 and a distal steering ring 302 are disposed in (e.g., within or, in some embodiments, inward from an exterior surface of) the elongate shaft member 210, for example, as shown in the partial section view of FIG. 4. In some embodiments, the proximal steering ring 300 and the distal steering ring 302 are disposed in (e.g., within or, in some embodiments, inward from) the exterior wall 204 of the elongate shaft member 210. Advantageously, in some embodiments, the proximal steering ring 300 and the distal steering ring 302 are disposed within the exterior wall 204 of the elongate shaft member 210 so as to provide additional structural support to the exterior wall 204 and to allow for a reduced size or dimension (e.g., thickness, diameter or circumference) of elongate shaft member 210, as compared to, for example, some embodiments where the proximal steering ring 300 and the distal steering ring 302 are disposed radially inward from the exterior wall 204. In some embodiments, the proximal steering ring 300 provides termination portions 214, 215, and the distal steering ring 302 provides termination portions 216, 217. In some embodiments, the proximal and distal steering rings 300, 302 are metal (e.g., stainless steel). In some embodiments, each of at least the proximal steering ring 300 or the distal steering ring 302 is arranged or configured to have a closed form (e.g., a closed continuous ring). For example, in some embodiments distal steering ring 302 is a continuous closed ring, with notches or slots formed therein along the longitudinal direction of the shaft 210 that do not entirely sever the distal steering ring 302, in which at least part of the second end portions 227b-1 and 229b-1 of the distal steering lines 226, 228 are welded or adhered. In some embodiments, the distal steering ring 302 includes slots along the longitudinal direction of the shaft 210 that entirely sever the distal steering ring, in which at least part of the second end portions 227b-1 and 229b-1 of the distal steering lines 226, 228 are welded or adhered. In some of these embodiments, the welding or adhering of the distal steering lines 226, 228 fills the slots and, therefore, the distal steering ring 302 may still be considered a continuous closed ring. In some embodiments, each of at least the proximal steering ring 300 or the distal steering ring 302 is arranged or configured to have an open form (e.g., an open ring including one or more complete interruptions that respectively prevent a path that extends around the entirety of the ring). For example, in some embodiments, proximal steering ring 300 is an open ring with at least one compete interruption. In some embodiments, proximal steering ring 300 is an open ring with at least two complete interruptions as described below in this disclosure, for example, with respect to gaps 309, 310. It is noted that an open ring that includes multiple complete interruptions may essentially comprise a plurality of separate components. These separate components may include one or more spaces therebetween but are considered to still form part of a ring when positioned in a ring-like configuration or constrained by at least part of the elongate shaft member 210 to maintain a ring-like configuration. For example, proximal steering ring 300 may include two spaced apart portions, the two spaced apart portions maintained by the elongate shaft member 210 in a spatial orientation that defines a ring-like shape from the two portions.

In some embodiments, the elongate shaft member 210 is produced, at least in part, by welding the steering lines 222, 224, 226, 228 to the proximal and distal rings 300, 302 as shown, for example, in FIG. 4, and the external wall 204 of the shaft is formed around the steering lines 222, 224, 226, 228 and the rings 300, 302 by melting a polymer (example materials discussed in more detail below). The openings 251 (two called out in FIG. 4) in the proximal and distal rings 300, 302 provide regions that may be filled by such polymer during the melting process to facilitate integral formation of the exterior wall 204 and the proximal and distal rings 300, 302, according to some embodiments.

In various embodiments, elongate shaft member 210 includes a proximal bending portion (e.g., proximal bending portion 218 described in further detail below) and a distal bending portion (e.g., distal bending portion 219 described in further detail below). In some embodiments, the proximal steering ring 300 is disposed at or proximate the proximal bending portion 218 of the elongate shaft member 210 and the distal steering ring 302 is disposed at or proximate the distal bending portion 219 of the elongate shaft member 210. In various embodiments, various respective portions of the steering lines 222, 224, 226, 228 are terminated at the proximal steering ring 300 or the distal steering ring 302. In some embodiments, the second end portion 223b-1 of the first proximal steering line 222 is terminated at the proximal steering ring 300 at a location at least proximate to the second end 223b. In some embodiments, the second end portion 225b-1 of the second proximal steering line 224 is terminated at the proximal steering ring 300 at a location at least proximate to the second end 225b. In some embodiments, the second end portion 227b-1 of the first distal steering line 226 is terminated at the distal steering ring 302 at a location at least proximate to the second end 227b and the second end portion 229b-1 of the second distal steering line 228 is terminated at the distal steering ring 302 at a location at least proximate the second end 229b. Although some examples are provided above, each of the steering lines 222, 224, 226, and 228 may be terminated, secured or otherwise fastened or attached to respective ones of the proximal and distal steering rings 300, 302 by a number of different methods. For example, when each of the steering lines 222, 224, 226, and 228 and the proximal and distal steering rings 300, 302 are made from metal (e.g., stainless steel), welding may be employed to achieve relatively low profile connections.

In some embodiments, (for example, with reference to FIGS. 3A and 3B), the proximal bending portion 218 may be positioned or located proximal (e.g., toward the proximal end 212 of elongate shaft member 210) at least (a) the first proximal termination portion 214 of the elongate shaft member 210 or (b) the second proximal termination portion 215 of the elongate shaft member 210. In some embodiments, the distal bending portion 219 may be positioned or located distal at least (a) or (b).

Figure 4:
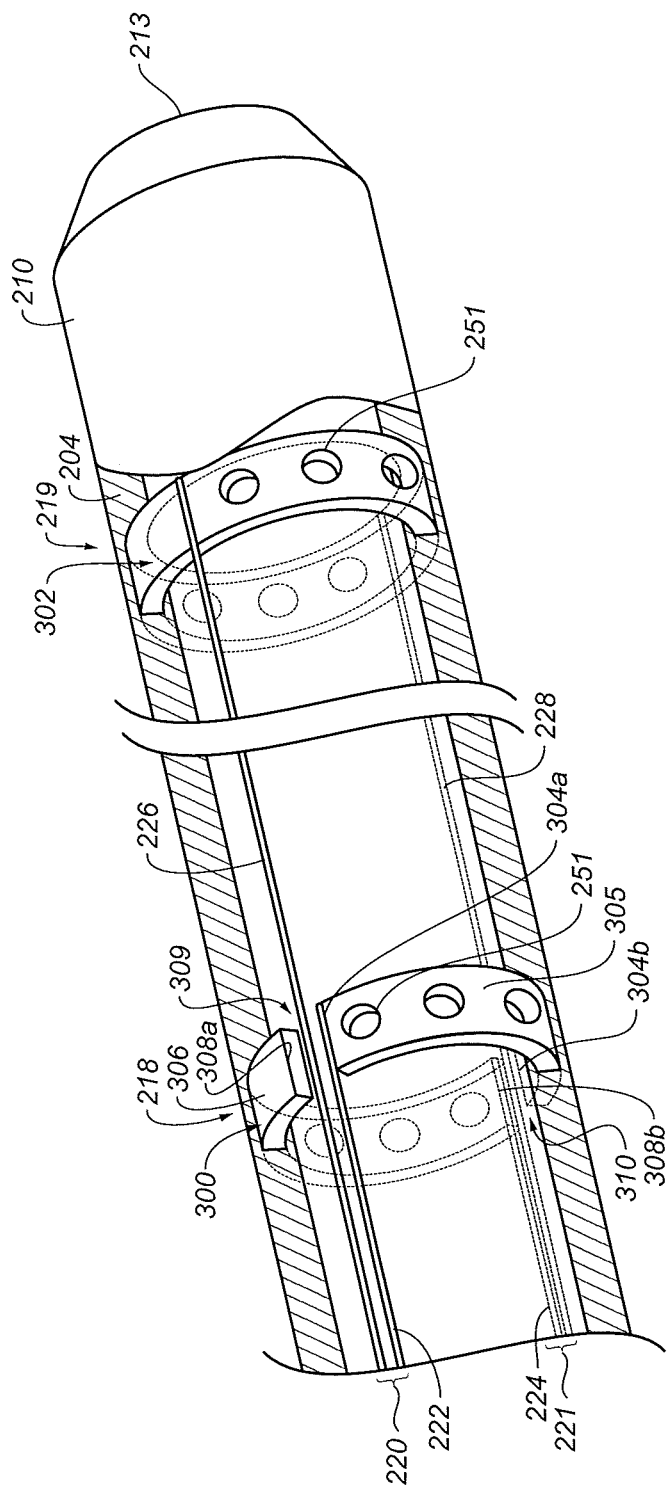
FIG. 4 is a partial cutaway view of an elongate shaft member including a proximal steering ring portion, a distal steering ring portion and steering lines, according to various example embodiments.

In some embodiments, with reference to FIGS. 3A, 3B, and 4, the proximal steering ring 300 may include a first semi-circular ring portion 305 and a second semi-circular ring portion 306, which are spaced apart, while the distal steering ring 302 includes a single circular or closed member. In some embodiments, the second end portion 223b-1 (FIG. 3A) of the first proximal steering line 222 terminates on or at the first semi-circular ring portion 305. In some embodiments, the second end portion 225b-1 (FIG. 3B) of the second proximal steering line 224 is terminated at or on second semi-circular ring portion 306. According to various embodiments, the first semi-circular ring portion 305 may include a first edge portion 304a (FIG. 4) and a second edge portion 304b (FIG. 4). Similarly, the second semi-circular ring portion 306 may include a first edge portion 308a (FIG. 4) and a second edge portion 308b (FIG. 4). The first semi-circular ring portion 305 and the second semi-circular ring portion 306 may be arranged such that the first edge portion 304a of the first semi-circular ring portion 305 and the first edge portion 308a of the second semi-circular ring portion 306 define a first gap 309 according to some embodiments. In some embodiments, the first gap 309 is within the exterior wall 204 of the elongate shaft member 210. Similarly, first semi-circular ring portion 305 and the second semi-circular ring portion 306 may be arranged such that the second edge portion 304b of the first semi-circular ring portion 305 and the second edge portion 308b of the second semi-circular ring portion 306 define a second gap 310. In some embodiments, the second gap 310 is within the exterior wall 204 of the elongate shaft member 210. In some embodiments, the first distal steering line 226 passes through the first gap 309, and the second distal steering line 228 passes through the second gap 310. In some embodiments, the first distal steering line 226 passes through the first gap 309, and the second distal steering line 228 passes through the second gap 310 as each of the first and second distal steering lines 226, 228 extend toward respective termination locations at or on distal steering ring 302. As described below in further detail, the first and second distal steering lines 226, 228 may be operatively coupled to the distal steering ring 302 to cause selective bending of distal bending portion 219, and the first and second proximal steering lines 222 and 224 may be operatively coupled to the proximal steering ring 300 to cause selective bending of proximal bending portion 218 according to various embodiments. In this regard, the first and second gaps 309 and 310 allow respective ones of the first and second distal steering lines 226, 228 to travel to termination locations at or on the distal steering ring 302 without obstruction by the proximal steering ring 300 to allow selective bending of the distal bending portion 219. In some embodiments, various channels, holes, or other openings are provided in proximal steering ring 300 to allow passage of first and second distal steering lines 226, 228.

Figure 5:
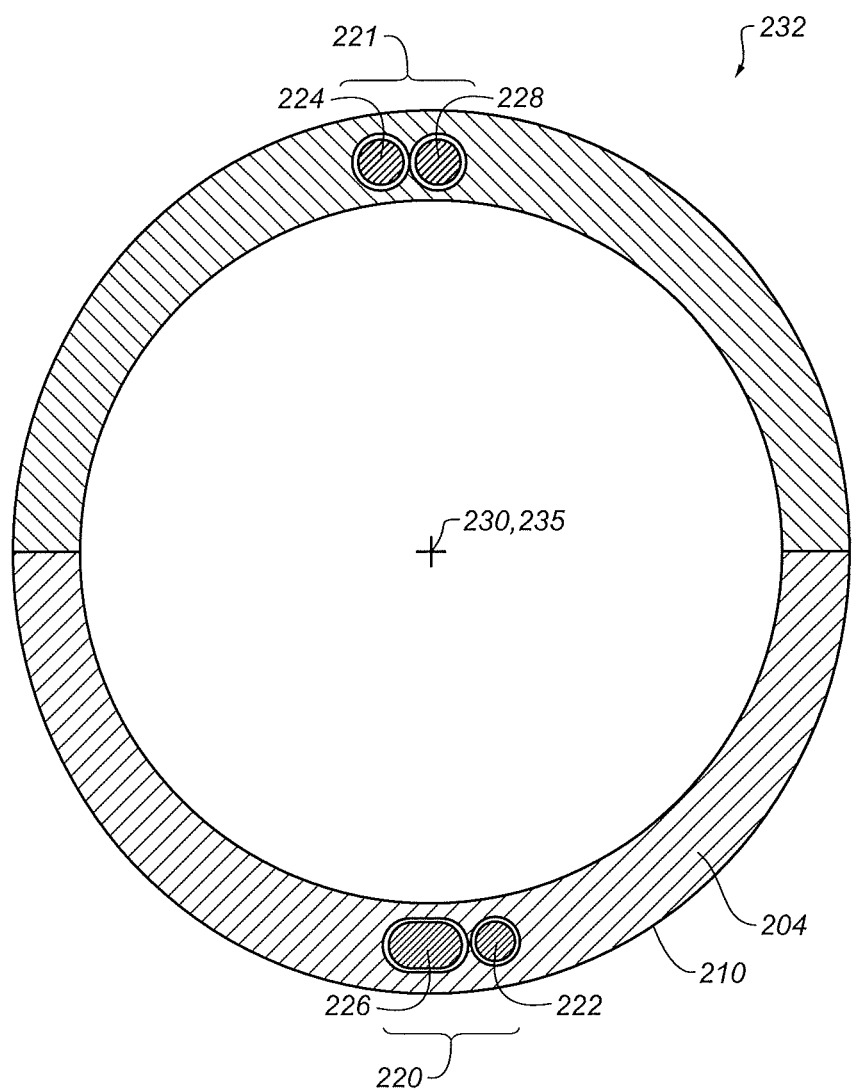
FIG. 5 is cross-section view of a proximal portion of an elongate shaft member including steering lines, according to various example embodiments.

FIG. 5 is a cross-sectional view of the elongate shaft member 210 at a proximal portion 232 of the elongate shaft member 210. For example, the proximal portion 232 may be located proximal (i.e., toward the proximal end 212 of elongate shaft member 210) the proximal bending portion 218 according to various embodiments. In some embodiments, the proximal portion 232 may be located proximal (i.e., toward the proximal end 212 of elongate shaft member 210) the proximal steering ring 300, or proximal at least proximal termination portion 214 or proximal termination portion 215. According to some embodiments, the first pair of steering lines 220 and second pair of steering lines 221 are disposed at opposite sides, about a longitudinal axis 230 (a location thereof depicted by a "+" with the understanding that the longitudinal axis 230 extends into and out of the page in FIGS. 5, 6, 7A, 7B, 10A, 10B, 10C), of the shaft member 210. Longitudinal axis 230 extends between the proximal end 212 and the distal end 213 of the elongate shaft member 210 and through a geometric center 235 or centroid of a cross-section of the elongate shaft member 210, according to some embodiments. As used herein, the term "longitudinal axis" has the meaning of an axis along the lengthwise direction or vector of the elongate shaft member 210. As described above, portions of the elongate shaft member 210 may be bent during use. In such cases, as used herein, the longitudinal axis would bend in a manner corresponding to any bending of the elongate shaft member 210.

Figure 6:
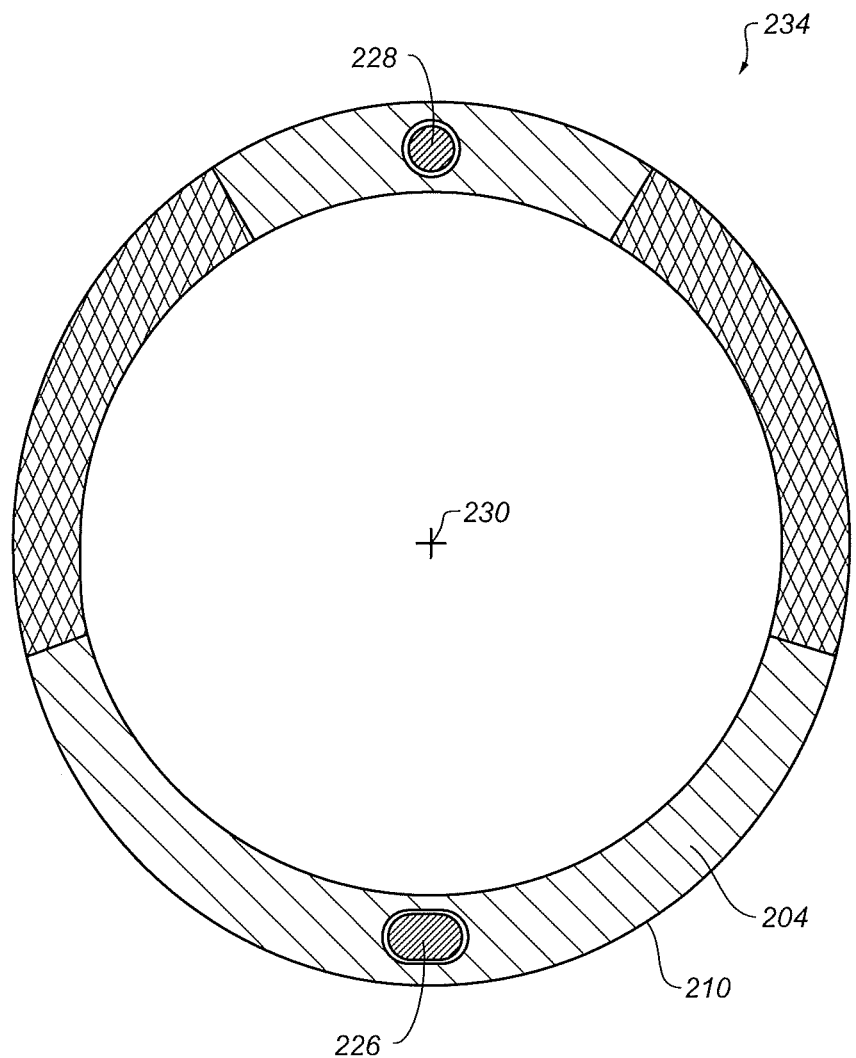
FIG. 6 is cross-section view of a distal portion of an elongate shaft member including steering lines, according to example embodiments.

FIG. 6 is a cross-sectional view of the elongate shaft member 210 at a distal portion 234 of the elongate shaft member 210. For example, the distal portion 234 may be located distal (i.e., toward the distal end 213 of elongate shaft member 210) the proximal steering ring 300 or distal at least proximal termination portion 214 or proximal termination portion 215. In some embodiments, the distal portion 234 may be located between the proximal steering ring 300 and the distal steering ring 302. In FIG. 6, the first distal steering line 226 and the second distal steering 228 line are disposed at opposite sides, about longitudinal axis 230 of the elongate shaft member 210. It is noted that, according to various embodiments, the first and second proximal steering lines 222 and 224 are not present in the distal portion 234 having been terminated more proximally along the elongate shaft member 210. In FIG. 5, the steering lines 222, 224, 226, and 228 are angularly spaced about and radially spaced from longitudinal axis 230. In FIG. 6, the steering lines 226, 228 are angularly spaced about and radially spaced from longitudinal axis 230. It is noted according to various embodiments, that the steering lines 222, 224, 226 and 228 may each be contained in a respective lumen. In some embodiments, various ones of these respective lumens may be sized and dimensioned to allow movement or translation of a steering line within the lumen to, for example, impart a bending force in the elongate shaft member 210. Each of the lumens may be provided in various manners. In some embodiments, small tubular members made from a low friction material (e.g., polytetrafluoroethylene (PTFE)) are molded within at least part of the elongate shaft member 210 to provide various ones the respective lumens that enclose, surround or provide passageways for various ones of the steering lines.

Figure 7A:
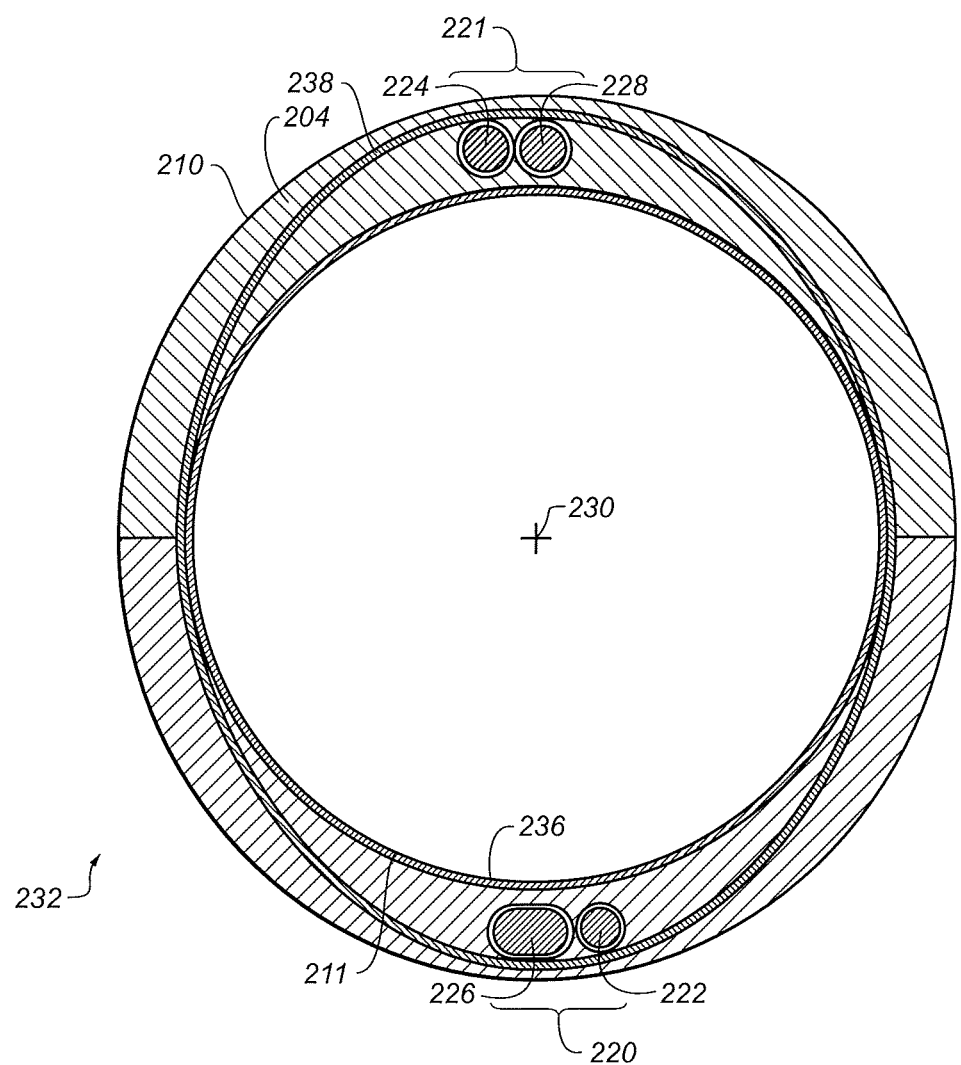
FIG. 7A is cross-section view of an elongate shaft member including steering lines and a lumen, according to example embodiments.
Figure 7B:
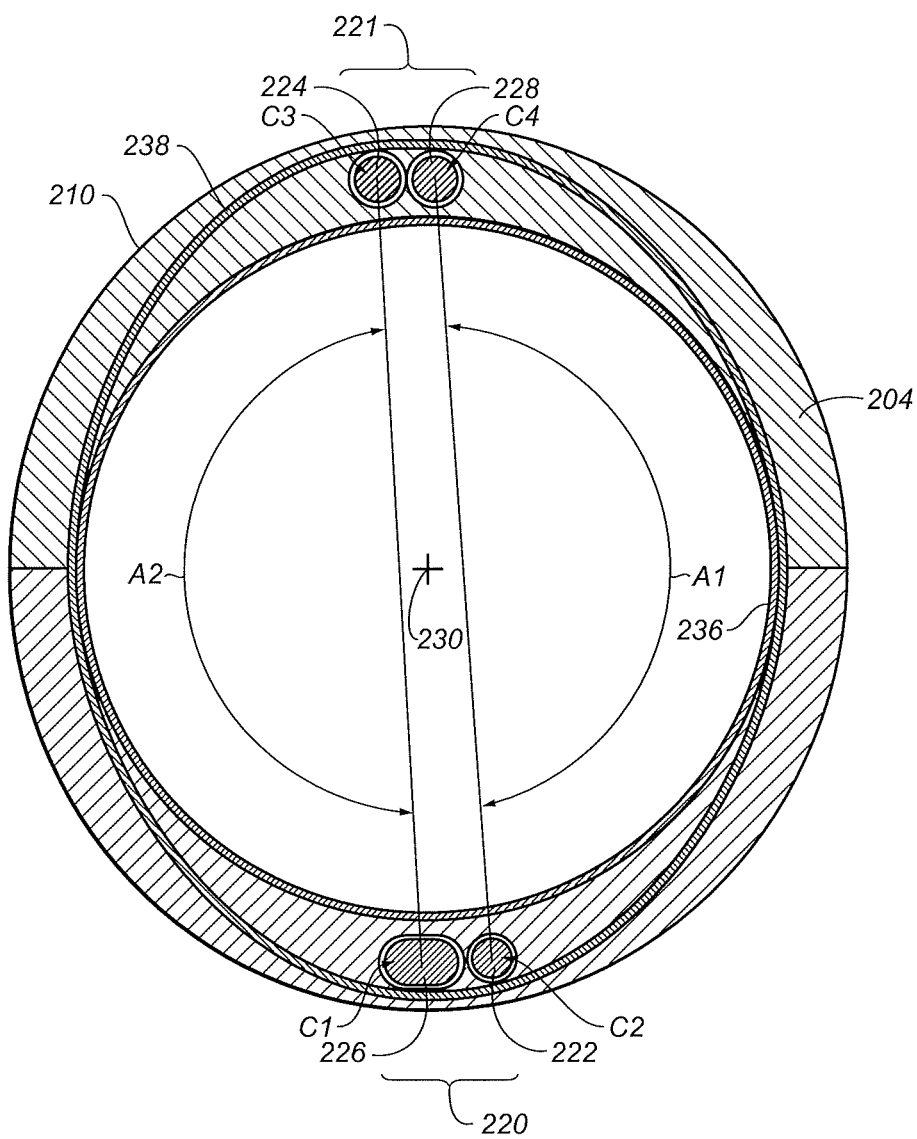
FIG. 7B is cross-section view of an elongate shaft member including an arrangement of steering lines, according to example embodiments.

In some embodiments, elongate shaft member 210 is a tubular member. In some embodiments, the exterior wall 204 of the elongate shaft member 210 is arranged in a tubular configuration. In some embodiments, elongate shaft member 210 includes one or more lumens extending between the proximal end 212 and distal end 213 of the elongate shaft member. FIG. 7A is a cross-sectional view of elongate shaft member 210, including a lumen 211, according to various embodiments. In some embodiments, the elongate shaft member 210 is an elongate sheath that includes a lumen 211 sized and dimensioned to selectively allow passage of a medical instrument therethrough during percutaneous or intravascular delivery of a medical instrument along a path through the lumen 211. In some embodiments, the medical instrument includes an expandable structure (e.g., expandable structure 202). In some embodiment, the elongate shaft member 210 including lumen 211 is physically coupled to an expandable structure (e.g., expandable structure 202). For example, the elongate shaft member 210 including lumen 211 may form at least part of a medical instrument (e.g., a diagnostic or treatment catheter). In various embodiments, elongate shaft member 210 may include various layers. In some embodiments, the various layers are arranged in a concentric arrangement. In FIGS. 7A and 7B, a low friction material layer 236 (e.g., a polytetrafluoroethylene (PTFE) layer) is employed according to various embodiments. The use of a material layer such as layer 236 may be motivated for different reasons. For example, a low friction material layer such as layer 236 may be appropriately located in elongate shaft member 210 to facilitate movement of a particular element (e.g., a medical instrument) through a lumen provided in elongate shaft member 210. Various layers made from metallic or non-metallic materials may be incorporated into elongate shaft member 210, according to various embodiments. In some of these various embodiments, some of these layers may be reinforcement layers or backing layers for other layers or components provided within elongate shaft member 210.

Various spatial relationships between the steering lines 222, 224, 226, 228 may be employed according to various embodiments. For example, with reference to FIG. 7B, the steering lines 222, 224, 226, 228 may be arranged in certain configurations within (e.g., within an exterior wall 204 of) elongate shaft member 210. For example, in some embodiments, the steering lines 222, 224, 226, 228 are angularly spaced about and radially spaced from longitudinal axis 230 of the elongate shaft member 210, as viewed along the longitudinal axis 230, with at least an angular spacing A1 between the first proximal steering line 222 and the second distal steering line 228 being approximately 180 degrees, or an angular spacing A2 between the second proximal steering line 224 and the first distal steering line 226 being approximately 180 degrees.

In some embodiments, the steering lines 222, 224, 226, 228 are arranged in a circumferential arrangement about longitudinal axis 230 of the elongate shaft member 210, as viewed along the longitudinal axis 230. In some embodiments, the steering lines 222, 224, 226, 228 are arranged in an arrangement in which the steering lines 222, 224, 226, 228 are angularly arranged about longitudinal axis 230 of the elongate shaft member 210, as viewed along the longitudinal axis 230. In various embodiments, each of at least some of the steering lines 222, 224, 226, 228 are radially spaced from the longitudinal axis 230 as viewed along the longitudinal axis 230. In various embodiments, each of at least some of the steering lines 222, 224, 226, 228 are radially spaced inwardly from an exterior surface of the elongate shaft member 210. In some embodiments, when viewed along the longitudinal axis 230, at least a first set of one more of the steering lines 222, 224, 226, 228 are arranged to a first side of the longitudinal axis 230 and a second set of the steering lines 222, 224, 226, 228 are arranged to a second side of the longitudinal axis 230, the second side opposite across the longitudinal axis 230 from the first side. For example, in FIG. 7B, the steering lines 224 and 228 are arranged to a first side of longitudinal axis 230 while steering lines 222 and 226 are arranged to a second side of longitudinal axis 230, the second side opposite to the first side when viewed along the longitudinal axis 230 (again represented by the symbol "+"). Also in other embodiments, associated with FIG. 7B, the steering lines 224 and 226 are also arranged to a first side of longitudinal axis 230 while steering lines 222 and 228 are arranged to a second side of longitudinal axis 230, the second side opposite to the first side when viewed along the longitudinal axis 230. In some embodiments, the first side is a first half of a cross-section of the elongate shaft member 210, and the second side is a second half of the cross-section of the elongate shaft member 210, the second half opposite to the first half, the cross-section within a plane perpendicular to the longitudinal axis 230. In some embodiments, the steering lines 222, 224, 226, 228 have an arrangement discussed above in this paragraph or otherwise herein within or inward from the exterior wall 204 of the elongate shaft member 210.

In FIGS. 7A and 7B, member 238 encloses or surrounds various ones of the steering lines 222, 224, 226, and 228. The use of member 238 may be motivated for different reasons. For example, member 238 may facilitate securing of various ones of the steering lines 222, 224, 226, and 228 (and, in some cases, any respective tubular elements that each of the various ones of the steering lines 222, 224, 226, and 228 run through) within elongate shaft member 210. Member 238 may facilitate maintaining or substantially maintaining various ones of the steering lines 222, 224, 226, and 228 at their respective locations within elongate shaft member 210 during a bending of elongate shaft member 210 or during a movement of at least some of steering lines 222, 224, 226, and 228 to, for example, cause bending of elongate shaft member 210. In some embodiments, member 238 is formed of metal (e.g., stainless steel) and may be spirally or helically wound (e.g., along an extension direction of at least a portion of the longitudinal axis 230) to surround various ones of the steering lines 222, 224, 226, and 228. The helically wound configuration may be employed to secure the various ones of the steering lines 222, 224, 226, and 228 while not unduly restricting the ability of elongate shaft member 210 to bend.

In some embodiments, the steering lines 222, 224, 226, 228 are arranged in a particular arrangement in which the steering lines 222, 224, 226, 228 are angularly spaced about and radially spaced from longitudinal axis 230 of the elongate shaft member 210, as viewed along the longitudinal axis 230. In this regard, when viewed along the longitudinal axis 230, adjacent ones of the steering lines 222, 224, 226, 228 may define a respective angle therebetween, each respective angle radiating outwardly from the longitudinal axis 230 as viewed along the longitudinal axis 230. According to various embodiments, an angular spacing between the steering lines of a first adjacent pair of the steering lines in the particular arrangement is different than an angular spacing between the steering lines of a second adjacent pair of the steering lines in the particular arrangement. In some embodiments, the first adjacent pair of the steering lines is provided by the first proximal steering line 222 and the first distal steering line 226, and the second adjacent pair of the steering lines is provided by (a) the first proximal steering line 222 and one of the second proximal steering 224 line and the second distal steering line 228, or (b) the first distal steering line 226 and one of the second proximal steering line 224 and the second distal steering line 228. For example, In FIG. 7B, the first adjacent pair of the steering lines is provided by the first proximal steering line 222 and the first distal steering line 226, and the second adjacent pair of the steering lines is provided by the first proximal steering line 222 and the second distal steering line 228, with an angular spacing between the steering lines of the first adjacent pair of the steering lines being different than the angular spacing between the steering lines of the second adjacent pair of the steering lines. It is noted that in other embodiments, the second proximal steering line 224 and the second distal steering line 228 may have their locations swapped or exchanged from those shown in FIG. 7B, and that, in this regard, the first adjacent pair of the steering lines may be provided by the first proximal steering line 222 and the first distal steering line 226, and the second adjacent pair of the steering lines is provided by the first proximal steering line 222 and the second proximal steering line 224.

In some embodiments, the angular spacing between the steering lines of the first adjacent pair of the steering lines is smaller than the angular spacing between the steering lines of the second adjacent pair of the steering lines as viewed along the longitudinal axis 230. For example, in FIG. 7B the angular spacing (i.e., as viewed along longitudinal axis 230) between the first adjacent pair of the steering lines provided by the first proximal steering line 222 and the first distal steering line 226 is smaller than the angular spacing (again, as viewed along longitudinal axis 230) between the second adjacent pair of the steering lines provided by the first proximal steering line 222 and the second distal steering line 228.

In some embodiments, the steering lines 222, 224, 226, 228 are angularly arranged about longitudinal axis 230 of the elongate shaft member 210, as viewed along the longitudinal axis 230, and (a) an angular spacing between the first proximal steering line 222 and the first distal steering line 226 is less than 80 degrees, or (b) an angular spacing between the second proximal steering line 224 and the second distal steering line 228 is less than 80 degrees. In some embodiments, the steering lines 222, 224, 226, 228 are angularly arranged about longitudinal axis 230 of the elongate shaft member 210, as viewed along the longitudinal axis 230, and (a) an angular spacing between the first proximal steering line 222 and the first distal steering line 226 is less than 80 degrees, or (b) an angular spacing between the second proximal steering line 224 and the second distal steering line 228 is less than 45 degrees, or less than 30 degrees in some embodiments, or less than 20 degrees in other embodiments or even less than 10 degrees in yet other embodiments. Further, the relative sizes or dimensions or shapes of the different ones of the steering lines 222, 224, 226, 228 may differ. For example, in some embodiments, each of the steering lines 222, 224, 226, 228 includes a respective cross-sectional shape when viewed in a direction along longitudinal axis 230 of the elongate shaft member 210, and the respective cross-sectional shape of the first proximal steering line 222 is different than the respective cross-sectional shape of the first distal steering line 226. In some embodiments, each respective steering line of the steering lines 222, 224, 226, 228 includes a respective cross-sectional area when viewed in a direction along a respective longitudinal axis of the respective steering line (such respective cross-sectional area being transverse to the respective longitudinal axis, and the respective longitudinal axis being parallel to longitudinal axis 230 according to some embodiments), and the respective cross-sectional area of the first proximal steering line 222 is different than the respective cross-sectional area of the first distal steering line 226. In some embodiments, the respective cross-sectional area C1 of the first distal steering line 226 is greater than at least the respective the first proximal steering line 222 cross-sectional area of C2 or the second proximal steering line 224 cross-sectional area of C3, or the second distal steering line 228 cross-sectional area of C4.

The use of various steering lines including geometries including different sizes, dimensions, shapes, or different material compositions, etc., may be motivated for different reasons. For example, as further described below, first distal steering line 226 is employed to bend distal bending portion 219 according to various embodiments and may see a greater loading than others of the steering lines 222, 224, and 228 especially when a significant bend is required in the distal bending portion 219 as exemplified in at least FIG. 8A. A steering line such as first steering line 226 may at least employ stronger materials or larger sectional profiles to withstand the increased loading. In FIGS. 7A and 7B, first distal steering line 226 has a generally oval cross-section which may be motivated by different reasons including providing a relatively small thickness to reduce the overall size of the elongate shaft member 210 required to contain the steering line 226 while providing a relatively large width to resist increased loading conditions. By way of non-limiting example, other cross-sectional shapes including rectangular, square, and elliptical may be employed by various ones of the steering lines 222, 224, 226, and 228.

With reference to FIGS. 9A, 9B, and 9C, and with continued reference to FIGS. 2, 3A, and 3B, there is shown the elongate shaft member 210 in various bending or deflection configurations. In some embodiments, elongate shaft member 210 includes proximal bending portion 218 and distal bending portion 219. Operation of one or more of the proximal steering lines 222, 224, attached to proximal steering ring 300, contributes to elongate shaft member 210 bending at the proximal bending portion 218. Similarly, operation of one or more of the distal steering lines 226, 228, attached to distal steering ring 302, contributes to elongate shaft member 210 bending at the distal bending portion 219. Separate operation of a first set of the proximal steering lines (e.g., proximal steering lines 222, 224) and a second set of the distal steering lines (e.g., distal steering lines 226, 228) can provide respective control of the bending of proximal bending portion 218 and distal bending portion 219. Such control via (a) one or more of the proximal steering lines (e.g., proximal steering lines 222, 224), via (b) one or more of the distal steering lines (e.g., distal steering lines 226, 228), or via both (a) and (b) provides the ability to efficiently move elongate shaft member 210 and, for example, expandable structure 202, through a bodily opening providing a passageway (e.g., an artery), and accurately position expandable structure 202 within a bodily cavity (e.g., an atrium of a heart). Operation of the steering lines 222, 224, 226, 228 may be accomplished via use of a control device, such as that described below with respect to FIGS. 9A, 9B, and 9C, which are provided for example and are based in part on teachings from FIGS. 15a, 15b, and 15c of U.S. Pat. No. 5,715,817, issued Feb. 10, 1998, to Stevens-Wright et al.

In some embodiments, the proximal steering ring 300 is disposed at or proximate the proximal bending portion 218 of the elongate shaft member 210, and the distal steering ring 302 is disposed at or proximate the distal bending portion 219 of the elongate shaft member 210.

In some embodiments, the proximal bending portion 218 is positioned proximal (e.g., toward the proximal end 212 of elongate shaft member 210) at least the first proximal termination portion 214 of the elongate shaft member 210 or the second proximal termination portion 215 of the elongate shaft member 210 (see also FIGS. 3A and 3B). In some embodiments, the proximal bending portion 218 is positioned proximal (e.g., toward the proximal end 212 of elongate shaft member 210) proximal steering ring 302. In some embodiments the distal bending portion 219 of the elongate shaft member 210 is located distal (e.g., toward the distal end 213 of elongate shaft member 210) at least one of the first proximal termination portion 214 or the second proximal termination portion 215. In some embodiments, the distal bending portion 219 of the elongate shaft member 210 is located at least (a) between the first proximal termination portion 214 of the elongate shaft member 210 and at least the first distal termination portion 216 of the elongate shaft member 210 or the second distal termination portion 217 of the elongate shaft member 210 or (b) between the second proximal termination portion 215 and at least the first distal termination portion 216 of the elongate shaft member 210 or the second distal termination portion 217 of the elongate shaft member 210. In some embodiments, the distal bending portion 219 of the elongate shaft member 210 is located distal (e.g., toward the distal end 213 of elongate shaft member 210) proximal steering ring 300. In some embodiments, the distal bending portion 219 of the elongate shaft member 210 is located between the proximal steering ring 300 and the distal steering ring 302.

In some embodiments, the elongate shaft member 210, by way of the various configurations of the various embodiments of the present invention, permits opposing movement of the first proximal steering line 222 and the second proximal steering line 224 to bend the proximal bending portion 218 of the elongate shaft member 210 in a first direction D1 of two opposing directions within a first plane, and permits opposing movement of the first proximal steering line 222 and the second proximal steering line 224 to bend the proximal bending portion 218 of the elongate shaft member 210 in a second opposite direction D2 of the two opposing directions within the first plane (for example, as shown in FIGS. 8A, 9A, and 9C). In some embodiments, the elongate shaft member 210 permits concurrent opposing movement of the first proximal steering line 222 and the second proximal steering line 224 to bend the proximal bending portion 218 of the elongate shaft member 210 in a first direction D1 of two opposing directions within a first plane, and permits concurrent opposing movement of the first proximal steering line 222 and the second proximal steering line 224 to bend the proximal bending portion 218 of the elongate shaft member 210 in a second opposite direction D2 of the two opposing directions within the first plane.

Similarly, in some embodiments, the elongate shaft member 210 permits opposing movement of the first distal steering line 226 and the second distal steering line 228 to bend the distal bending portion 219 of the elongate shaft member 210 in a first direction D3 of two opposing directions within a second plane, and permits opposing movement of the first distal steering line 226 and the second distal steering line 228 to bend the distal bending portion 219 of the elongate shaft member 210 in a second opposite direction D4 of the two opposing directions within the second plane (for example as shown in FIG. 8A). In some embodiments, the elongate shaft member 210 permits concurrent opposing movement of the first distal steering line 226 and the second distal steering line 228 to bend the distal bending portion 219 of the elongate shaft member 210 in a first direction D3 of two opposing directions within a second plane, and permits concurrent opposing movement of the first distal steering line 226 and the second distal steering line 228 to bend the distal bending portion 219 of the elongate shaft member 210 in a second opposite direction D4 of the two opposing directions within the second plane. According to various embodiments, bending the proximal bending portion 218 of the elongate shaft member 210 in the first and second directions D1 and D2 may occur in a single plane and may be referred to as bidirectional bending. According to various embodiments, bending the distal bending portion 219 of the elongate shaft member 210 in the first and second directions D3 and D4 may occur in a single plane and may be referred to as bidirectional bending.

Operation of the first and second proximal steering lines 222, 224 to bend the proximal bending portion 218 of the elongate shaft member 210 may involve releasing tension in one of first and second proximal steering lines 222, 224 and increasing tension (e.g., in a concurrent manner or a sequential manner) in the other of the first and second proximal steering lines 222, 224, according to some embodiments. Additionally or alternatively, operation of the first and second proximal steering lines 222, 224 to bend the proximal bending portion 218 of the elongate shaft member 210 may involve playing out or moving at least part of one of the first and second proximal steering lines 222, 224 distally (e.g., in a direction from the proximal end 212 of the elongate shaft member 210 toward the distal end 213 of the elongate shaft member 210) and taking up or moving (e.g., in a concurrent manner or a sequential manner) at least part of the other of the first and second proximal steering lines 222, 224 proximally (e.g., in a direction from the distal end 213 of the elongate shaft member 210 toward the proximal end 212 of the elongate shaft member 210). In this regard, the steering lines 222, 224 may act as tendons, with bending of the proximal bending portion 218 occurring in the direction toward the particular one of the first and second steering lines 222, 224 that at least (a) undergoes increased tension levels or (b) is taken up. It is noted, according to some embodiments, that the other one of the first and the second proximal steering lines 222, 224 that at least (c) undergoes decreased tension levels or (d) is played out, does so at least in order to not restrain or hinder the proximal bending portion 218 of the elongate shaft member 210 from bending in the direction toward the particular one of first and second steering lines 222, 224 that is undergoing increased tension levels or is taken up. It is understood that the first and the second distal steering lines 226, 228 may be manipulated or operated in an identical or similar manner to bend distal bending portion 219 of the elongate shaft member 210.

Various actuators may be employed to cause operation of the first and the second proximal steering lines 222, 224 to bend the proximal bending portion 218 of the elongate shaft member 210 in each of direction D1 and D2 or in each of two directions or vectors in a single plane. By way of non-limiting example, FIGS. 9A, 9B, and 9C (collectively FIG. 9) are schematic representations of an actuator device system 240 (also called an actuator, housing, handle, control device, or control device system 240) coupled to the elongate shaft member 210 and operable for bending at least part of the elongate shaft member (e.g., proximal bending portion 218) in two directions within a single plane by manipulation of two steering lines (e.g., steering lines 222, 224 in FIGS. 9A, 9B, and 9C). Since the present invention is not limited to any particular technique for causing push/pull or take-up/play-out movement of steering lines, FIG. 9 are provided as an example based in part on FIGS. 15a, 15b, and 15c of U.S. Pat. No. 5,715,817, issued Feb. 10, 1998, to Stevens-Wright et al., known in the art.

In various embodiments associated with FIG. 9, manipulation of the first and second proximal steering lines 222, 224 may occur concurrently. In FIG. 9, each of the first and second proximal steering lines 222, 224 is terminated, connected or otherwise fastened to respective ones of termination portions 214, 215 of the elongate shaft member 210 as described above in this disclosure. Additionally, the first and the second proximal steering lines 222, 224 are each terminated, connected or otherwise fastened to slider 242 of actuator 240. Various guides 244 may be provided to guide first and second proximal steering lines 222, 224 to their respective termination locations on slider 242 according to various embodiments. Slider 242 is guided by a guide system (not shown) to move in various directions (e.g., first direction 241a in FIG. 9A and second direction 241b in FIG. 9B). In some embodiments, movement of slider 242 may occur in response to direct manipulation thereof by a user. In some embodiments, movement of slider 242 may occur in response to operation of an electric motor or other actuator including pneumatic and hydraulic actuators. FIG. 9B shows slider 242 in an initial or ready position corresponding to a state before an actuated bending of proximal bending portion 218 of elongate shaft member 210. In FIG. 9B, substantially equal levels of tension may be provided in the first and the second proximal steering lines 222, 224 before an actuated bending of proximal bending portion 218 of elongate shaft member 210. That is, tension levels in the first and the second proximal steering lines 222, 224 may be such that any force differential applied by the steering lines to terminations portions 214, 215 may be insufficient to noticeably bend the proximal bending portion 218 predominately in one of the two directions D1 and D2. In some embodiments, however tension levels in the steering lines 222, 224 may be varied to cause a force differential sufficient to bias the proximal bending portion 218 to bend in a particular one of the two directions D1 and D2 by an initial amount when the slider is positioned in the ready position. In FIG. 9A, slider 242 has been moved along direction 241a and has increased tension (e.g., represented by a relatively straight line form 246a) in second proximal steering line 224 while concurrently reducing tension (e.g., represented by the exaggerated wiggly line form 246b) in first proximal steering line 222 to bend proximal bending portion 218 in the direction D1. In FIG. 9C, slider 242 has been moved along direction 241b and has increased tension (e.g., represented by a relatively straight line form 248a) in first proximal steering line 222 while concurrently reducing tension (e.g., represented by the exaggerated wiggly line form 248b) in second proximal steering line 224 to bend proximal bending portion 218 in the direction D2. It is understood that similar actuation systems may be employed to operate the first and the second distal steering lines 226 and 228 to selectively bend the distal bending portion 219 of the elongate shaft member 210 in either of directions D3 and D4. Other embodiments may employ other actuation systems to selectively bend the proximal bending portion 218 of the elongate shaft member 210 in either of directions D1 and D2 and to selectively bend distal bending portion 219 of the elongate shaft member 210 in either of directions D3 and D4. In some embodiments, the elongate shaft member 210 permits a set of the steering lines 222, 224, 226, 228 to be moved to cause a first portion of a projected outline of the elongate shaft member 210 to include a first curve 250 and a second portion of the projected outline to include a second curve 252 as shown in FIG. 8A. In some embodiments, the projected outline is an outline of the elongate shaft member 210 as projected on a spatial plane. In some embodiments, the first curve 250 is concave toward a first region of space, and the second curve 252 is convex toward the first region of space (e.g., a region of space 259b shown in FIG. 8A and located in the same spatial plane as the curves 250, 252). In some embodiments, the first curve 250 of the projected outline corresponds to a first curve segment 254 of the elongate shaft member 210, and the second curve 252 of the projected outline corresponds to a second curve segment 256 of the elongate shaft member 210. In some embodiments, the first curve segment 254 and the second curve segment 256 are within a same plane.

In some embodiments, the first curve segment 254 of the elongate shaft member 210 is located proximal at least the first proximal termination portion of 214 of the elongate shaft member 210 or the second proximal termination portion 215 of the elongate shaft member 210, and the second curve segment 256 of the elongate shaft member 210 is located distal at least the first proximal termination portion 214 or the second proximal termination portion 215. For example, in FIG. 8A, the first curve segment 254 of the elongate shaft member 210 is located proximally adjacent the second termination portion 215 of the elongate shaft member 210 and the second curve segment 256 of the elongate shaft member 210 is located distally adjacent the first proximal termination portion 214. In this regard, it may also be said that the first curve segment 254 of the elongate shaft member 210 is located proximal both the first and the second proximal termination portions 214, 215 of the elongate shaft member 210, and the second curve segment 256 of the elongate shaft member 210 is located distal both the first and second proximal termination portions 214, 215.

In some embodiments, the elongate shaft member 210 permits a set of the plurality of steering lines 222, 224, 226, 228 to be moved to cause proximal bending portion 218 of the elongate shaft member 210 to include a first curve segment (e.g., first curve segment 254), and distal bending portion 219 of elongate shaft member 210 to include a second curve segment (e.g., second curve segment 256). In various embodiments, the first curve segment (e.g., first curve segment 254) is concave toward a first region of space (e.g., a region of space 259a shown in FIG. 8A) and the second curve segment (e.g., second curve segment 256) is convex toward the first region of space (e.g., region of space 259a). In various embodiments, the first curve segment 254 and the second curve segment 256 are positionable within a same plane, with the region of space 259a also within that same plane.

FIGS. 8B and 8C include other non-limiting examples of various bent configurations that elongate shaft member 210 may assume in response to a moving or operation of various ones of the steering lines 222, 224, 226, and 228. For example, the configuration of FIG. 8B may be obtained via a moderate push/pull or take-up/play-out operation of the distal steering lines 226, 228, while the proximal steering lines 222, 224 remain in a neutral state, according to some embodiments. Also, for example, the configuration of FIG. 8C may be obtained via a more extensive push/pull or take-up/play-out operation of the distal steering lines 226, 228 (as compared to that shown in FIG. 8B) along with a moderate push/pull or take-up/play-out operation of the proximal steering lines 222, 224, according to some embodiments. FIGS. 10A, 10B, 10C, 11, and 12 show views of embodiments of the elongate shaft member 210, formed of materials having different degrees of hardness or bending stiffness.

In some embodiments, the elongate shaft member 210 includes a first set of one or more materials and a second set of one or more materials. The hardness of each material in the first set of one or more materials is greater than a hardness of each material in the second set of one or more materials according to various embodiments. Each of the materials in the first set of one or more materials may be a polymer material according to some embodiments. Each of the materials in the second set of one or more materials may be a polymer material according to various embodiments.

Materials from the first set of one or more materials and the second set of one or more materials may be distributed throughout elongate shaft member 210 in various predetermined manners for various reasons including varying the resistance to bending of a particular portion of the elongate shaft member 210 to bend in one particular direction over another direction. In some embodiments, the particular direction and the another direction may be opposite directions. Another reason may be summarized as distributing materials from the first set of one or more materials and the second set of one or more materials in the elongate shaft member 210 to facilitate bending (for example, in response to movement or other operation of various ones of the steering lines 222, 224, 226, and 228) in one particular direction over another direction. In some embodiments, the particular direction and the another direction may be opposite directions. Yet another reason may be summarized as distributing materials from the first set of one or more materials and the second set of one or more materials in the elongate shaft member 210 to enable one particular portion of the elongate shaft member 210 to resist buckling or kinking forces caused by the bending (for example, in response to movement or other operation of various ones of the steering lines 222, 224, 226, and 228) of another portion of the elongate shaft member 210. The use of materials of different degrees of hardness facilitates different bending properties or characteristics among various parts of elongate shaft member 210. For example, in some embodiments, the ease of bending (e.g., a measure of a resistance to bending) of proximal bending portion 218 in one particular direction may be made to be different than the ease of bending of distal bending portion 219 in the one particular direction.

Although, material hardness is employed in this discussion related to bending, it is understood that bending stiffness is a characteristic that typically is discussed in terms of the "bendability" of a particular element. Bending stiffness, for some materials, is typically related to an area moment of inertia of a cross-section of the element and an elastic modulus (sometimes called Young's modulus) of a material from which the element is made. In some embodiments, different elastic materials (e.g., different metals), each having a different elastic modulus may be employed to impart different bending stiffness characteristics among various portions of the elongate shaft member 210. In some embodiments, various portions of the elongate shaft member 210 may be formed with different distributions of a particular metal to impart different bending stiffness characteristics in the various portions. For example, different flexure-based patterns (e.g., typically formed by laser cutting techniques) of a metal may be employed to impart different bending stiffness characteristics in various portions of the elongate shaft member 210. It is noted that the bendability or bending stiffness of some materials such as various polymers (whose generally flexible nature makes them suitable for use in catheters) are typically related to their hardness with higher hardness levels (e.g., higher durometers) having greater bending stiffness or resistance to bending than lower hardness levels (e.g., lower durometers). In this regard, hardness, bendability and bending stiffness may be used interchangeably especially in various embodiments in which polymers or other viscoelastic materials are employed. It is further noted that a particular material composition may be manufactured in a number of different configurations, each of the configurations having a different hardness. For example, a particular polymer may be manufactured with one of numerous possible durometer ranges. Benefits of incorporating materials from the above-discussed first set of one or more materials and the above-discussed second set of one or more materials in the elongate shaft member 210 to promote specific bending characteristics in portions thereof are discussed in further detail below.

Distribution of materials from the first set of one or more materials and the second set of one or more materials may be distributed in various manners or configurations in elongate shaft member 210. In various embodiments, elongate strips 400 (shown in FIGS. 10A, 10B, 10C, 11, and 12, sometimes with different references, such as 410, 412, etc., and sometimes with references having the prefix of 400, such as 400a, 400b, 400c, etc.) are angularly arrayed or, in some embodiments, circumferentially arrayed about the longitudinal axis 230 of elongate shaft member 210. In various embodiments, each of various portions of the elongate shaft member 210 (e.g., proximal bending portion 218, distal bending portion 219) includes a respective group of the elongate strips 400. Each respective group of the elongate strips 400 may be angularly arrayed or, in some embodiments, circumferentially arrayed about longitudinal axis 230 of elongate shaft member 210 according to some embodiments. In some embodiments, a length of each of the plurality of elongate strips 400 is shorter than a length of the elongate shaft member 210 between the proximal end 212 and the distal end 213 of the elongate shaft member 210. In some embodiments, each elongate strip of the plurality of elongate strips 400 includes at least one material from one of the first set of one or more materials and the second set of one or more materials, but does not include a material from the other of the first set of one or more materials and the second set of one or more materials. The plurality of elongate strips 400 may include at least one material from the first set of one or more materials and at least one material from the second set of one or more materials according to various embodiments. In some embodiments, the plurality of elongate strips 400 includes at least one elongate strip 400 including a material from the first set of one or more materials, but not including a material from the second set of one or more materials, and the plurality of elongate strips 400 includes at least one elongate strip 400 including a material from the second set of one or more materials, but not including a material from the first set of one or more materials.

Figure 10C:
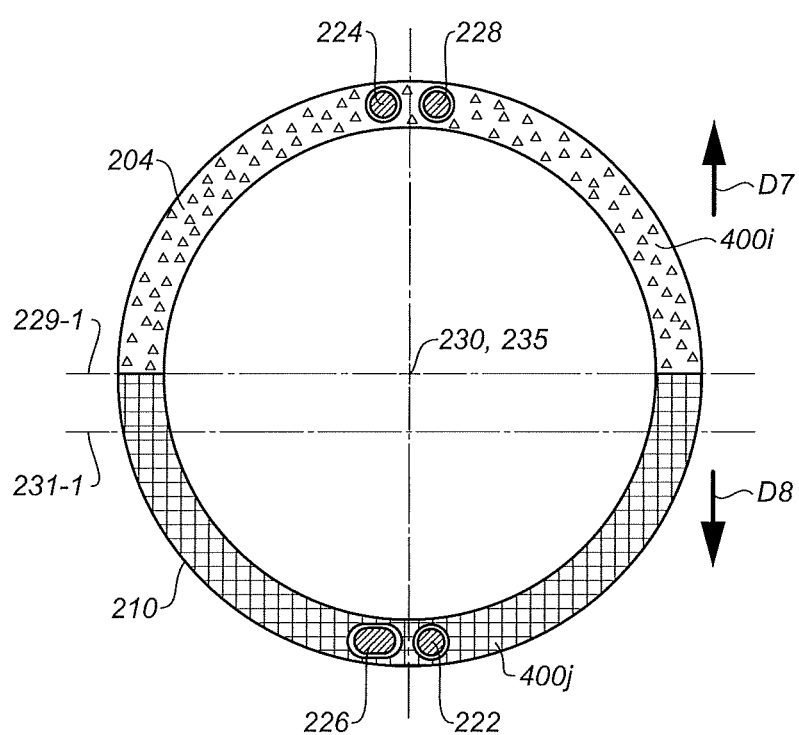

In some embodiments, each of the proximal bending portion 218 and the distal bending portion 219 includes a respective group of the elongate strips circumferentially or radially arranged or arrayed about the longitudinal axis 230 of the elongate shaft member 210. In various embodiments, the term "arrayed" has the meaning of being arranged in a regular, repeating, or alternating manner. In various embodiments, the term "circumferentially" means to be distributed or located around or on a circumference, to surround, or to encircle. According to some embodiments, for each respective group of the elongate strips 400, at least a first elongate strip of the respective group of the elongate strips 400 includes a material from the first set of one or more materials, and at least a second elongate strip of the respective group of the elongate strips 400 includes a material from the second set of one or more materials (for example, as shown in FIGS. 10A, 10B, and 10C described in further detail below).

Figure 12:
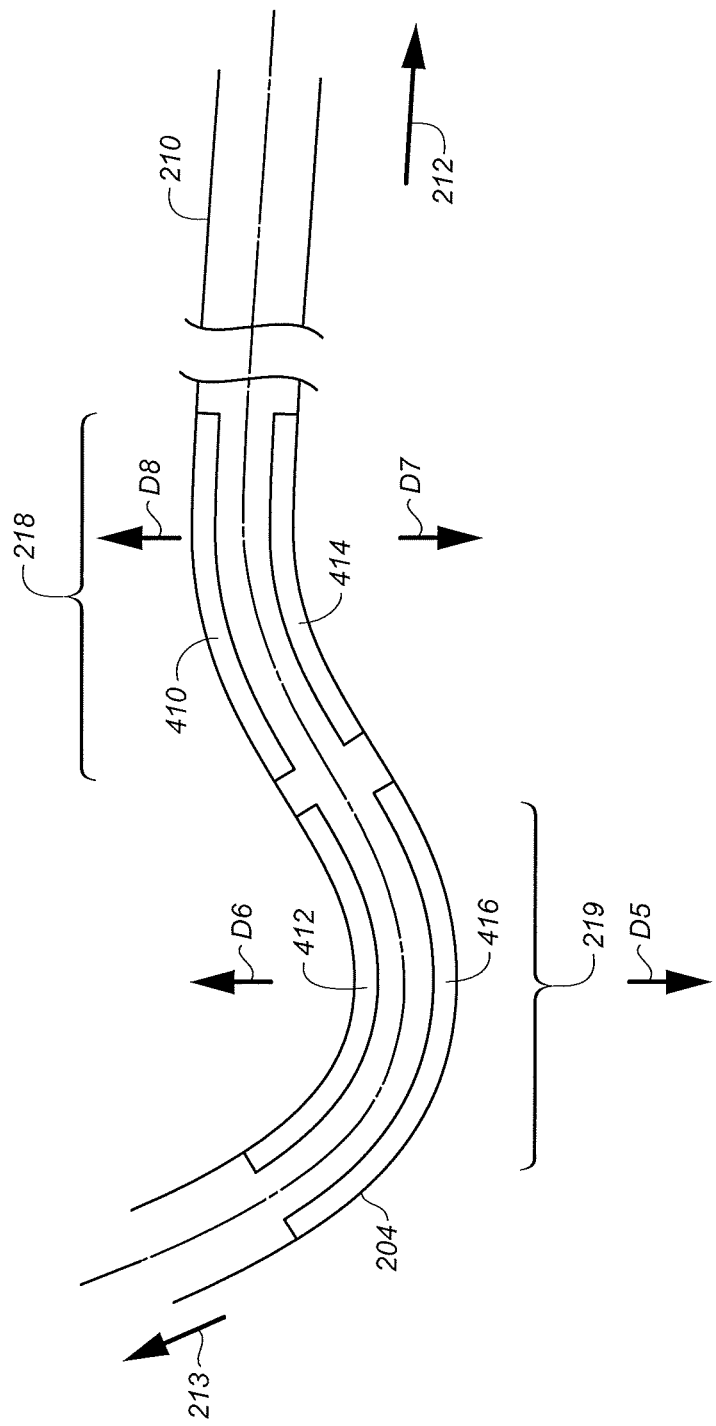

With reference to FIG. 12, in some embodiments, a first elongate strip 410 of the plurality of elongate strips 400 may include a material from the first set of one or more materials, the first elongate strip 410 located at a convex side (or a side to be preferentially bendable toward convex bending (rather than concave bending) due at least to the arrangement of materials with different hardnesses) of the proximal bending portion 218 of the elongate shaft member 210, and a second elongate strip 412 of the plurality of elongate strips 400 includes a material from the second set of one or more materials, with the second elongate strip 412 being located at a concave side (or a side to be preferentially bendable toward concave bending (rather than convex bending) due at least to the arrangement of materials with different hardnesses) of the distal bending portion 219 of the elongate shaft member 210. The convex side of the proximal bending portion 218 of elongate shaft member 210 and the concave side of the distal bending portion 219 of the elongated shaft member may result from various actions including bending various portions of the elongate shaft member 210 in response to movement or operation of various ones of steering lines 222, 224, 226, and 228 as described above in this disclosure. In FIG. 12, it is noted that each of the proximal and the distal bending portions 218, 219 of the elongate shaft member 210 includes a respective convex side (i.e., a side arching outwardly away from longitudinal axis 230) and a respective concave side (i.e., a side arching inwardly toward longitudinal axis 230).

In some embodiments, additional elongate strips 400 may be included. For example, in some embodiments, a third elongate strip 414 of the plurality of elongate strips 400 may include a material from the second set of one or more materials, with the third elongate strip 414 being located at a concave side (or a side to be preferentially bendable toward concave bending (rather than convex bending) due at least to the arrangement of materials with different hardnesses) of the proximal bending portion 218 of the elongate shaft member 210. In various embodiments, the third elongate strip 414 does not include a material from the first set of one or more materials. In some embodiments, the plurality of elongate strips 400 includes a fourth elongate strip 416 that includes a material from the second set of one or more materials, the fourth elongate strip 416 located at a convex side (or a side to be preferentially bendable toward convex bending (rather than concave bending) due at least to the arrangement of materials with different hardnesses) of the distal bending portion 219 of the elongate shaft member 210. In some embodiments, the fourth elongate strip 416 includes a material from the second set of one or more materials does, but not include a material from the first set of one or more materials. However, different anatomical features may require different bending configurations. Accordingly, in some embodiments, the fourth elongate strip 416 includes a material from the first set of one or more materials does but not include a material from the second set of one or more materials. In some embodiments, the elongate shaft member 210 includes each of the first elongate strip 410, the second elongate strip 412, the third elongate strip 414, and the fourth elongate strip 416.

Each of the elongate strips 400 may include various shapes and dimensions when incorporated into elongate shaft member 210. With reference to FIG. 10A (i.e., which is a cross-sectional section view of at least part of elongate shaft member 210 as viewed along longitudinal axis 230), the elongate shaft member 210 includes a plurality of elongate strips 400 including elongate strips 400a, 400b, 400c, and 400d. In some embodiments, each elongate strip 400 of the plurality of elongate strips 400 includes a thickness 420 (only one called out in FIG. 10A), a front surface 422 (only one called out in FIG. 10A) facing radially outwardly from longitudinal axis 230 of the elongate shaft member 210, a back surface 424 (only one called out in FIG. 10A) opposite across the thickness 420 from the front surface 422, and a respective pair of side edges 426 (only one pair called out in FIG. 10A) that define a portion of a periphery of at least the front surface 422 or the back surface 424. The side edges of each pair of side edges 426 are opposed to one another across at least a portion of a length (i.e., extending into and out of the page of FIG. 10A) of the elongate strip 400 according to various embodiments. In some embodiments, each of the plurality of elongate strips 400 includes substantially a same thickness 420. In some embodiments, at least some of the plurality of elongate strips 400 include different thicknesses 420.

Each elongate strip 400 includes a width 427 (only one called out corresponding to elongate strip 400a) between each pair of respective side edges 426, according to some embodiments. In some embodiments, the width 427 of each of the plurality of elongate strips 400 is smaller than a circumference of the elongate shaft member 410. It is noted that the width 427 corresponds to a configuration in which the respective pair of side edges 426 define a periphery of the front surface 422 of an elongate strip 400 (e.g., elongate strip 400a) in FIG. 10A. In other embodiments, the width 427 may correspond to a configuration in which the respective pair of side edges 426 define a periphery of the respective back surface 420.

In some embodiments, the respective pair of side edges 426 form at least part of various side surfaces 428 (only two called out in FIG. 10A) of the respective elongate strip 400, the side surfaces 428 extending along at least part of the length (i.e., again, extending into and out of the page of FIG. 10A) of the elongate strip 400. In some embodiments, the side surfaces 428 are not parallel to one another. For example, in FIG. 10A, side surfaces 428 of elongate strip 400a extend along respective directions or vectors transverse to an extension direction of the length of the elongate strip 400 (e.g., in "quasi-radial" directions) that intersect one another. In some embodiments, each of at least one of the side surfaces 428 of an elongate strip 400 extends along a respective transverse direction or vector that intersects longitudinal axis 230 as viewed along longitudinal axis 230. In some embodiments, none of the side surfaces 428 of an elongate strip 400 extend along respective transverse directions or vectors (e.g., transverse to an extension direction of the length of the elongate strip 400) that intersect longitudinal axis 230 as viewed along longitudinal axis 230. In some embodiments, the side surfaces 428 of an elongate strip 400 extend along respective transverse directions or vectors (e.g., transverse to an extension direction of the length of the elongate strip 400) that intersect each other at a particular location that is not on longitudinal axis 230 as viewed along longitudinal axis 230. In some embodiments, the side surfaces 428 of an elongate strip 400 extend along respective transverse directions or vectors (e.g., transverse to an extension direction of the length of the elongate strip 400) that are parallel to one another as viewed along longitudinal axis 230.

In some embodiments, a side surface 428 of a first one of the elongate strips 400 may be arranged at least proximate, or may abut, a side surface 428 of a second one of the elongate strips 400. In some embodiments, a cross-section of an elongate strip 400 may include a sector-shaped profile when viewed along a longitudinal axis 230 of the elongate shaft member 210, each respective sector-shaped profile subtending an angle less than 360 degrees. In some embodiments, each of at least one of the sector-shaped profiles is defined (e.g., bounded) at least in part by the front surface 422 and the side surfaces 428 of the respective elongate strip 400. In some embodiments, each of at least one of the sector-shaped profile is defined (e.g., bounded) at least in part by the front surface 422, back surface 424 and the side surfaces 428 of the respective elongate strip 400. In some embodiments, at least one of the sector-shaped profiles does not intersect longitudinal axis 230 as viewed along longitudinal axis 230. In some embodiments, e.g., at least when the sector-shaped profile is defined with the back surface 424, such sector-shaped profile will obtain a shape corresponding to the shape of the cross-section of the respective elongate strip 400, such as strip 400a in FIG. 10A. On the other hand, in some embodiments, e.g., at least when the sector-shaped profile is defined without the back surface 424, such sector-shaped profile will obtain a pie-shape that tapers radially inward towards an apex within the elongate shaft member 210. In some of these embodiments, at least one of the sector-shaped profiles intersects longitudinal axis 230 as viewed along longitudinal axis 230 and may be referred to as circular sector or quadrant. In some embodiments, at least one of the sector-shaped profiles is bounded at least in part by longitudinal axis 230 as viewed along longitudinal axis 230. In some embodiments, elongate strips of each of a respective group of the elongate strips 400 are located at a position distanced apart from a geometric center or centroid 235 of the elongate shaft member 210, when viewed along longitudinal axis 230 of the elongate shaft member 210. In some embodiments, elongate strips of each of a respective group of the elongate strips 400 are located at a position distanced apart from longitudinal axis 230 of the elongate shaft member 210, when viewed along longitudinal axis 230 of the elongate shaft member 210. By way of certain embodiments, elongate strips 400 of materials of differing hardness are employed to beneficially reduce or minimize bending stiffness of the proximal bending portion 218 and the distal bending portion 219 in particular bending directions. The elongate strips may also beneficially provide compression stiffness to the proximal bending portion 218 and the distal bending portion 219, to avoid kinking at those locations during, for example, operation or movement of various ones of the steering lines 222, 224, 226, and 228. For example, according to some embodiments, elongate strips 400c and 400d may each include (or be made from) a material in the first set of one or more materials, and the elongate strips 400a and 400b may each include (or be made from) a material in the second set of one or more materials, with a hardness of each material in the first set of one or more materials being greater than a hardness of each material in the second set of one or more materials. For example, according to some embodiments, each of the elongate strips 400c and 400d may be made from various polymers such as PEBAX 5533 (55 shore D durometer) (PEBAX is a Trademark of Arkema France Corporation, 420 Rue d'Estienne d'Orves 92700 Colombes, France) and each of the elongate strips 400a and 400b may be made from a less hard (i.e., softer) polymer such as PEBAX 3533 (35 shore D durometer). Without limitation, polymers employed according to various embodiments may include thermoplastics, thermosets, or elastomers. In some embodiments, composites may be employed. Polymers are examples of various viscoelastic materials that may be employed by various ones of elongate strips 400, according to various embodiments. It is noted that viscoelasticity is a property of materials that exhibit both viscous and elastic characteristics when undergoing stress, such as bending. Classically, elastic materials (e.g., materials that behave according to Hooke's Law), such as various metals when subjected to bending stress, return to their original state once the bending stress is removed. Viscoelastic materials, such as polymers, have both elastic and viscous characteristics and, as such, exhibit time-dependent strain during deformations, such as bending deformations. Specifically, viscoelasticity may be described as a molecular rearrangement. When a stress is applied to various viscoelastic materials, such as polymers, parts of the polymer chains may rearrange in a process called creep. Polymers, however, may remain solid even when these parts of their chains are rearranging in response to the applied stress by creating a back stress in the polymeric material. When the back stress is the same magnitude as the applied stress, the polymer will no longer creep (for example, when the polymer is bent within its elastic range). When the original stress is taken away, the accumulated back stresses will cause the polymer to return to its original form. In this regard, elastic and viscoelastic materials may behave in similar manners when bent. As described above in this disclosure, various parts of elongate shaft member 210 may be bent or steered (e.g., during percutaneous delivery) by the operation of various ones of steering lines 222, 224, 226, and 228. In FIG. 10A, a portion of elongate member 210 is steerable or bendable in direction D5 at least under the influence of a tensile force applied by second distal steering line 228, and is steerable or bendable in direction D6 at least under the influence of a tensile force applied by first distal steering line 226. It is understood that softer (e.g., less stiff) materials such as PEBAX 3533 are easier to bend than relatively harder (e.g., more stiff) materials such as PEBAX 5533 especially when a relatively severe bend (e.g., over 90 degrees in some embodiments, but over 30 degrees in other embodiments) is required. However, if the portion of the elongate shaft member 210 shown in FIG. 10A is made from a circumferential arrangement of elongate strips 400 (e.g., elongate strips 400a, 400b, 400c, and 400d) made solely from a softer or less stiff material in the second set of one or more materials (e.g., PEBAX 3533) to promote bending under the influence of steering lines 226, 228, several problems may rise. A particular one of these problems may include kinking of the shaft member 210 (for example in lateral regions 437 shown in FIG. 10A) when various ones of the steering lines 226, 228 are operated or moved to impart a relatively severe bend in the elongate shaft member 210, since, although the employed softer material facilitates the bending, it also is more susceptible to kinking under the influence of the bending. Another particular problem that may be encountered by the sole use of the softer material is that the elongate shaft member 210 may have an increased susceptibility to buckling as it is pushed during delivery thereof. In cases in which the elongate member 210 is a catheter sheath, any kinks or buckled region may hinder or obstruct a delivery of a catheter device therethrough. In cases in which the elongate shaft member 210 is part of a catheter device, any kinks or buckled region may hinder or obstruct a delivery of the catheter device through a lumen of a catheter sheath.

According to various embodiments, elongate strips 400c and 400d include harder materials from the first set of one or more materials to resist the aforementioned kinking or buckling problems. In this regard, the elongate strips 400a, 400b include the relatively softer (or less stiff) material(s) from the second set of one or more materials to facilitate bending (e.g., in direction D5 or D6) of the elongate shaft member 210 in response to operation of movement of various ones of steering lines 226, 228 while elongate strips 400c, 400d include relative harder (or more stiff) material(s) from the first set of one or more materials to resist at least kinking or buckling, according to some embodiments. In various embodiments, the relatively softer or less stiff elongate strips 400a and 400b are positioned to be intersected in a plane of the bend (e.g., a plane in which a portion of the elongate shaft 210 is bendable in each of the directions D5 and D6). In various embodiments, the relatively harder or stiffer elongate strips 400c and 400d may act as "side stiffeners" that may be positioned at least proximate to regions that may be prone to kinking (e.g., regions 437) when a portion of the elongate shaft member 210 is bent. The relatively harder or stiffer elongate strips 400c and 400d may act as "side stiffeners" that may also be employed to increase the axial stiffness of the elongate shaft members 210 to resist buckling thereof.

It is noted in FIG. 10A that each of the elongate strips 402a, 402b, 402c, and 402d has substantially a same width 427, although such may not be the case in other embodiments. It is noted in FIG. 10A, the respective sector-shaped profiles of the elongate strips 402a, 402b, 402c, and 402d each subtends substantially equal angles, although such may not be the case in other embodiments. It is noted in various embodiments that the elongate strips 400c, 400d advantageously provide only reduced amounts of resistance to bending in either direction D5 or direction D6 since such bending introduces relatively reduced amounts of strain on the elongate strips 400c and 400d. That is, the relatively harder or relatively stiffer elongate members 400c, 400d are positioned to provide little bending resistance with respect to bending in direction D5 or direction D6, while providing improved compression stiffness to resist kinking and buckling (e.g., in regions 437). It is noted that during the bending in either direction D5 or direction D6, relatively larger amounts of strain are imposed on the elongate strips 400a, 400b whose softer, less stiff material properties are better able to accommodate such relatively larger amounts of strain. In addition, the softer material of the elongate strips 400a, 400b promotes ease of bending in the intended directions D5, D6 by reducing resistance to the bending in either direction D5 or direction D6. It is further noted that the relatively symmetrical arrangement of elongate strips 400a, 400b, 400c, and 400d about axis 429 in FIG. 10A provides substantially equal amounts of resistance to bending in each of directions D5 and D6. In some embodiments, axis 429 is known as the centroidal axis 429 as it passes through the geometric center or centroid 235 of the cross-section of the elongate shaft member 210.

In some embodiments, it may be desired to bend a portion of the elongate shaft member 210 in one of two opposing directions (e.g., the directions D5 and D6) with a different amount of resistance to bending that would be required to bend the portion of the elongate shaft member 210 in the other of the two opposing directions. For example, it may be functionally required (for example, by various anatomical constraints) to bend the portion of the elongate shaft member 210 in one of the two opposing directions by a greater angular amount than the other of the two opposing directions. Greater amounts of bending typically require that a particular one of the steering lines (e.g., 222, 224, 226, and 228) apply a greater amount of tensile force. Greater amounts of tensile force can be difficult to apply and can lead to problems such as kinking or bending of various portions of the elongate shaft member 210, breakage, stretching or other failure in the respective steering line providing the tensile force, or failure in steering line coupler or connection. In these embodiments, it may be desirable to reduce these required levels of tensile force while still providing the greater amount of angular bend that may be required.

FIG. 10B is a cross-sectional section view of elongate shaft member 210 including a plurality of elongate strips 400e, 400f, 400g, and 400h circumferentially arrayed about longitudinal axis 230, the elongate strips 400e, 400f, 400g, and 400h being similar in form and function to elongate strips 400a, 400b, 400c, and 400d according to some embodiments. In FIG. 10B, the elongate strips 400g and 400h include, or are formed from, a material (e.g., a polymer material such as PEBAX 5533 having a 55 Shore D durometer) from the first set of one or more materials, and the elongate strips 400e and 400f include, or are formed from, a material (e.g., a polymer material such as PEBAX 3533 having a 35 Shore D durometer) from the second set of one or more materials, the hardness or stiffness of each material in the first set of one or more materials being greater than a hardness or stiffness of each material in the second set of one or more materials. According to various embodiments, elongate strips 400g and 400h include, or are formed from, harder materials from the first set of one or more materials to resist the aforementioned kinking or buckling problems. In this regard, the elongate strips 400e, 400f include, or are formed from, relatively softer (or less stiff) material(s) from the second set of one or more materials to facilitate bending (e.g., in direction D5 or D6) of the elongate shaft member 210 in response to operation of movement of various ones of steering lines 226, 228, while elongate strips 400g, 400h include relatively harder (or more stiff) material(s) from the first set of one or more materials to, for example, resist kinking or buckling. According to some embodiments, a cross-section of at least one (e.g., all in FIG. 10B) of the elongate strips 400e, 400f, 400g, and 400h may include a sector-shaped profile when viewed along a longitudinal axis 230 of the elongate shaft member 210, each respective sector-shaped profile subtending an angle less than 360 degrees, and each sector-shaped profile including a form similar or identical to various embodiments described above. In this regard, each of at least one of the sector-shaped profiles may be defined (e.g., bounded) at least in part by the front surface (e.g., corresponding to 422 in FIG. 10A) and the side surfaces (e.g., corresponding to 428 in FIG. 10A) of the respective elongate strip 400e, 400f, 400g, and 400*h*, or each of at least one of the sector-shaped profiles may be defined (e.g., bounded) at least in part by the front surface (e.g., corresponding to 422 in FIG. 10A), back surface (e.g., corresponding to 425 in FIG. 10A) and the side surfaces (e.g., corresponding to 428 in FIG. 10A) of the respective elongate strip 400*e*, 400*f*, 400*g*, and 400*h*. In some embodiments, at least one of the sector-shaped profiles does not intersect longitudinal axis 230 as viewed along longitudinal axis 230. In some embodiments, at least one of the sector-shaped profiles intersects longitudinal axis 230 as viewed along longitudinal axis 230 and may be referred to as a circular sector or quadrant. In some embodiments, at least one of the sector-shaped profiles is bounded at least in part by longitudinal axis 230 as viewed along longitudinal axis 230. In some embodiments, elongate strips of each of a respective group of the elongate strips 400 are located at a position distanced apart from a centroid or geometric center 235 of the elongate shaft member 210, when viewed along longitudinal axis 230 of the elongate shaft member 210. In some embodiments, elongate strips of each of a respective group of the elongate strips 400 are located at a position distanced apart from longitudinal axis 230 the elongate shaft member 210, when viewed along longitudinal axis 230 of the elongate shaft member 210.

According to various embodiments, each of at least some of the sector-shaped profiles of the elongate strips 400*e*, 400*f*, 400*g*, and 400*h* subtend different angles when viewed along the longitudinal axis 230 of the elongate shaft member 210. For example, in FIG. 10B, elongate strip 400*e* has a sector-shaped profile that subtends an angle α (for example, 60 degrees) that is different (e.g., smaller) than an angle β (for example, 150 degrees) subtended by a sector-shaped profile of the elongate strip 400*f*. According to some embodiments, the sector-shaped profiles of elongate strips 400*g* and 400*h* each subtend a respective angle that is different than at least the angle α or the angle β subtended by respective ones of the sector-shaped profiles of the elongate strips 400*e* and 400*f*. For example, in FIG. 10B, the sector-shaped profiles of elongate strips 400*g* and 400*h* each subtends a respective angle θ (for example, 75 degrees) that is different than each of the angle α and the angle β subtended by respective ones of the sector-shaped profiles of the elongate strips 400*e* and 400*f*. In FIG. 10B, each of the sector-shaped profiles of elongate strips 400*g* and 400*h* subtends a same angle θ. However, in other embodiments, the sector-shaped profiles of elongate strips 400*g* and 400*h* subtend respective angles that are different from one another. According to various embodiments, each of the elongate strips 400*e*, 400*f* includes or is formed from a material from the first set of one or more materials, and each of the elongate strips 400*g*, 400*h* includes, or is formed from, a material from the second set of one or more materials.

The use of elongate strips 400 having different shapes or different sizes or dimensions (e.g., different widths (e.g., a width 427 is illustrated in FIG. 10A) or sector-shaped profiles subtending different angular amounts) or the use of asymmetrical arrangements or distributions of the elongate strips 400 may be motivated for different reasons. For example, in some embodiments, different sized, shaped, or asymmetrically arranged elongate strips 400 are employed to position a neutral axis at desired location, the neutral axis associated with a bending of a particular portion of the elongate shaft member 210.

As used herein, the term "neutral axis" has the meaning of an axis in the cross-section of a member (e.g., a beam or shaft) along which there are no longitudinal stresses or strains when the member is subjected to bending. The neutral axis is perpendicular to a bending direction. Portions of the member to one side of the neutral axis are in tension during a bending of the member while portions of the member to the other side of the neutral axis are in compression during the bending of the member. In some embodiments in which the member comprises an essentially single material composition, the neutral axis and the centroidal axis in a cross-section of the member may be collinear. In some embodiments, in which the member includes a plurality of materials having different hardness or bending stiffness characteristics, a particular symmetrical distribution of the different hardness or bending stiffness characteristics causes the neutral axis and the centroidal axis in a cross-section of the member may be co-linear. For example, in FIG. 10A, the relatively harder or stiffer characteristics of elongate strips 400*c*, 400*d* and the relatively softer or less stiff characteristics of elongate strips 400*a*, 400*b* are symmetrically distributed with respect to the geometric center 235 or centroid in the cross-section of the elongate shaft member 210, and the neutral axis 431 and centroidal axis 429 are, therefore, collinear. In some embodiments, a first material and a second material are located or distributed along the elongate shaft member 210 to provide an off-center neutral axis of the elongate shaft member 210 with respect to the longitudinal axis 230 of the elongate shaft member 210 that passes through a geometric center of a cross-section of the elongate shaft member 210, the cross-section transverse to the longitudinal axis 230, according to some embodiments. FIG. 10B, discussed in more detail below, illustrates neutral axis 431 that is off-center, according to some embodiments.

It is noted that the location of a neutral axis is dependent of various factors including the geometric aspects of different portions of the member and various stiffness characteristics (e.g., elastic modulus, or in the case of some polymers, the relative hardness thereof). In FIG. 10A, although elongate strips 400*a*, 400*b*, 400*c*, and 400*d* have different hardness or stiffness characteristics, a relatively balanced spatial arrangement between the different hardness or stiffness characteristics of the elongate strips 400*a*, 400*b*, 400*c*, and 400*d* locates the neutral axis 431 at the centroid or geometric center 235. In FIG. 10B, however, the asymmetrical or relatively unbalanced spatial arrangement between the different hardness or stiffness characteristics of elongate strips 400*e*, 400*f*, 400*g*, and 400*h* leads to an off-center neutral axis 431 (i.e., a neutral axis 431 that does not intersect a centroid or geometric center 235 of the cross-section of elongate shaft member 210, the cross-section transverse to the longitudinal axis 230, according to some embodiments). In FIG. 10B, the neutral axis 431 is shown spaced apart from axis 429 toward the relatively harder or relatively stiffer elongate strips 400*g*, 400*h*. In various embodiments, various neutral axes described herein are each transverse to the longitudinal axis 230. In various embodiments, various neutral axes described herein are each transverse to the bending direction (e.g., direction D5 or D6).

In FIG. 10A, operation (e.g., tensioning) of either steering line 226 to bend a first particular portion of the elongate shaft member 210 including the illustrated cross-section of FIG. 10A in the direction D6 or steering line 228 to bend the first particular portion of the elongate shaft member 210 in the direction D5 will be subjected to the same amount of bending resistance since each of the steering lines 226, 228 is positioned by substantially the same distance to neutral axis 431 (i.e., a substantially same size lever arm exists in either case). In FIG. 10B, operation (e.g., tensioning) of steering line 226 to bend a second particular portion of the elongate shaft member 210 including the illustrated cross-section of FIG. 10B in the direction D6 will encounter less bending resistance than operation (e.g., tensioning) of the steering line 228 to bend the second particular portion of the elongate shaft member 210 in the direction D5 since steering line 226 is spaced from the neutral axis 431 by a greater distance than steering line 228, and, accordingly, steering line 226 can exert greater leverage to bend the second particular portion of the elongate shaft member 210 in direction D6. Advantageously, this greater leverage may be employed to reduce the force required to be exerted by steering line 226 to bend a portion of the elongate shaft member in direction D6 or to bend a portion of the elongate shaft member 210 in direction D6 by a greater angular amount (for example, as shown in FIG. 8A). It is noted in some embodiments associated with FIG. 10B that relatively greater force may be required to be applied by steering line 228 to bend a portion of elongate shaft member 210 in direction D5. In some embodiments, this relatively greater force matters little especially if various anatomical considerations require relatively minor amounts of bending in direction D5 from this particular portion of the elongate shaft member 210. In some embodiments, it may be stated that a portion of the elongate shaft member 210 is preferentially bendable in one direction of two opposing directions (e.g., direction D6) over the other of the two opposing directions (e.g., direction D5). It is noted, according to various embodiments, that the cross-section view of each of at least FIG. 10A or FIG. 10B may be that of distal portion 234 (for example, shown in FIG. 6). In some embodiments, the cross-section view of each of at least FIG. 10A or FIG. 10B may be that of distal bending portion 219.

It is noted according to various embodiments that other arrangements of elongate strips 400 may be employed to provide an off-center neutral axis (i.e., a neutral axis not intersecting a centroid or geometric 235 center of a cross-section of the elongate shaft member 210, the cross-section transverse to the longitudinal axis 230 according to some embodiments). For example, FIG. 10C includes a cross-sectional section view of elongate shaft member 210 including a plurality of elongate strips 400i, 400j which are similar in form and function, according to some embodiments, to other elongate strips 400 described above and which are circumferentially arranged about longitudinal axis 230. In FIG. 10C, the elongate strip 400j includes, or is formed from, a material (e.g., a polymer material such as Vestamid L2101F having a 72 Shore D durometer) from the first set of one or more materials, and the elongate strip 400i includes, or is formed from, a material (e.g., a polymer material such as PEBAX 4033 having a 40 Shore D durometer) from the second set of one more materials, the hardness or stiffness of each material in the first set of one or more materials being greater than a hardness or stiffness of each material in the second set of one or more materials. According to various embodiments, elongate strip 400j includes, or is formed from, a harder material from the first set of one or more materials (e.g., to resist the kinking or buckling according to some embodiments). Elongate strip 400i may include, or may be formed from, relatively softer (or less stiff) material from the second set of one or more materials to facilitate bending (e.g., in direction D7) of the elongate shaft member 210 in response to operation of movement of various ones of steering lines 222, 224, while elongate strip 400j may include relative harder (or more stiff) material from the first set of one or more materials to resist at least kinking or buckling. According to some embodiments, a cross-section of at least one (e.g., all in FIG. 10B) of the elongate strips 400i, 400j may include a sector-shaped profile when viewed along a longitudinal axis 230 of the elongate shaft member 210, each respective sector-shaped profile subtending an angle less than 360 degrees, each sector-shaped profile including a form similar or identical to various embodiments described above. In this regard, each of at least one of the sector-shaped profiles may be defined (e.g., bounded) at least in part by the front surface (e.g., corresponding to 422 in FIG. 10A) and the side surfaces (e.g., corresponding to 428 in FIG. 10A) of the respective elongate strip 400i, 400j, or each of at least one of the sector-shaped profile may be defined (e.g., bounded) at least in part by the front surface (e.g., corresponding to 422 in FIG. 10A), back surface (e.g., corresponding to 424 in FIG. 10A) and the side surfaces (e.g., corresponding to 428 in FIG. 10A) of the respective elongate strip 400i, 400j. In some embodiments, at least one of the sector-shaped profiles does not intersect longitudinal axis 230 as viewed along longitudinal axis 230. In some embodiments, at least one of the sector-shaped profiles intersects longitudinal axis 230 as viewed along longitudinal axis 230 and may be referred to as a circular sector or quadrant. In some embodiments, at least one of the sector-shaped profiles is bounded at least in part by longitudinal axis 230 as viewed along longitudinal axis 230. In FIG. 10C, each of the two elongate strips 400i, 400j includes a respective sector shaped profile that subtends approximately 180 degrees according to some embodiments. In FIG. 10C, the inclusion of a harder or stiffer material (i.e., from the first set of one or more materials) in the elongate strip 400j and the inclusion of a relatively softer or relatively less stiff material (i.e., from the first set of one or more materials) in the elongate strip 400i causes the neutral axis associated with this particular cross-section to be an off-center neutral axis 231-1 offset from centroidal axis 229-1. In particular, neutral axis 231-1 is offset toward the relatively harder or relatively stiffer elongate strip 400j. In various embodiments, the portion of the elongate shaft member 210 shown in FIG. 10C is subjected to less bending resistance when bent in direction D7 (e.g., in response to at least operation (e.g., tensioning) of steering line 224) than when bent in direction D8 (e.g., in response to at least operation (e.g., tensioning) of steering line 222) at least in part from the difference in hardness of the materials forming strips 400i, 400j. In some embodiments, directions D5 and D7 point to a first region of space and directions D6 and D8 point to a second region of space. In some embodiments, directions D1, D3, D5, and D7 point to a first region of space and the directions D2, D4, D6, and D8 point to a second region of space. It is noted according to various embodiments, that the cross-section view of FIG. 10C may be that of proximal portion 232 (for example, shown in FIG. 5). In some embodiments, the cross-section view of FIG. 10C may be that of proximal bending portion 218.

Referring to FIG. 12, in some embodiments, the elongate strip 410 of the proximal bending portion 218 of elongate shaft member 210 includes, or is formed from, a material in the first set of one or more materials, and the elongate strip 412 of the distal bending portion 219 includes, or is formed from, a material in the second set of one or more materials, each material in the first set of one or more materials having a greater hardness than each material in the second set of one or more materials. For example, the proximal bending portion 218 may include the arrangement of elongate strips 400i and 400j shown in FIG. 10C with the relatively harder or stiffer elongate strip 400j corresponding to the elongate strip 410, and the relatively softer or less stiff elongate strip 400i corresponding to the elongate strip 414, according to some embodiments. The distal bending portion 219 may include the arrangement of elongate strips 400e, 400f, 400g, and 400h shown in FIG. 10B (or the arrangement of elongate strips 400a, 400b, 400c, and 400d shown in FIG. 10A according to some embodiments) with the relatively softer or less stiff elongate strip 400f (or 400b in FIG. 10A) corresponding to the elongate strip 412, and the relatively softer or less stiff elongate strip 400e (or 400a in FIG. 10A) corresponding to the elongate strip 416, according to some embodiments. Bending of the distal bending portion 219 in direction D6 may be accomplished, as described above, by operation or movement (e.g., tensioning) of first distal steering line 226 (not shown in FIG. 12). It is noted that the application of tensile forces by first proximal steering line 226 to bending portion 219 in direction D6 also provides compressive loads to the proximal bending portion 218. These compressive loads can be especially large when higher tensile forces are required to be applied by first distal steering line 226 to impart larger angular bends in the distal bending portion 219 in direction D6. Additionally, the off-center position of the first distal steering line 226 causes the corresponding compressive load to not be applied uniformly to the proximal bending portion 218 but rather to one side thereof. Accordingly, an undesired buckling or bending of the proximal bending portion 218 in direction D8 may also occur (i.e., due to the off-center compressive loading) as a result of bending of the distal bending portion 219 in direction D6 in response to operation of at least first distal steering line 226. Advantageously, incorporating a harder material from the first set of one or more materials into the elongates strip 410 may be employed to resist the off-center compressive loading conditions and reduce or eliminate unwanted buckling or bending of the proximal bending portion 218 in direction D8. In this regard, various embodiments can tailor a particular distribution of materials from the first and the second sets of one or more materials in each of the proximal and distal bending portions 218, 219 to decouple the bending of each of these portions from one another under the selective operation of various ones of the steering lines 222, 224, 226, and 228. Each of the materials in the first set of one or more materials may be a polymer material, according to some embodiments. Each of the materials in the second set of one or more materials may be a polymer material, according to various embodiments.

It is noted according to some embodiments that various arrangements of elongate strips 400 may be in each of a number of various portions of the elongate shaft member 210 including proximal portion 232, distal portion 234, proximal bending portion 218, and distal bending portion 219 by way of non-limiting example. For example, in some embodiments, each of the proximal bending portion 218 and the distal bending portion 219 includes a respective group of the elongate strips 400. In some embodiments, the elongate strips in each respective group of the elongate strips 400 are circumferentially arranged or arrayed about the longitudinal axis 230 of the elongate shaft member 210. In some embodiments, the elongate strips in each respective group of the elongate strips 400 extend circumferentially about (around) the elongate shaft member 210 as viewed along the longitudinal axis 230 of the elongate shaft member 210. According to some embodiments, for each respective group of the elongate strips 400, at least a first elongate strip of the respective group of the elongate strips 400 includes a material from the first set of one or more materials, and at least a second elongate strip of the respective group of the elongate strips 400 includes a material from the second set of one or more materials (for example, as described above in FIGS. 10A, 10B, and 10C). In some embodiments, the respective group of the elongate strips 400 of the proximal bending portion 218 includes a different number of the elongate strips 400 than the number of elongate strips 400 comprised by the respective group of the elongate strips 400 of the distal bending portion 219. For example, the proximal bending portion 218 may include an arrangement of a first number of elongate strips 400 (for example, two elongate strips 400i and 400j arranged in an arrangement similar to or identical to that shown in FIG. 10C), and the distal bending portion 219 may include an arrangement of a different number of elongate strips (for example, four elongate strips 400a, 400b, 400c, and 400d arranged in an arrangement similar to or identical to that shown in FIG. 10A, or as per another example, four elongate strips 400e, 400f, 400g, and 400h arranged in an arrangement similar to or identical to that shown in FIG. 10B).

In some embodiments, the respective group of the elongate strips 400 of the proximal bending portion 218 includes a first number of particular ones of the elongate strips 400 that include a material from the first set of one or more materials, and the respective group of the elongate strips 400 of the distal bending portion 219 includes a second number of particular ones of the elongate strips 400 that include a material from the first set of one or more materials. In some embodiments, the first number is different than the second number. For example, the proximal bending portion 218 may include a respective group of elongate strips 400 similar to or identical to that shown in FIG. 10C which includes a single elongate strip 400 (e.g., elongate strip 400j) including, or formed from, the first set of one or more materials (i.e., a first number of 1), while the distal bending portion 219 may include a respective group of elongate strips similar to that shown in FIG. 10A, which includes two elongate strips 400 (e.g., elongate strips 400c, 400d) each including, or formed from, the first set of one or more materials (i.e., a second number of 2 that that is different than the first number of 1). As per another example, the distal bending portion 219 may include a respective group of elongate strips similar to that shown in FIG. 10B, which includes two elongate strips 400 (e.g., elongate strips 400g, 400h), each including, or formed from, the first set of one or more materials (i.e., a second number of 2 that that is different than the first number of 1).

In some embodiments, the respective group of the elongate strips 400 of the proximal bending portion 218 includes a first number of particular ones of the elongate strips 400 that include a material from the second set of one or more materials, and the respective group of the elongate strips 400 of the distal bending portion 219 includes a second number of particular ones of the elongate strips 400 that include a material from the second set of one or more materials. In some embodiments, the first number is different than the second number. For example, the proximal bending portion 218 may include a respective group of elongate strips 400 similar to or identical to that shown in FIG. 10C which includes a single elongate strip 400 (e.g., elongate strip 400i) including, or formed from, the second set of one or more materials (i.e., a first number of 1), while the distal bending portion 219 may include a respective group of elongate strips similar to that shown in FIG. 10A, which includes two elongate strips 400 (e.g., elongate strips 400a, 400b) each including, or formed from, the second set of one or more materials (i.e., a second number of 2 that that is different than the first number of 1). As per another example, the distal bending portion 219 may include a respective group of elongate strips similar to that shown in FIG. 10B which includes two elongate strips 400 (e.g., elongate strips 400e,

400*f*), each including, or formed from, the second set of one or more materials (i.e., a second number of 2 that that is different than the first number of 1).

In some embodiments, for each respective group of at least one of the respective groups of the elongate strips 400, a total number of particular ones of the elongate members of the respective group including a material from the first set of one or more materials is the same as a total number of particular ones of the elongate members of the respective group including a material from the second set of one or more materials (for example as shown in each of FIGS. 10A, 10B, and 10C). However, the present invention is not so limited, and in some embodiments, for each respective group of at least one of the respective groups of the elongate strips, a total number of particular ones of the elongate members of the respective group including a material from the first set of one or more materials is different than a total number of particular ones of the elongate members of the respective group including a material from the second set of one or more materials.

In some embodiments, each of the proximal bending portion 218 and the distal bending portion 219 includes a first material and a second material. In some embodiments, a hardness of the first material is greater than a hardness of the second material, and a spatial distribution between the first and second materials in the proximal bending portion 218 is different than a spatial distribution between the first and second materials in the distal bending portion 219. In some embodiments, the elongate shaft member 210 includes at least a first material, a second material, a third material, and a fourth material, for example, as shown at least in each of FIGS. 10A and 10C, or, alternatively, 10B and 10C by way of non-limiting example. In some embodiments, a hardness of the first material is greater than a hardness of the second material, and a hardness of the third material is greater than a hardness of the fourth material. A first distribution of the first material and the second material may exist along the proximal bending portion 218 to provide an off-center neutral axis of the proximal bending portion 218 with respect to a longitudinal axis 230 of the elongate shaft member 210 that passes through a centroid or geometric center 235 of a cross-section of the elongate shaft member 210, the cross-section transverse to the longitudinal axis 230 according to some embodiments. For example, the arrangement of different hardness elongate strips 400*i* and 400*j* of FIG. 10C (e.g., exemplified by elongate strips made from polymer materials such as Vestamid (Vestamid is a Trademark of Evonik Degussa Gmbh Corporation, Rellinghauser Strasse, 1-11 Essen, Fed. Rep. Germany 45128) L2101F having a 72 Shore D durometer (e.g., a material of the first set of one or more materials) and PEBAX 4033 having a 40 Shore D durometer (e.g., a material from the second set of one or more materials)) may be employed in the proximal bending portion 218 to provide a respective off-center neutral axis. Further, a second distribution of the third material and the fourth material may exist along the distal bending portion 219 to provide an off-center neutral axis of the distal bending portion 219 with respect to a longitudinal axis 230 of the elongate shaft member 210 that passes through a centroid or geometric center 235 of a cross-section of the elongate shaft member 210, the cross-section transverse to the longitudinal axis 230, according to some embodiments. For example, the arrangement of different hardness elongate strips 400*e*, 400*f*, 400*g*, and 400*h* of FIG. 10B (e.g., exemplified by elongate strips made from polymer materials such as PEBAX 5533 having a 55 Shore D durometer (e.g., a material of the first set of one or more materials) and PEBAX 3533 having a 35 D Shore D durometer (e.g., a material from the second set of one or more materials)) may exist along the distal bending portion 219 to provide an off-center neutral axis of the distal bending portion 219 with respect to the longitudinal axis 230 of the elongate shaft member 210 that passes through the geometric center 235 of the cross-section of the elongate shaft member 210. In some embodiments, a location of an off-center neutral axis of the distal bending portion 219 as viewed along a part of the longitudinal axis 230 of the elongate shaft member 210 extending through the distal bending portion 219 is different than a location of the off-center neutral axis of the proximal bending portion 218 as viewed along a part of the longitudinal axis 230 of the elongate shaft member 210 extending through the proximal bending portion 218. In other words, each off-center neutral axis is a product of the particular materials and arrangement thereof employed in a particular portion of the elongate shaft member 210. Different arrangements or distributions of materials in each of two different portions of the elongate shaft member 210 (e.g., the proximal bending portion 218 and the distal bending portion 219) may lead to different locations of respective ones of the neutral axes (for example, as shown by a comparison of FIGS. 10B and 10C). In various embodiments, the off-center neutral axis of the proximal bending portion 218 and the off-center neutral axis of the distal bending portion 219 are parallel to one another. In various embodiments, the offset neutral axis of the proximal bending portion 218 and the off-center neutral axis of the distal bending portion 219 are located on opposite sides of the longitudinal axis 230 as viewed along a direction of the longitudinal axis 230. In various embodiments, the offset neutral axis of the proximal bending portion 218 and the off-center neutral axis of the distal bending portion 219 correspond to a state in which both the proximal bending portion 218 and the distal bending portion 219 are bendable in a same direction or are bendable within a same plane. It is noted that an orientation of the neutral axis of a particular portion of the elongate shaft member 210 is transverse to a direction that the particular portion of the elongate shaft member 210 is bent.

In some embodiments, the first material is a polymer material. In some embodiments, the second material is a polymer material. In some embodiments, the third material is a polymer material. In some embodiments, the fourth material is a polymer material. In some embodiments, each of the first material and the second material is different than at least one of the third material and the fourth material (e.g., the material of each of the strips 400*a*, 400*b* in FIG. 10A may be different than the material of each of the strips 400*c*, 400*d*, according to some embodiments as exemplified above). On the other hand, in some embodiments, each of the first material, the second material, the third material and the fourth material is different from each of the others of the first material, the second material, the third material and the fourth material. For example, the materials of strips 400*a*, 400*b* in FIG. 10A need not be identical, and the material of strips 400*c*, 400*d* need not be identical, and different hardness materials may be selected to provide desired bending properties of the elongate shaft member 210.

In some embodiments, a first group of materials are distributed in the proximal bending portion 218 to resist bending, in response to movement of a first set of steering lines 222, 224 of the proximal bending 218 portion in a first direction D1 (e.g., shown in FIG. 8A) of two opposing directions within a first plane with a greater resistance than in bending, in response to movement of the first set of the plurality of steering lines 222, 224, of the proximal bending portion 218 in a second direction D2 (e.g., shown in FIG. 8A) of the two opposing directions within the first plane, the second direction D2 of the two opposing directions within the first plane opposite to the first direction D1 of the two opposing directions within the first plane. As described above, a first particular opposing movement of steering lines 222, 224 may be employed to bend the proximal bending portion 218 in the first direction D1 of the two opposing directions within the first plane, and a second particular opposing movement of steering lines 222, 224 may be employed to bend the proximal bending portion 218 in the second direction D2 of the two opposing directions within the first plane.

Similarly, in some embodiments, a second group of materials are distributed in the distal bending portion 219 to resist bending, in response to movement of a second set of the plurality of steering lines 226, 228, of the distal bending portion 219 in a first direction D3 (e.g., shown in FIG. 8A) of a second set of opposing directions within a second plane with a greater resistance than in bending, in response to movement of the second set of the plurality of steering lines 226, 228, of the distal bending portion 219 in a second direction D4 (e.g., shown in FIG. 8A) of the two opposing directions within the second plane, the second direction D4 of the two opposing directions within the second plane opposite to the first direction D3 of the two opposing directions within the second plane. As described above, a first particular opposing movement of steering lines 226, 228 may be employed to bend the distal bending portion 219 in the first direction D3 of the two opposing directions within the second plane, and a second particular opposing movement of steering lines 226, 228 may be employed to bend the distal bending portion 219 in the second direction D4 of the two opposing directions within the second plane.

Figure 11:
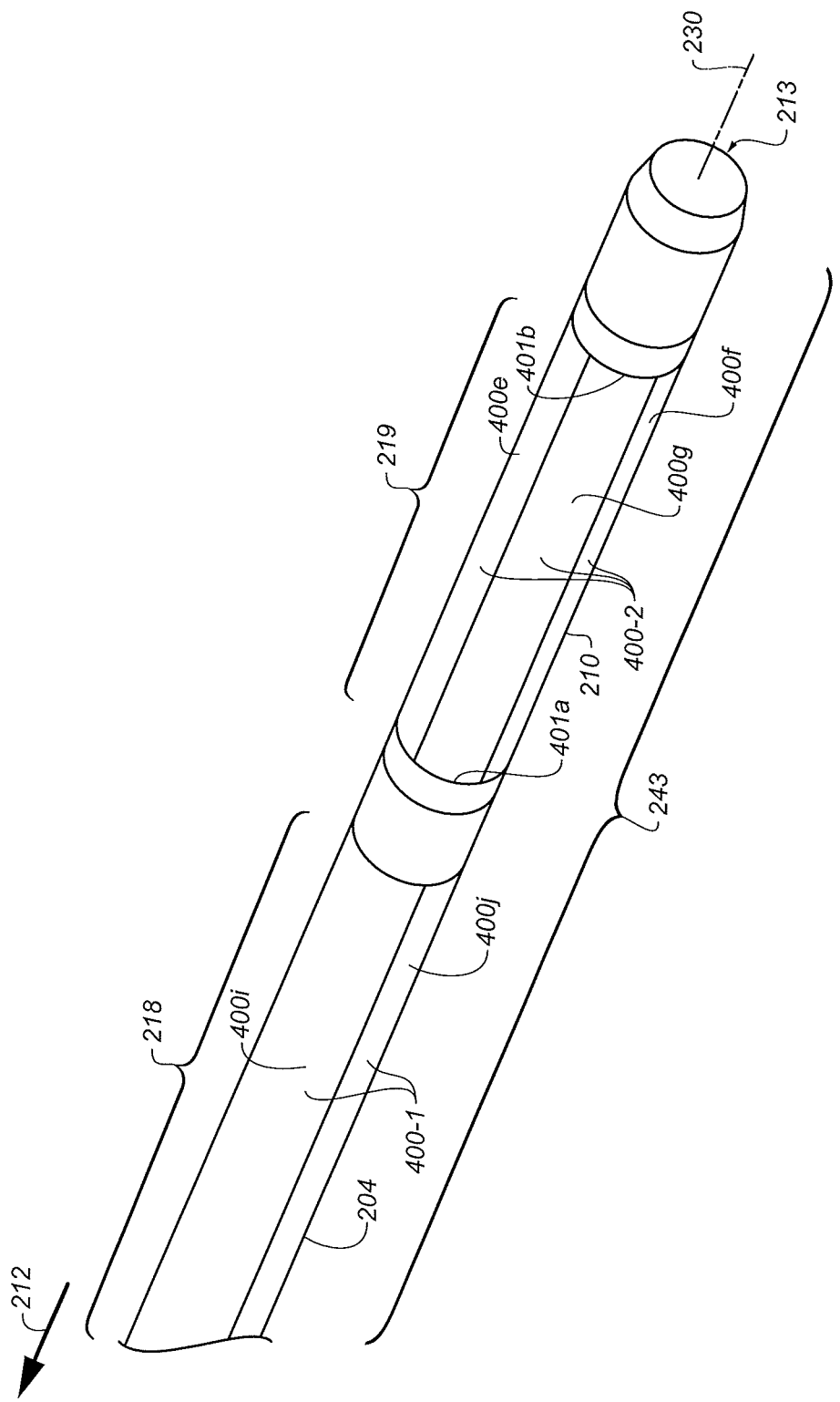

In some embodiments, at least one material of the first group of materials is a polymer material. In some embodiments, at least one material of the second group of materials is a polymer material. In some embodiments, the first group of materials and the second group of materials include materials having different hardnesses. In some embodiments, the distribution of the first group of materials may be identical or similar to the distribution of different materials provided by the cross-section of the elongate shaft member 210 in FIG. 10C. In some embodiments, the distribution of the second group of materials may be identical or similar to the distribution of different materials provided by the cross-section of the elongate shaft member 210 in FIG. 10B. It is understood that other distributions of materials may be employed by at least the first group of materials or the second group of materials according to other embodiments. FIG. 11 is a perspective view of a portion of elongate shaft member 210. For ease of discussion, the elongate shaft member 210 includes the elongate strips 400 including elongate strips 400e, 400f, 400g, and 400h (400h not shown or viewable in the perspective of FIG. 11) of FIG. 10B and the elongate strips 400i and 400j of FIG. 10C, although it is understood that other arrangements of elongate strips 400 may be employed in other embodiments. The elongate shaft member 210 includes a first set of one or more materials and a second set of one or more materials, with a hardness of each material in the first set of one or more materials being greater than a hardness of each material in the second set of one or more materials. In some embodiments, each material of the first set of one or more materials is a polymer material. In some embodiments, each material of the first set of one or more materials is a polymer material. Each of the elongate strips 400 includes a first end 401a (only one called out), a second end 401b (only one called out), and a length between the first end and the second end. In various embodiments, the length of each of the plurality of elongate strips 400 is shorter than a length of the elongate shaft member 210 between the proximal and distal ends 212, 213 of the elongate shaft member 210. In various embodiments, each elongate strip 400 includes at least one material from one of the first set of one or more materials and the second set of one or more materials, but does not include a material from the other of the first set of one or more materials and the second set of one or more materials. In various embodiments, the plurality of elongate strips 400 includes at least one material in the first set of one or more materials and at least one material in the second set of one or more materials. By way of non-limiting example, the elongate strips 400g, 400h, and 400j may each include a material from the first set of one or more materials and the elongate strips 400e, 400f, and 400i may each include a material from the second set of materials. It is understood that other distributions or arrangements of materials from the first and the second sets of one or more materials may be employed in other embodiments.

According to some embodiments, the elongate shaft member 210 may include at least a first bendable portion 243 located between the proximal and the distal ends 212, 213 of the elongate shaft member 210. The first bendable portion 243 may encompass one or more parts or portions of the elongate shaft member 210. For example, in some embodiments, the first bendable portion 243 includes at least the proximal bending portion 218 of the elongate shaft member 210, the distal bending portion 219 of the elongate shaft member 210, or both. In some embodiments, the elongate shaft member 210 may include another or second bendable portion. In various embodiments, the first bendable portion 243 is bendable in at least two opposing directions (for example, directions D1 and D2 or directions D3 and D4 in FIG. 8A).

In various embodiments, the elongate strips of the plurality of elongate strips 400 are angularly arranged about a portion of the longitudinal axis 230 extending through the first bendable portion 243. In various embodiments, the plurality of elongate strips 400 includes three or more elongate strips 400. For example, in FIG. 11, the plurality of elongate strips includes six (6) elongate strips (elongate strip 400h not visible). In some embodiments, a total number of particular ones of the plurality of elongate strips 400 that each includes a material in the first set of one or more materials is the same as a total number of particular ones of the plurality of elongate strips 400 that each includes a material in the second set of one or more materials. For example, according to some embodiments, there are three elongate strips 400 (e.g., elongate strips 400g, 400h, and 400j) that each includes a material in the first set of one or more materials and three elongate strips 400 (e.g., elongate strips 400e, 400f, and 400i) that each includes a material in the second set of one or more materials. For example, elongate strips 400g, 400h, and 400j may all include the same material from the first set of one or more materials, or at least one of the elongate strips 400g, 400h, and 400j may include a different material, as compared to at least one other of the elongate strips 400g, 400h, and 400j, from the first set of one or more materials. Similarly, elongate strips 400e, 400f, and 400i may all include the same material from the second set of one or more materials, or at least one of the elongate strips 400e, 400f, and 400i may include a different material, as compared to at least one other of the elongate strips 400e, 400f, and 400i, from the second set of one or more materials.

Although in the example of FIG. 11 there are an equal number of elongate strips 400, each including, or formed from, a material in the first set of one or more materials (e.g., elongate strips 400g, 400h, and 400j) as there are elongate strips 400, each including, or formed from, a material in the second set of one or more materials (e.g., elongate strips 400e, 400f, and 400i), other embodiments are not limited to such a configuration. Accordingly, in some embodiments, a total number of particular ones of the plurality of elongate strips 400 that each includes a material in the first set of one or more materials is different than a total number of particular ones of the plurality of elongate strips 400 that each includes a material in the second set of one or more materials. In some embodiments, a first particular one of the plurality of elongate strips 400 including a material in the first set of one or more materials (e.g., elongate strip 400j) is axially offset along the portion of the longitudinal axis 230 from a second particular one of the plurality of elongate strips 400 including a material in the second set of one or more materials (e.g., elongate strip 400f). In some embodiments, a first particular one of the plurality of elongate strips 400 is axially spaced along the portion of the longitudinal axis 230 from a second particular one of the plurality of elongate strips 400 including a material in the second set of one or more materials. For example, in FIG. 11, elongate strip 400j is axially spaced from elongate strip 400f.

As shown in FIGS. 10B and 10C, according to some embodiments, a cross-section of each of the plurality of elongate strips 400 may include a respective sector-shaped profile when view along the portion of the longitudinal axis 230, each respective sector-shaped profile subtending an angular amount less than 360 degrees. In some embodiment, the respective sector-shaped profiles of at least two particular ones of the plurality of elongate strips 400 that each includes a material in the first set of one or more materials subtend different angular amounts. For example, the respective sector-shaped profiles of elongate strips 400j and 400g or elongate strips 400j or 400h subtend different angular amounts, each of the elongate strips 400j, 400g, and 400h including, or being formed from a material in the first set of one or more materials. In some embodiments, the at least two particular ones of the plurality of elongate strips 400 that include a material in the first set of one or more materials are axially offset from one another. In some embodiments, the respective sector-shaped profiles of at least two particular ones of the plurality of elongate strips 400 that each includes a material in the first set of one or more materials subtend the same angular amount. For example, the respective sector-shaped profiles of elongate strips 400g and 400h subtend the same or substantially the same angular amount.

In some embodiments, the respective sector-shaped profiles of at least two particular ones of the plurality of elongate strips 400 that each include a material in the second set of one or more materials subtend different angular amounts. For example, the respective sector-shaped profiles of elongate strips 400i and 400e or elongate strips 400i or 400f or elongate strips 400e and 400f subtend different angular amounts. In some embodiments, the at least two particular ones of the plurality of elongate strips 400 that each includes a material in the second set of one or more materials are axially offset or axially spaced from one another (for example, elongate strips 400i and 400e or elongate strips 400i or 400f). In some embodiments, the at least two particular ones of the plurality of elongate strips 400 that each includes a material in the second set of one or more materials are not axially offset or are not axially spaced from one another (for example, elongate strips 400e and 400f).

In some embodiments, the respective sector-shaped profile of a particular one of the plurality of elongate strips 400 that includes a material in the first set of one or more materials and the respective sector-shapes profile of a particular one of the plurality of elongate strips 400 that includes a material in the second set of one or more materials subtend different angular amounts. For example, different angular amounts are subtended by the respective sector-shaped profiles of each of (a) elongate strip 400j and either of elongate strips 400e and 400f, (b) elongate strip 400g and either of elongate strips 400e and 400f, (c) elongate strip 400h and either of elongate strips 400e and 400f, and (d) elongate strip 400i and either of elongate strips 400g and 400h. In some embodiments, the particular one of the plurality of elongate strips 400 that includes a material in the first set of one or more materials (e.g., elongate strip 400j) is axially offset or axially spaced from the particular one of the plurality of elongate strips 400 that includes a material in the second set of one or more materials (e.g., elongate strip 400e). In some embodiments, the particular one of the plurality of elongate strips 400 that includes a material in the first set of one or more materials (e.g., elongate strip 400g) is not axially offset or not axially spaced from the particular one of the plurality of elongate strips 400 that includes a material in the second set of one or more materials (e.g., elongate strip 400e). In some embodiments, the respective sector-shaped profile of a particular one of the plurality of elongate strips 400 that includes a material in the first set of one or more materials and the respective sector-shaped profile of a particular one of the plurality of elongate strips 400 that includes a material in the second set of one or more materials subtend substantially a same angular amount. For example, a substantially same angular amount is subtended by the respective sector-shaped profiles of each of elongate strips 400j and 400i.

In some embodiments, at least a first steering line (e.g., first or second proximal steering lines 222, 224 (not shown in FIG. 11)) is terminated at a location between a first particular elongate strip 400 including a material in the first set of one or more materials and a second particular elongate strip 400 including a material in the second set of one or more materials, the first steering line operable to cause bending of at least part of the first bendable portion 243 via movement of the first steering line. For example, according to some embodiments, first and second proximal termination portions 214, 215 of the elongate shaft member 210 are shown in FIG. 11 located between a first particular elongate strip 400 including a material in the first set of one or more materials (e.g., elongate strip 400j) and a second particular elongate strip 400 including a material in the second set of one or more materials (e.g., elongate strip 400f). As described above, the first and second steering line 222, 224 may be terminated at respective ones of the first and second proximal termination portions 214, 215 of the elongate shaft member 210. In some embodiments, the first particular elongate strip 400 including a material in the first set of one or more materials (e.g., elongate strip 400j) may form part of a first group 400-1 (shown in FIG. 11) of the plurality of elongate strips 400 (e.g., a group of elongate strips 400i, 400j) and the second particular elongate strip 400 including a material in the second set of one or more materials (e.g., elongate strip 400f) may form part of a second group 400-2 (shown in FIG. 11) of the plurality of elongate strips 400

(e.g., a group of elongate strips 400e, 400f, 400g, 400h (note that elongate strip 400h is not visible in FIG. 11). In some embodiments, each of the first group 400-1 of the plurality of elongate strips 400 and the second group 400-2 of the plurality strips 400 each respectively including at least one material from the first set of one or more materials and at least one material from the second set of one or more materials.

In some embodiments, at least some of the elongate strips of the plurality of elongate strips 400 are angularly arranged about the portion of the longitudinal axis 230 extending through the first bendable portion 243. In some embodiments, at least some of the elongate strips of the plurality of elongate strips 400 are circumferentially arranged about the portion of the longitudinal axis 230 extending through the first bendable portion 243. In some embodiments, the respective elongate strips 400 of the first group 400-1 of the plurality of elongate strips 400 (e.g., elongate strips 400i, 400j) are angularly arrayed or circumferentially arrayed about the longitudinal axis 230 at a first location on the portion of the longitudinal axis 230, and the respective elongate strips 400 of the second group 400-2 of the plurality of elongate strips 400 (e.g., elongate strips 400e, 400f, 400g, and 400h) are angularly arrayed or circumferentially arrayed about the longitudinal axis 230 at a second location on the portion of the longitudinal axis 230, the second location spaced from the first location. In some embodiments, the respective elongate strips 400 of the first group 400-1 of the plurality of elongate strips 400 (e.g., elongate strips 400i, 400j) circumferentially surround the longitudinal axis 230 at a first location on the portion of the longitudinal axis 230 and the respective elongate strips 400 of the second group 400-2 of the plurality of elongate strips 400 (e.g., elongate strips 400e, 400f, 400g, and 400h) circumferentially surround the longitudinal axis 230 at a second location on the portion of the longitudinal axis 230, the second location spaced from the first location. In some embodiments, each of the first group 400-1 of the plurality of elongate strips 400 and the second group 400-2 of the plurality of elongate strips 400 includes at least one respective particular of one of the plurality of elongate strips 400 that includes a material in the first set of one or more materials and at least one respective particular one of the plurality of elongate strips 400 that includes a material in the second set of one or more materials. For example, the first group 400-1 of the plurality of elongate strips 400 may include elongate strip 400j that includes a material from the first set of one or more materials, and elongate strip 400i that includes a material from the second set of one or more materials, while the second group 400-2 of the plurality of elongate strips 400 may include elongate strip 400g that includes a material from the first set of one or more materials, and elongate strip 400e that includes a material from the second set of one or more materials. The first group 400-1 of the plurality of elongate strips 400 includes different elongate strips 400 than the second group 400-2 of the plurality of elongate strips 400 according to various embodiments.

In some embodiments, the total number of elongate strips 400 in the first group 400-1 of the plurality of elongate strips 400 is different than the total number of elongate strips 400 in the second group 400-2 of the plurality of elongate strips 400. For example, in some embodiments the first group 400-1 of the plurality of elongate strips 400 has two elongate strips (e.g., elongate strips 400i, 400j) and the second group 400-2 of the plurality of elongate strips 400 has four elongate strips (e.g., elongate strips 400e, 400f, 400g, 400h).

In some embodiments, the total number of particular ones of the elongate strips 400 in the first group 400-1 of the plurality of elongate strips 400 that each includes a material in the first set of one or more materials is different than the total number of particular ones of the elongate strips 400 in the second group 400-2 of the plurality of elongate strips 400 that each includes a material in the first set of one or more materials. For example, in some embodiments associated with FIG. 11, the first group 400-1 of the plurality of elongates strips 400 (e.g., elongate strips 400i, 400j) includes one (1) elongate strip (e.g., elongate strip 400j) that includes or is formed from a material in the first set of one or more materials, while the second group 400-2 of the plurality of elongates strips 400 (e.g., elongate strips 400e, 400f, 400g, 400h) includes two (2) elongate strip (e.g., elongate strips 400g, 400h) that each includes or is formed from a material in the first set of one or more materials.

In some embodiments, the total number of particular ones of the elongate strips 400 in the first group 400-1 of the plurality of elongate strips 400 that each includes a material in the second set of one or more materials is different than the total number of particular ones of the elongate strips 400 in the second group 400-2 of the plurality of elongate strips 400 that each includes a material in the second set of one or more materials. For example, in some embodiments associated with FIG. 11, the first group 400-1 of the plurality of elongates strips 400 (e.g., elongate strips 400i, 400j) includes one (1) elongate strip (e.g., elongate strip 400i) that includes or is formed from a material in the second set of one or more materials while the second group 400-2 of the plurality of elongates strips 400 (e.g., elongate strips 400e, 400f, 400g, 400h) includes two (2) elongate strip (e.g., elongate strips 400e, 400f) that each includes or is formed from a material in the second set of one or more materials.

While some of the embodiments disclosed above are described with examples of cardiac procedures, the same or similar embodiments may be used for procedures for other bodily organs or any lumen or cavity into which the devices of the present invention may be introduced.

Subsets or combinations of various embodiments described above provide further embodiments.

These and other changes can be made to the invention in light of the above-detailed description. In general, in the following claims, the terms used should not be construed to limit the invention to the specific embodiments disclosed in the specification and the claims, but should be construed to include other transducer-based device systems including all medical treatment device systems and medical diagnostic device systems in accordance with the claims. Accordingly, the invention is not limited by the disclosure, but instead its scope is to be determined entirely by the following claims.

What is claimed is:

1. A medical system comprising:
an elongate shaft member, sized for percutaneous delivery at least partially through a bodily opening to a bodily cavity, and including a first lumen, the elongate shaft member comprising a proximal steering ring disposed at a proximal bending portion of the elongate shaft member, and a distal steering ring, disposed at a distal bending portion of the elongate shaft member; and
a plurality of steering lines, each terminated at respective locations along the elongate shaft member,
wherein the plurality of steering lines includes first and second pairs of steering lines, each steering line of the plurality of steering lines comprising a respective first end portion including a first end of the steering line and a respective second end portion including a second end of the steering line, the first end portion and the second end portion spaced from one another across a length of the steering line, wherein the first pair of steering lines includes a first proximal steering line and a first distal steering line, and the second pair of steering lines includes a second proximal steering line and a second distal steering line, wherein the respective second end portion of the first proximal steering line terminates at a first proximal termination portion of the elongate shaft member, and the respective second end portion of the first distal steering line terminates at a first distal termination portion of the elongate shaft member, wherein the respective second end portion of the second proximal steering line terminates at a second proximal termination portion of the elongate shaft member, and the respective second end portion of the second distal steering line terminates at a second distal termination portion of the elongate shaft member, wherein the steering lines of the plurality of steering lines are operable to cause bending of the elongate shaft member via movement of at least one of the steering lines, wherein the respective second end portions of the first proximal steering line and the second proximal steering line are terminated at the proximal steering ring, and the respective second end portions of the first distal steering line and the second distal steering line are terminated at the distal steering ring, wherein the proximal steering ring includes a first semi-circular ring portion and a second semi-circular ring portion, each of the first semi-circular ring portion and the second semi-circular ring portion including respective first and second edge portions, wherein the first and second edge portions of the first semi-circular ring portion are circumferentially spaced from one another along the first semi-circular ring portion, wherein the first and second edge portions of the second semi-circular ring portion are circumferentially spaced from one another along the second semi-circular ring portion, wherein the respective second end portion of the first proximal steering line terminates at the first semi-circular ring portion and the respective second end portion of the second proximal steering line terminates at the second semi-circular ring portion, wherein the first semi-circular ring portion and the second semi-circular ring portion are disposed apart from each other, and wherein the respective first edge portions of the first and the second semi-circular ring portions define a first gap and the respective second edge portions of the first and the second semi-circular ring portions define a second gap.

2. The medical system of claim 1, wherein the plurality of steering lines are disposed within an exterior wall of the elongate shaft member.

3. The medical system of claim 1, wherein the first distal steering line passes through the first gap, and the second distal steering line passes through the second gap.

4. The medical system of claim 1, wherein the plurality of steering lines are angularly spaced about a longitudinal axis of the elongate shaft member, as viewed along the longitudinal axis of the elongate shaft member, and wherein at least (a) an angular spacing between the first proximal steering line and the second distal steering line is approximately 180 degrees, or (b) an angular spacing between the second proximal steering line and the first distal steering line is approximately 180 degrees.

5. The medical system of claim 4, wherein the elongate shaft member comprises a proximal end and a distal end, and wherein each of the first distal termination portion of the elongate shaft member and the second distal termination portion of the elongate shaft member is located relatively closer to the distal end of the elongate shaft member than each of the first proximal termination portion of the elongate shaft member and the second proximal termination portion of the elongate shaft member.

6. The medical system of claim 4,
wherein the elongate shaft member permits opposing movement of the first proximal steering line and the second proximal steering line to bend a proximal bending portion of the elongate shaft member in a first direction of two opposing directions within a first plane, and permits opposing movement of the first proximal steering line and the second proximal steering line to bend the proximal bending portion of the elongate shaft member in a second direction of the two opposing directions within the first plane, the second direction of the two opposing directions within the first plane opposite to the first direction of the two opposing directions within the first plane, and wherein the elongate shaft member permits opposing movement of the first distal steering line and the second distal steering line to bend a distal bending portion of the elongate shaft member in a first direction of two opposing directions within a second plane, and permits opposing movement of the first distal steering line and the second distal steering line to bend the distal bending portion of the elongate shaft member in a second direction of the two opposing directions within the second plane, the second direction of the two opposing directions within the second plane opposite to the first direction of the two opposing directions within the second plane.

7. The medical system of claim 1, wherein the plurality of steering lines are arranged in an arrangement in which the plurality of steering lines are angularly arranged about a longitudinal axis of the elongate shaft member, as viewed along the longitudinal axis, and wherein an angular spacing between the steering lines of a first adjacent pair of the steering lines in the arrangement is different than an angular spacing between the steering lines of a second adjacent pair of the steering lines in the arrangement.

8. The medical system of claim 7, wherein the first adjacent pair of the steering lines is provided by the first proximal steering line and the first distal steering line, and wherein the second adjacent pair of the steering lines is provided by (a) the first proximal steering line and one of the second proximal steering line and the second distal steering line, or (b) the first distal steering line and one of the second proximal steering line and the second distal steering line.

9. The medical system of claim 8, wherein the angular spacing between the steering lines of the first adjacent pair of the steering lines is smaller than the angular spacing between the steering lines of the second adjacent pair of the steering lines.

10. The medical system of claim 1, wherein the plurality of steering lines are angularly arranged about a longitudinal axis of the elongate shaft member, as viewed along the longitudinal axis, and wherein at least (a) an angular spacing between the first proximal steering line and the first distal steering line is less than 80 degrees, or (b) an angular spacing between the second proximal steering line and the second distal steering line is less than 80 degrees.

11. The medical system of claim 1,
wherein the elongate shaft member permits a set of the plurality of steering lines to be moved to cause a first portion of a projected outline of the elongate shaft member to include a first curve and a second portion of the projected outline to include a second curve, and
wherein the first curve is concave toward a first region of space, and the second curve is convex toward the first region of space.

12. The medical system of claim 11,
wherein the first curve of the projected outline corresponds to a first curve segment of the elongate shaft member, and the second curve of the projected outline corresponds to a second curve segment of the elongate shaft member, and
wherein the first curve segment and the second curve segment are within a same plane.

13. The medical system of claim 12, wherein the first curve segment is located proximal at least (a) the first proximal termination portion of the elongate shaft member or (b) the second proximal termination portion of the elongate shaft member, and the second curve segment is located distal at least (a) or (b).

14. The medical system of claim 1,
wherein the elongate shaft member comprises a proximal end and a distal end,
wherein the elongate shaft member permits a set of the plurality of steering lines to be moved to cause a proximal bending portion of the elongate shaft member to include a first curve segment and a distal bending portion of the elongate shaft member to include a second curve segment, the distal bending portion of the elongate shaft member positioned relatively closer to the distal end of the elongate shaft member than the proximal bending portion of the elongate shaft member, and
wherein the first curve segment is concave toward a first region of space and the second curve segment is convex toward the first region of space.

15. The medical system of claim 14, wherein each of the first distal termination portion of the elongate shaft member and the second distal termination portion of the elongate shaft member is located relatively closer to the distal end of the elongate shaft member than each of the first proximal termination portion of the elongate shaft member and the second proximal termination portion of the elongate shaft member.

16. The medical system of claim 15, wherein the proximal bending portion is positioned proximal at least (a) the first proximal termination portion of the elongate shaft member or (b) the second proximal termination portion of the elongate shaft member, and the distal bending portion of the elongate shaft member is located distal at least (a) or (b).

17. The medical system of claim 14, wherein the first curve segment and the second curve segment are within a same plane.

18. The medical system of claim 17, wherein the first curve segment is located proximal at least (a) the first proximal termination portion of the elongate shaft member or (b) the second proximal termination portion of the elongate shaft member, and the second curve segment is located distal at least (a) or (b).

19. The medical system of claim 14, wherein the first curve segment is located proximal at least (a) the first proximal termination portion of the elongate shaft member or (b) the second proximal termination portion of the elongate shaft member, and the second curve segment is located distal at least (a) or (b).

20. The medical system of claim 14,
wherein the elongate shaft member includes a first set of one or more materials and a second set of one or more materials, wherein a hardness of each material in the first set of one or more materials is greater than a hardness of each material in the second set of one or more materials,
wherein the elongate shaft member includes a plurality of elongate strips, a length of each of the plurality of elongate strips being shorter than a length of the elongate shaft member between the proximal and distal ends of the elongate shaft member,
wherein each elongate strip of the plurality of elongate strips comprises at least one material from one of the first set of one or more materials and the second set of one or more materials but does not comprise a material from the other of the first set of one or more materials and the second set of one or more materials, the plurality of elongate strips including at least one material from the first set of one or more materials and at least one material from the second set of one or more materials, and
wherein a first elongate strip of the plurality of elongate strips comprises a material from the first set of one or more materials, the first elongate strip located at a convex side of the proximal bending portion of the elongate shaft member, and wherein a second elongate strip of the plurality of elongate strips comprises a material from the second set of one or more materials, the second elongate strip located at a concave side of the distal bending portion of the elongate shaft member.

21. The medical system of claim 20, wherein at least (a) the first set of one or more materials comprises one or more polymer materials or (b) the second set of one or more materials comprises one or more polymer materials.

22. The medical system of claim 20,
wherein the proximal bending portion is located proximal at least (a) the first proximal termination portion or (b) the second proximal termination portion, and
wherein the distal bending portion is located distal at least (a) or (b).

23. The medical system of claim 20, wherein a third elongate strip of the plurality of elongate strips comprises a material from the second set of one or more materials, the third elongate strip located at a concave side of the proximal bending portion of the elongate shaft member.

24. The medical system of claim 23, wherein a fourth elongate strip of the plurality of elongate strips comprises a material from the second set of one or more materials, the fourth elongate strip located at a convex side of the distal bending portion of the elongate shaft member.

25. The medical system of claim 24, wherein at least (a) the first elongate strip of the plurality of elongate strips comprises a polymer material, (b) the second elongate strip of the plurality of elongate strips comprises a polymer material, (c) the third elongate strip of the plurality of elongate strips comprises a polymer material or (d) the fourth elongate strip of the plurality of elongate strips comprises a polymer material.

26. The medical system of claim 20, wherein each elongate strip of the plurality of elongate strips comprises a thickness, a front surface facing radially outwardly from a longitudinal axis of the elongate shaft member, a back surface opposite across the thickness from the front surface, and a respective pair of side edges that define a portion of a periphery of at least one of the front surface and the back surface, the side edges of each pair of side edges opposed to one another across at least a portion of the length of the elongate strip, the elongate strip including a width between each pair of side edges, wherein the width of each of the plurality of elongate strips is smaller than a circumference of the elongate shaft member.

27. The medical system of claim 20, wherein a respective cross-section of at least the first elongate strip or the second elongate strip comprises a sector-shaped profile when viewed along a longitudinal axis of the elongate shaft member, each sector-shaped profile subtending an angle less than 360 degrees.

28. The medical system of claim 1,
wherein the elongate shaft member comprises a proximal end and a distal end,
wherein the elongate shaft member comprises a proximal bending portion and a distal bending portion, the distal bending portion of the elongate shaft member positioned relatively closer to the distal end of the elongate shaft member than the proximal bending portion of the elongate shaft member,
wherein the proximal bending portion is bendable in two opposing directions within a first plane, in response to movement of at least a first set of the plurality of steering lines,
wherein the distal bending portion is bendable in two opposing directions within a second plane, in response to movement of at least a second set of the plurality of steering lines,
wherein a first group of materials are distributed in the proximal bending portion to resist bending, in response to movement of the first set of the plurality of steering lines, of the proximal bending portion in one of a first direction of the two opposing directions within the first plane with a greater resistance than in bending, in response to movement of the first set of the plurality of steering lines, of the proximal bending portion in a second direction of the two opposing directions within the first plane, the second direction of the two opposing directions within the first plane opposite to the first direction of the two opposing directions within the first plane,
wherein a second group of materials are distributed in the distal bending portion to resist bending, in response to movement of the second set of the plurality of steering lines, of the distal bending portion in a first direction of the two opposing directions within the second plane with a greater resistance than in bending, in response to movement of the second set of the plurality of steering lines, of the distal bending portion in a second direction of the two opposing directions within the second plane, the second direction of the two opposing directions within the second plane opposite to the first direction of the two opposing directions within the second plane, and
wherein each of the first group of materials and the second group of materials comprises materials having different hardnesses.

29. The medical system of claim 28, wherein at least the first group of materials comprises one or more polymer materials or the second group of materials comprises one or more polymer materials.

30. The medical system of claim 28,
wherein the elongate shaft member permits opposing movement of the first proximal steering line and the second proximal steering line to bend the proximal bending portion of the elongate shaft member in the first direction of the two opposing directions within the first plane, and permits opposing movement of the first proximal steering line and the second proximal steering line to bend the proximal bending portion of the elongate shaft member in the second direction of the two opposing directions within the first plane, and
wherein the elongate shaft member permits opposing movement of the first distal steering line and the second distal steering line to bend the distal bending portion of the elongate shaft member in the first direction of the two opposing directions within the second plane, and permits opposing movement of the first distal steering line and the second distal steering line to bend the distal bending portion of the elongate shaft member in the second direction of the two opposing directions within the second plane.

31. The medical system of claim 28,
wherein the proximal bending portion is located proximal at least (a) the first proximal termination portion or (b) the second proximal termination portion, and
wherein the distal bending portion is located distal at least (a) or (b).

32. The medical system of claim 1,
wherein the elongate shaft member comprises a proximal end and a distal end,
wherein the elongate shaft member comprises a proximal bending portion and a distal bending portion, the distal bending portion of the elongate shaft member positioned relatively closer to the distal end of the elongate shaft member than the proximal bending portion of the elongate shaft member,
wherein the elongate shaft member includes a first set of one or more materials and a second set of one or more materials, wherein a hardness of each material in the first set of one or more materials is greater than a hardness of each material in the second set of one or more materials,
wherein the elongate shaft member includes a plurality of elongate strips, a length of each of the plurality of elongate strips being shorter than a length of the elongate shaft member between the proximal and distal ends of the elongate shaft member, wherein each elongate strip of the plurality of elongate strips comprises at least one material from one of the first set of one or more materials and the second set of one or more materials but does not comprise a material from the other of the first set of one or more materials and the second set of one or more materials,
wherein each of the proximal bending portion and the distal bending portion comprises a respective group of the elongate strips angularly arrayed about a longitudinal axis of the elongate shaft member, and
wherein for each respective group of the elongate strips, at least a first elongate strip of the respective group of the elongate strips comprises a material from the first set of one or more materials, and at least a second elongate strip of the respective group of the elongate strips comprises a material from the second set of one or more materials.

33. The medical system of claim 32, wherein at least (a) the first set of one or more materials comprises one or more polymer materials or (b) the second set of one or more materials comprises one or more polymer materials.

34. The medical system of claim 32, wherein the respective group of the elongate strips of the proximal bending portion comprises a different number of the elongate strips than a number of the elongate strips comprised by the respective group of the elongate strips of the distal bending portion.

35. The medical system of claim 32,
wherein the respective group of the elongate strips of the proximal bending portion includes a first number of particular ones of the elongate strips each comprising a material from the first set of one or more materials, and the respective group of the elongate strips of the distal bending portion includes a second number of particular ones of the elongate strips each comprising a material from the first set of one or more materials, and
wherein the first number is different from the second number.

36. The medical system of claim 32,
wherein the respective group of the elongate strips of the proximal bending portion includes a first number of particular ones of the elongate strips each comprising a material from the second set of one or more materials, and the respective group of the elongate strips of the distal bending portion includes a second number of particular ones of the elongate strips each comprising a material from the second set of one or more materials, and
wherein the first number is different from the second number.

37. The medical system of claim 32, wherein for each respective group of at least one of the respective groups of the elongate strips, a number of particular ones of the elongate strips of the respective group each comprising a material from the first set of one or more materials is the same as a number of particular ones of the elongate strips of the respective group each comprising a material from the second set of one or more materials.

38. The medical system of claim 32, wherein for each respective group of at least one of the respective groups of the elongate strips, a number of particular ones of the elongate strips of the respective group each comprising a material from the first set of one or more materials is different than a number of particular ones of the elongate strips of the respective group each comprising a material from the second set of one or more materials.

39. The medical system of claim 32, wherein the elongate strips of each respective group of the elongate strips are disposed at a position distanced apart from a geometric center of the elongate shaft member, when viewed along the longitudinal axis of the elongate shaft member.

40. The medical system of claim 32,
wherein the proximal bending portion is located proximal at least (a) the first proximal termination portion or (b) the second proximal termination portion, and
wherein the distal bending portion is located distal at least (a) or (b).

41. The medical system of claim 1,
wherein the elongate shaft member comprises a proximal end and a distal end,
wherein the elongate shaft member comprises a proximal bending portion and a distal bending portion, the distal bending portion located closer to the distal end of the elongate shaft member than the proximal bending portion,
wherein the elongate shaft member includes a first material and a second material,
wherein a hardness of the first material is greater than a hardness of the second material, and
wherein each of the proximal bending portion and the distal bending portion comprises the first material and the second material, and wherein a spatial distribution between the first material and the second material in the proximal bending portion is different than a spatial distribution between the first material and the second material in the distal bending portion.

42. The medical system of claim 41, wherein at least the first material is a polymer material or the second material is a polymer material.

43. The medical system of claim 41,
wherein the proximal bending portion is located proximal at least (a) the first proximal termination portion or (b) the second proximal termination portion, and
wherein the distal bending portion is located distal at least (a) or (b).

44. The medical system of claim 1,
wherein the elongate shaft member includes at least a first material and a second material,
wherein a hardness of the first material is greater than a hardness of the second material, and
wherein the first material and the second material are distributed in the elongate shaft member to provide an off-center neutral axis of the elongate shaft member with respect to a longitudinal axis of the elongate shaft member that passes through a geometric center of a cross-section of the elongate shaft member, the cross-section transverse to the longitudinal axis.

45. The medical system of claim 44, wherein at least the first material is a polymer material or the second material is a polymer material.

46. The medical system of claim 1,
wherein the elongate shaft member comprises a proximal end and a distal end,
wherein the elongate shaft member comprises a proximal bending portion and a distal bending portion, the distal bending portion located closer to the distal end of the elongate shaft member than the proximal bending portion,
wherein the elongate shaft member includes at least a first material, a second material, a third material and a fourth material,
wherein a hardness of the first material is greater than a hardness of the second material,
wherein a hardness of the third material is greater than a hardness of the fourth material,
wherein a first distribution of the first material and the second material exists in the proximal bending portion to provide an off-center neutral axis of the proximal bending portion with respect to a longitudinal axis of the elongate shaft member that passes through a geometric center of a cross-section of the elongate shaft member, the cross-section transverse to the longitudinal axis, and
wherein a second distribution of the third material and the fourth material exists in the distal bending portion to provide an off-center neutral axis of the distal bending portion with respect to the longitudinal axis of the elongate shaft member that passes through the geometric center of the cross-section of the elongate shaft member, a location of the off-center neutral axis of the distal bending portion as viewed along a part of the longitudinal axis of the elongate shaft member extending through the distal bending portion being different than a location of the off-center neutral axis of the proximal bending portion as viewed along a part of the longitudinal axis of the elongate shaft member extending through the proximal bending portion.

47. The medical system of claim 46, wherein the off-center neutral axis of the proximal bending portion and the off-center neutral axis of the distal bending portion are on opposite sides of the longitudinal axis as viewed along a direction of the longitudinal axis.

48. The medical system of claim 46, wherein the off-center neutral axis of the proximal bending portion and the off-center neutral axis of the distal bending portion are parallel to one another.

49. The medical system of claim 46, wherein the off-center neutral axis of the proximal bending portion and the off-center neutral axis of the distal bending portion correspond to a bending of each of the proximal bending portion and the distal bending portion within a same plane.

50. The medical system of claim 46, wherein at least (a) the first material comprises a polymer material, (b) the second material comprises a polymer material, (c) the third material comprises a polymer material or (d) the fourth material comprises a polymer material.

51. The medical system of claim 46,
wherein the proximal bending portion is located proximal at least (a) the first proximal termination portion or (b) the second proximal termination portion, and
wherein the distal bending portion is located distal at least (a) or (b).

52. The medical system of claim 46, wherein each of the first material and the second material is different than at least one of the third material and the fourth material.

53. The medical system of claim 1, wherein each respective steering line of the plurality of steering lines comprises a respective cross-sectional area when viewed in a direction along a respective longitudinal axis of the respective steering line, the respective cross-sectional area transverse to the respective longitudinal axis, and wherein the respective cross-sectional area of the first proximal steering line is different than the respective cross-sectional area of the first distal steering line.

54. The medical system of claim 53, wherein the respective cross-sectional area of the first distal steering line is greater than at least the respective cross-sectional area of (a) the first proximal steering line or (b) the second proximal steering line, or (c) the second distal steering line.

55. The medical system of claim 1, wherein the elongate shaft member is an elongate sheath, the elongate sheath comprising a lumen sized to selectively allow passage of a medical instrument therethrough during percutaneous delivery of the medical instrument along a path through the lumen.

56. The medical system of claim 1, comprising an expandable structure coupled to an end of the elongate shaft member.

* * * * *